United States Patent [19]
Cho et al.

[11] Patent Number: 6,028,195
[45] Date of Patent: Feb. 22, 2000

[54] PIPERAZINE DERIVATIVES AND PROCESS FOR THE PREPARATION THEREOF

[75] Inventors: Eui-Hwan Cho, Seoul; Sun-Gan Chung, Kyungki-do; Sun-Hwan Lee, Kyungki-do; Ho-Seok Kwon, Kyungki-do; Jae-Eung Lee, Kyungki-do; Dong-Wook Kang, Kyungki-do; Jeong-Ho Joo, Seoul; Young-Hee Lee, Kyungki-do, all of Rep. of Korea

[73] Assignee: Samjin Pharmaceutical Co., Ltd., Seoul, Rep. of Korea

[21] Appl. No.: 09/029,660

[22] PCT Filed: Jun. 28, 1997

[86] PCT No.: PCT/KR97/00128

§ 371 Date: Feb. 27, 1998

§ 102(e) Date: Feb. 27, 1998

[87] PCT Pub. No.: WO98/00402

PCT Pub. Date: Jan. 8, 1998

[30] Foreign Application Priority Data

| Jun. 29, 1996 | [KR] | Rep. of Korea | 96-25825 |
| Jun. 29, 1996 | [KR] | Rep. of Korea | 96-25826 |
| Jun. 29, 1996 | [KR] | Rep. of Korea | 96-25827 |
| Sep. 18, 1996 | [KR] | Rep. of Korea | 96-40596 |
| Jun. 3, 1997 | [KR] | Rep. of Korea | 97-22984 |
| Jun. 3, 1997 | [KR] | Rep. of Korea | 97-22985 |
| Jun. 4, 1997 | [KR] | Rep. of Korea | 97-23192 |
| Jun. 4, 1997 | [KR] | Rep. of Korea | 97-23193 |

[51] Int. Cl.[7] ............................ C07D 401/12; A61K 31/495
[52] U.S. Cl. ......................... 544/360; 544/363; 544/364; 544/389; 544/390; 544/252; 544/253; 544/255
[58] Field of Search .................................. 544/360, 363, 544/364, 389, 390; 514/253, 255, 252

[56] References Cited

U.S. PATENT DOCUMENTS

| 4,016,274 | 4/1977 | Cotrel et al. | 424/250 |
| 4,038,391 | 7/1977 | Cotrel et al. | 424/250 |
| 5,218,002 | 6/1993 | Stroech et al. | 514/919 |
| 5,387,593 | 2/1995 | Mattson et al. | 546/194 |
| 5,391,571 | 2/1995 | Mewshaw et al. | 514/490 |
| 5,461,047 | 10/1995 | Hansen, Jr. et al. | 514/211 |
| 5,478,828 | 12/1995 | Mattson et al. | 514/253 |
| 5,482,948 | 1/1996 | Soyka et al. | 514/318 |
| 5,780,472 | 7/1998 | Cho et al. | 514/252 |
| 5,789,412 | 8/1998 | Halazy et al. | 514/255 |

FOREIGN PATENT DOCUMENTS

| 96 025 25 | 2/1996 | WIPO . |
| WO9621648 | 7/1996 | WIPO . |

OTHER PUBLICATIONS

Advanced Organic Chemistry by Jerry March (2nd Ed.) p. 378–379, 1977.
J. Med. Chem., 1992, 35, 3784–3791, Hoffman et al.
J. Med. Chem., 1992, 35, 3792–3802, Saari et al.
Chemical Abstracts, vol. 110, No. 4, Jan. 23, 1989 p. 499, Yoshimoto et al.

*Primary Examiner*—Emily Bernhardt
*Attorney, Agent, or Firm*—Birch, Stewart, Kolasch & Birch, LLP

[57] ABSTRACT

The present invention relates to novel compound having strong antimumor activities of the general formula(I)

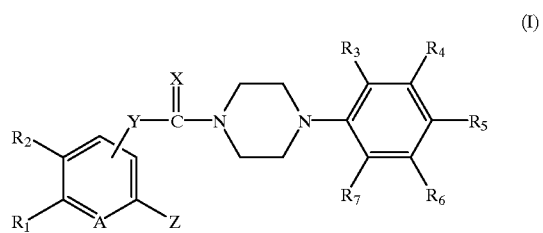

wherein $R_1$ and $R_2$ are independently hydrogen, substituted or unsubstituted $C_1$–$C_8$ alkyl, substituted or unsubstituted $C_3$–$C_6$ cycloalkyl, substituted or unsubstituted $C_2$–$C_8$ unsaturated alkyl, ketone, substituted or unsubstituted aryl, substituted or unsubstituted $C_1$–$C_4$ alkoxy, substituted or unsubstituted arylhydroxy, substituted or unsubstituted amino, $C_1$–$C_4$ lower ester, $C_1$–$C_4$ lower thioester, thiol, substituted or unsubstituted carboxyl, epoxy, substituted or unsubstituted $C_1$–$C_4$ lower thioalkoxy; or $R_1$ and $R_2$ are fused to form $C_3$–$C_4$ saturated or unsaturated chain; $R_3$, $R_4$, $R_5$, $R_6$ and $R_7$ are independently hydrogen, halogen, hydroxy, nitro, $C_1$–$C_4$ lower ester, $C_1$–$C_4$ lower alkyl, $C_1$–$C_4$ lower thioalkyl, substituted or unsubstituted $C_3$–$C_6$ cycloalkyl, $C_1$–$C_4$ lower alkoxy, $C_1$–$C_4$ lower thioalkoxy, substituted or unsubstituted aryl, substituted or unsubstituted lower arylalkoxy, substituted or unsubstituted lower alkylamino, or lower alkyl substituted or unsubstituted carbamate; or among $R_3$, $R_4$, $R_5$, $R_6$ and $R_7$, two adjacent groups are bonded with each other to form 1,2-phenylene or 2,3-naphthylene; X is oxygen, sulfur, or substituted or unsubstituted imino; Y is bonded at the 3-position or 4-position of the aromatic ring part wherein Y is oxygen or —$NR_8$— (wherein, $R_8$ is the same with the above-mentioned $R_3$.); Z is hydroxy, $C_1$–$C_4$ lower alkoxy, $C_1$–$C_4$ lower thioalkoxy, substituted or unsubstituted aryloxy, $C_1$–$C_4$ lower alkylamino, substituted or unsubstituted cycloamino containing 1–5 nitrogen atoms; A is nitrogen or —CH=; its pharmaceutically acceptable acid addition salts and process for the preparation thereof.

3 Claims, No Drawings

PIPERAZINE DERIVATIVES AND PROCESS FOR THE PREPARATION THEREOF

This application is the national phase under 35 U.S.C. §371 of prior PCT International Application No. PCT/KR97/00128 which has an International filing date of Jun. 28, 1997 which designated the United States of America, the entire contents of which are hereby incorporated by reference.

The present invention relates to new piperazine derivatives of the general formula (I)

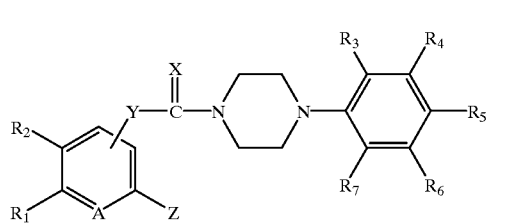

wherein $R_1$ and $R_2$ are independently hydrogen, substituted or unsubstituted $C_1$–$C_8$ alkyl, substituted or unsubstituted $C_3$–$C_6$ cycloalkyl, substituted or unsubstituted $C_2$–$C_8$ unsaturated alkyl, ketone, substituted or unsubstituted aryl, substituted or unsubstituted $C_1$–$C_4$ alkoxy, substituted or unsubstituted arylhydroxy, substituted or unsubstituted amino, $C_1$–$C_4$ lower ester, $C_1$–$C_4$ lower thioester, thiol, substituted or unsubstituted carboxyl, epoxy, substituted or unsubstituted $C_1$–$C_4$ lower thioalkoxy; or $R_1$ and $R_2$ are fused to form $C_3$–$C_4$ saturated or unsaturated chain; $R_3$, $R_4$, $R_5$, $R_6$ and $R_7$ are independently hydrogen, halogen, hydroxy, nitro, $C_1$–$C_4$ lower ester, $C_1$–$C_4$ lower alkyl, $C_1$–$C_4$ lower thioalkyl, substituted or unsubstituted $C_3$–$C_6$ cycloalkyl, $C_1$–$C_4$ lower alkoxy, $C_1$–$C_4$ lower thioalkoxy, substituted or unsubstituted aryl, substituted or unsubstituted lower arylalkoxy, substituted or unsubstituted lower alkylamino, or lower alkyl substituted or unsubstituted carbamate; or among $R_3$, $R_4$, $R_5$, $R_6$ and $R_7$, two adjacent groups are bonded with each other to form 1,2-phenylene or 2,3-naphthylene; X is oxygen, sulfur, or substituted or unsubstituted imino; Y is bonded at the 3-position or 4-position of the aromatic ring part wherein Y is oxygen or —$NR_8$— (wherein, $R_8$ is the same with the above-mentioned $R_3$.); Z is hydroxy, $C_1$–$C_4$ lower alkoxy, $C_1$–$C_4$ lower thioalkoxy, substituted or unsubstituted aryloxy, $C_1$–$C_4$ lower alkylamino, substituted or unsubstituted cycloamino containing 1–5 nitrogen atoms; A is nitrogen or —CH=; its pharmaceutically acceptable acid addition salts and process for the preparation thereof.

In the above definitions, $C_1$–$C_8$ alkyl means straight or branched alkyl group such as methyl, ethyl, propyl, isopropyl, n-butyl, isobutyl, tert-butyl, pentyl, iso-pentyl, hexyl, heptyl, octyl, 2-methylpentyl or the like.

$C_1$–$C_4$ lower alkyl means methyl, ethyl, propyl, isopropyl, n-butyl, iso-butyl or tert-butyl.

Substituted or unsubstituted $C_3$–$C_6$ cycloalkyl means substituted or unsubstituted cycloalkyl such as cyclopropyl, cyclobutyl, cyclopentyl, cyclohexyl, substituted cyclopropyl, substituted cyclopentyl, substituted cyclohexyl or the like.

$C_1$–$C_4$ lower ester means a carboxyl group esterified by a lower alkyl group.

$C_1$–$C_4$ lower alkoxy means methoxy, ethoxy, propoxy, isopropoxy, butyloxy, isobutyloxy, tert-butyloxy group or the like.

$C_1$–$C_4$ lower thioalkoxy means methylthio, ethylthio, propylthio, isopropylthio, butylthio, isobutylthio, tert-butylthio group or the like.

$C_1$–$C_4$ lower alkylamino means methylamino, ethylamino, propylamino, butylamino group or the like.

Aryloxy means phenoxy, substituted phenoxy, naphthyloxy or substituted naphthyloxy or the like.

Cycloamino group containing 1–5 nitrogen atoms means pyrrolidinyl, pyrrolinyl, imidazolyl, imidazolidinyl, pyrazolyl, pyrazolinyl, pyrazolidinyl, triazolyl, tetrazolyl, piperazinyl or the like.

The present inventors had studied for a long time to find compounds having intensive antitumor activity. As the results, now we have finally found out the facts that the present compounds of the general formula(I) and acid addition salts thereof have not only prominent antitumor activities but very low toxicities.

Accordingly, the one object of the present invention is to provide the novel compounds of the general formula(I) and acid addition salts thereof having not only prominent antitumor activities but very low toxicities.

The other object of the present invention is to provide a process for the preparation of the compounds of general formula(I) and acid addition salts thereof.

The compounds of the present invention can be mixed with pharmaceutically acceptable vehicles by a known method to give pharmaceutical compositions and the pharmaceutical compositions can be used to prevent or treat with various kinds of tumors of human beings or mammals.

Therefore, another object of the present invention is to provide pharmaceutical compositions containing the compounds of the general formula(I) or acid addition salts thereof as active ingredients. Acids which can be reacted with the compounds of the general formula(I) to form acid addition salts are pharmaceutically acceptable inorganic or organic acids; for example, inorganic acids such as hydrochloric acid, bromic acid, sulfuric acid, phosphonic acid, nitric acid; organic acids such as formic acid, acetic acid, propionic acid, succinic acid, citric acid, maleic acid, malonic acid, glycolic acid, lactic acid; amino acids such as glycine, alanine, valine, leucine. Isoleucine, serine, cysteine, cystine, asparaginic acid, glutamic acid, lysine, arginine, tyrosine, proline; sulfonic acids such as methane sulfonic acid, ethane sulfonic acid, benzene sulfonic acid, toluene sulfonic acid; or the like. Vehicles which can be used in the preparation of pharmaceutical compositions containing the compounds of the general formula(I) as active ingredients are sweetening agent, binding agent, dissolving agent, aids for dissolution, wetting agent, emulsifying agent, isotonic agent, adsorbent, degrading agent, antioxident, antiseptics, lubricating agent, filler, perfume or the like; such as lactose, dextrose, sucrose, mannitol, sorbitol, cellulose, glycine, silica, talc, stearic acid, stearin, magnesium stearate, calcium stearate, magnesium aluminum silicate, starch, gelatine, tragacanth gum, glycine, silica, alginic acid, sodium alginate, methyl cellulose, sodium carboxy methyl cellulose, agar, water, ethanol, polyethylenglycol, polyvinyl pyrrolidone, sodium chloride, potassium chloride, orange essence, strawberry essence, vanila aroma or the like. Daily dosage of the compound of the general formula(I) may be varied depending on age, sex of patient and the degree of disease. Daily dosage is 1.0 mg to 5,000 mg may be administered one to several times.

The compounds of the general formula (I) according to the present invention may be prepared by the following scheme I.

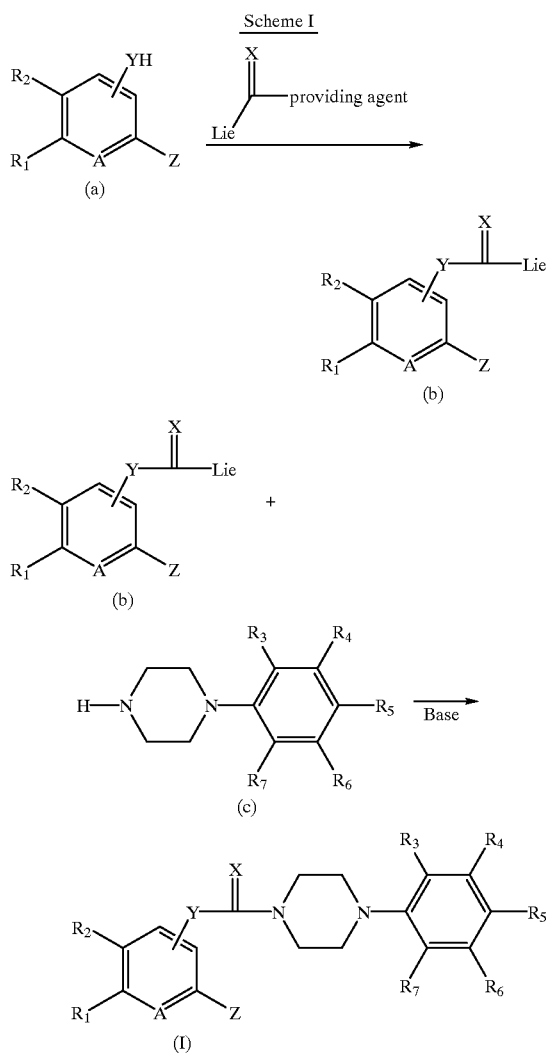

Scheme I (a)

(b)

(b) +

(c)

(I)

wherein $R_1$, $R_2$, $R_3$, $R_4$, $R_5$, $R_6$, $R_7$, A, X, Y and Z are as defined above, and Lie is a leaving group such as halogen atom, sulfonyl or the like.

The above process comprises reacting a compound of the general formula(a) with a —C(=X)— group-providing agent in organic solvent to obtain a compound of the general formula(b) and successively reacting the compound of the general formula(b) with a compound of the general formula (c) to give the compound of the general formula(I). The used —C(=X)-group-providing agent preferably be selected from 1,1-carbonyldiimidazole, 1,1-carbonylthiodiimidazole, phosgene, thiophosgene, carbonyldiphenoxide, phenylchloroformate or the like. The reaction may be carried out in conventional organic solvent such as, for example, tetrahydrofuran, dichloromethane, chloroform, acetonitrile.

And also the reaction is preferably carried out in the presence of coupling agent such as conventional inorganic or organic base. Such conventional inorganic or organic base used in the reaction means sodium hydride, potassium hydride, sodium hydroxide, potassium hydroxide, sodium carbonate, potassium carbonate, cesium carbonate, sodium bicarbonate, potassium bicarbonate, triethyvlmine, pyridine, DBU or the like, and 1–1.5 equivalent, preferably 1–1.1 equivalent thereof may be used.

The reaction may be carried out between 3° C. and boiling point of the solvent used, preferably at 50° C.–100° C. for 5–48 hours, preferably for 10–24 hours.

—C(=X)-group-providing agent may be used in an amount of 1–1.5 equivalent, preferably 1–1.1 equivalent to the stating compound.

A compound of the general formula(I) wherein Y is —$NR_8$— may be prepared by the following scheme II Scheme II

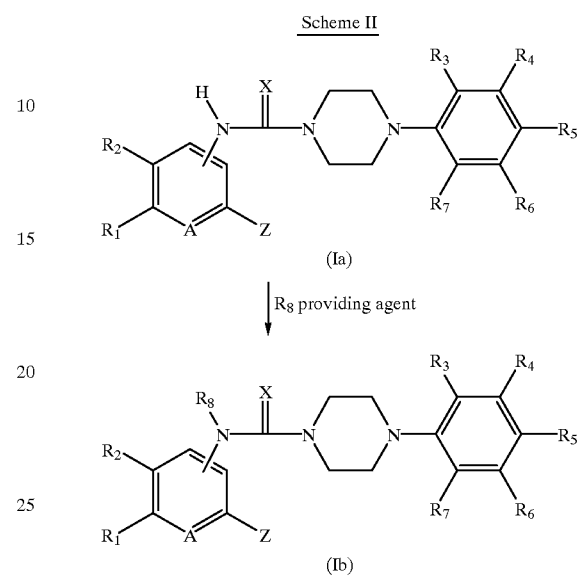

(Ia)

$R_8$ providing agent (Ib)

wherein, $R_1$, $R_2$, $R_3$, $R_4$, $R_5$, $R_6$, $R_7$, $R_8$, A, X and Z are as defined above.

A compound of the general formula(Ib) above may be prepared effectively by introducing Rg providing agent into a compound of the general formula(Ia).

$R_8$ providing agent preferably used in the above reaction is $C_1$–$C_8$ lower alkylhalogen, $C_1$–$C_8$ lower alkyl sulfonate, substituted or unsubstituted $C_3$–$C_8$ cycloalkylhalogen, arylhalogen, substituted or unsubstituted $C_3$–$C_8$ cycloalkyl sulfonate, arylsulfonate, or the like.

$C_1$–$C_8$ lower alkylhalogen means methylchloride, methylbromide, methyliodide, ethylchloride, ethylbromide, ethyliodide, propylchloride, propylbromide, propyliodide, butylchloride, butylbromide, butyliodide, ientylchloride, pentylbromide, pentyliodide, ethylbromoacetate, or the like.

$C_1$–$C_8$ lower alkyl sulfonate means methylsulfonate, ethylsulfonate, propylsulfonate, butylsulfonate, pentylsulfonate, or the like.

Substituted or unsubstituted $C_3$–$C_8$ cycloalkylhalogen means cyclopropylchloride, cyclopropylbromide, cyclopropyliodide, cyclobutylchloride, cyclobutylbromide, cyclobutyliodide, cyclopentyvlchloride, cyclopentylbromide, cyclopentyliodide, cyclohexylchloride, cyclohexylbromide, cyclohexyliodide, cyclopropyl methylchloride, cyclopropyl methylbromide, cyclopropyl methyliodide, cyclobutyl methylchloride, cyclobutyl methylbromide, cyclobutyl methyliodide, cyclopentyl methylchloride, cyclopentyl methylbromide, cyclopentyl methylchloride, cyclohexyl methylchloride, cyclohexyl methylbromide, cyclohexyl methyliodide, or the like.

Arylhalogen means benzylchloride, benzylbromide, benzyliodide, benzoylchloride, benzoylbromide, benzoyliodide, toluylchloride, toluylbromide, toluyliodide, or the like.

Substituted or unsubstituted $C_3$–$C_8$ cycloalkyl sulfonate means cyclopropyl sulfonate, cyclobutyl sulfonate, cyclopentyl sulfonate, cyclohexyl sulfonate, methylcyclopropyl sulfonate, methylcyclobutyl sulfonate, methylcyclopentyl sulfonate, methylcyclohexyl sulfonate, or the like.

Arylsulfonate means benzyl sulfonate, benzoyl sulfonate, toluyl sulfonate, or the like.

More particularly, a compound of the general formula (1a) may be reacted with an alkylating agent or arylating agent in a solvent at the temperature of 25–80° C., for 30 minutes–20 hours to give the object compound of the general formula (Ib).

An alkylating agent or arylating agent may be used in amount of 1.0–1.5 equivalent.

Conventional organic solvent such as for example tetrahydrofuran, dichloromethane, acetonitrile, dimethylformamide may be used in the above reaction.

In the above reactions, if any acid material is formed, any basic material may be preferably added as scavenger in order to eliminate the acid material from the reaction phase. Such basic material may be alkali metal hydroxide, alkali earth metal hydroxide, alkali metal oxide, alkali earth metal oxide, alkali metal carbonate, alkali earth metal carbonate, alkali metal hydrogen carbonate, alkali earth metal hydrogen carbonate such as sodium hydroxide, potassium hydroxide, calcium hydroxide, magnesium hydroxide, magnesium oxide, calcium oxide, potassium carbonate, sodium carbonate, calcium carbonate, magnesium carbonate, magnesium bicarbonate, sodium bicarbonate, calcium bicarbonate or the like, or organic amines.

The compound of the general formula(a) is described in prior art (J. Med. Chem., 1992, 35, 3784, 3792) or may be prepared in a similar method to the art.

Hereinafter the present invention will be described in more details with reference to following examples but it is not intended to limit the scope of the invention thereinto.

Compounds of the general formula(I) and formula(Ib) are prepared in following examples according to the above-mentioned process.

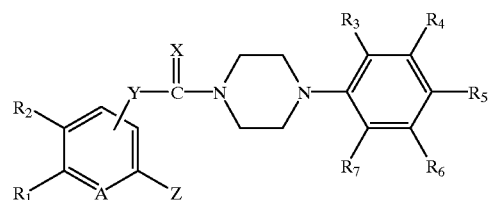

(I)

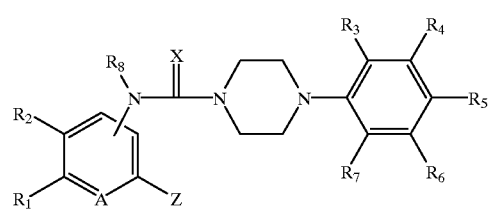

(Ib)

wherein $R_1$, $R_2$, $R_3$, $R_4$, $R_5$, $R_6$, $R_7$, A, X, Y, Z are the same above.

| Ex. No. | $R_1$ | $R_2$ | $R_3$ | $R_4$ | $R_5$ | $R_6$ | $R_7$ | A | X | Y | Z | Y |
|---|---|---|---|---|---|---|---|---|---|---|---|---|
| 1 | Me | Me | SMe | H | H | H | H | N | O | NH | OMe | 3-N |
| 2 | Me | Me | ⟩=⟨ | H | H | H | H | N | O | NH | OMe | 3-N |
| 3 | Me | Me | Me | Me | H | Me | Me | N | O | NH | OMe | 3-N |
| 4 | Me | Et | SMe | H | H | H | H | N | O | NH | OMe | 3-N |
| 5 | Me | Et | ⟩=⟨ | H | H | H | H | N | O | NH | OMe | 3-N |
| 6 | Me | Et | Me | Me | H | Me | Me | N | O | NH | OMe | 3-N |
| 7 | Me | Et | H | SH | H | H | H | N | O | NH | OMe | 3-N |
| 8 | Me | nPr | H | OMe | H | OMe | H | N | O | NH | OMe | 3-N |
| 9 | Me | nPr | H | Me | H | Me | H | N | O | NH | OMe | 3-N |
| 10 | Me | nPr | H | F | H | F | H | N | O | NH | OMe | 3-N |
| 11 | Me | nPr | OMe | H | H | H | H | N | O | NH | OMe | 3-N |
| 12 | Et | Me | H | OMe | H | OMe | H | N | O | NH | OMe | 3-N |
| 13 | Et | Me | H | Me | H | Me | H | N | O | NH | OMe | 3-N |
| 14 | Et | Me | H | OH | H | H | H | N | O | NH | OMe | 3-N |
| 15 | nPr | Me | H | OMe | H | OMe | H | N | O | NH | OMe | 3-N |
| 16 | nPr | Me | H | Me | H | Me | H | N | O | NH | OMe | 3-N |
| 17 | nPr | Me | H | OH | H | H | H | N | O | NH | OMe | 3-N |
| 18 |  | —(CH$_2$)$_3$— | H | OMe | H | OMe | H | N | O | NH | OMe | 3-N |
| 19 |  | —(CH$_2$)$_3$— | H | Me | H | Me | H | N | O | NH | OMe | 3-N |
| 20 |  | —(CH$_2$)$_4$— | H | OMe | H | OMe | H | N | O | NH | OMe | 3-N |
| 21 |  | —(CH$_2$)$_4$— | H | Me | H | Me | H | N | O | NH | OMe | 3-N |
| 22 | Me | Me | H | Me | H | Me | H | N | S | NH | OMe | 3-N |
| 23 | Me | Me | H | F | H | F | H | N | S | NH | OMe | 3-N |
| 24 | Me | Me | H | OH | H | H | H | N | S | NH | OMe | 3-N |
| 25 | Me | nPr | H | OMe | H | OMe | H | N | S | NH | OMe | 3-N |
| 26 | nPr | Me | H | OMe | H | OMe | H | N | S | NH | OMe | 3-N |
| 27 | nPr | Me | H | Me | H | Me | H | N | S | NH | OMe | 3-N |

-continued

| Ex. No. | R₁ | R₂ | R₃ | R₄ | R₅ | R₆ | R₇ | A | X | Y | Z | Y |
|---|---|---|---|---|---|---|---|---|---|---|---|---|
| 28 | nPr | Me | H | OH | H | H | H | N | S | NH | OMe | 3-N |
| 29 |  | —(CH₂)₃— | H | OMe | H | OMe | H | N | S | NH | OMe | 3-N |
| 30 |  | —(CH₂)₃— | H | Me | H | Me | H | N | S | NH | OMe | 3-N |
| 31 |  | —(CH₂)₄— | H | OMe | H | OMe | H | N | S | NH | OMe | 3-N |
| 32 |  | —(CH₂)₄— | H | Me | H | Me | H | N | S | NH | OMe | 3-N |
| 33 | Me | Me | H | OMe | H | OMe | H | N | O | NH | NHMe | 3-N |
| 34 | Me | Me | H | Me | H | Me | H | N | O | NH | NHMe | 3-N |
| 35 | Me | Et | H | Me | H | Me | H | N | O | NH | NHMe | 3-N |
| 36 |  | —(CH₂)₃— | H | OMe | H | OMe | H | N | O | NH | NHMe | 3-N |
| 37 |  | —(CH₂)₃— | H | Me | H | Me | H | N | O | NH | NHMe | 3-N |
| 38 | Me | Me | H | OMe | H | OMe | H | N | O | NH | N-piperazine-NBoc | 3-N |
| 39 | Me | Me | H | Me | H | Me | H | N | O | NH | N-piperazine-NBoc | 3-N |
| 40 | Me | Et | H | OMe | H | OMe | H | N | O | NH | N-piperazine-NBoc | 3-N |
| 41 | Me | Et | H | Me | H | Me | H | N | O | NH | N-piperazine-NBoc | 3-N |
| 42 | Me | Me | H | OMe | H | OMe | H | N | O | NH | N-piperazine-NH | 3-N |
| 43 | Me | Me | H | Me | H | Me | H | N | O | NH | N-piperazine-NH | 3-N |
| 44 | Me | Et | H | OMe | H | OMe | H | N | O | NH | N-piperazine-NH | 3-N |
| 45 | Me | Et | H | Me | H | Me | H | N | O | NH | N-piperazine-NH | 3-N |
| 46 | Me | Ac | H | OMe | H | OMe | H | N | O | NH | OMe | 3-N |
| 47 | Me | Ac | H | Me | H | Me | H | N | O | NH | OMe | 3-N |
| 48 | Me | Ac | H | F | H | F | H | N | O | NH | OMe | 3-N |
| 49 | Me | Ac | H | Cl | H | Cl | H | N | O | NH | OMe | 3-N |
| 50 | Me | Ac | Me | Me | H | H | H | N | O | NH | OMe | 3-N |
| 51 | Me | Ac | OMe | H | H | H | H | N | O | NH | OMe | 3-N |
| 52 | Me | Ac | H | OH | H | H | H | N | O | NH | OMe | 3-N |
| 53 | Me | Ac | H | OMe | H | OMe | H | N | S | NH | OMe | 3-N |
| 54 | Me | Ac | H | Me | H | Me | H | N | S | NH | OMe | 3-N |
| 55 | Me | Ac | H | OH | H | H | H | N | S | NH | OMe | 3-N |
| 56 | Me | CH(OH)(iPr) | H | OMe | H | OMe | H | N | O | NH | OMe | 3-N |
| 57 | Me | CH(OH)(iPr) | H | Me | H | Me | H | N | O | NH | OMe | 3-N |

-continued

| Ex. No. | R₁ | R₂ | R₃ | R₄ | R₅ | R₆ | R₇ | A | X | Y | Z | Y |
|---|---|---|---|---|---|---|---|---|---|---|---|---|
| 58 | Me | CH(OH)CH₃ (isopropanol) | Me | Me | H | H | H | N | O | NH | OMe | 3-N |
| 59 | Me | CH(OH)CH₃ | H | F | H | F | H | N | O | NH | OMe | 3-N |
| 60 | Me | CH(OH)CH₃ | H | Cl | H | Cl | H | N | O | NH | OMe | 3-N |
| 61 | Me | CH(OH)CH₃ | OMe | H | H | H | H | N | O | NH | OMe | 3-N |
| 62 | Me | CH(OH)CH₃ | H | OH | H | H | H | N | O | NH | OMe | 3-N |
| 63 | Me | CH(OH)CH₃ | H | OMe | H | OMe | H | N | S | NH | OMe | 3-N |
| 64 | Me | CH(OH)CH₃ | H | Me | H | Me | H | N | S | NH | OMe | 3-N |
| 65 | Me | C(OH)(CH₃)₂ | H | OMe | H | OMe | H | N | O | NH | OMe | 3-N |
| 66 | Me | C(OH)(CH₃)₂ | H | Me | H | Me | H | N | O | NH | OMe | 3-N |
| 67 | Me | C(OH)(CH₃)(CH₂CH₃) | H | OMe | H | OMe | H | N | O | NH | OMe | 3-N |
| 68 | Me | C(OH)(CH₃)(CH₂CH₃) | H | Me | H | Me | H | N | O | NH | OMe | 3-N |
| 69 | Me | CH(CH₃)SC(=O)CH₃ | H | OMe | H | OMe | H | N | O | NH | OMe | 3-N |
| 70 | Me | CH(CH₃)SC(=O)CH₃ | H | Me | H | Me | H | N | O | NH | OMe | 3-N |
| 71 | Me | CH(CH₃)SH | H | OMe | H | OMe | H | N | O | NH | OMe | 3-N |
| 72 | Me | CH(CH₃)SH | H | Me | H | Me | H | N | O | NH | OMe | 3-N |
| 73 | Me | Vinyl | H | OMe | H | OMe | H | N | O | NH | OMe | 3-N |

-continued

| Ex. No. | R₁ | R₂ | R₃ | R₄ | R₅ | R₆ | R₇ | A | X | Y | Z | Y |
|---|---|---|---|---|---|---|---|---|---|---|---|---|
| 74 | Me | Vinyl | H | Me | H | Me | H | N | O | NH | OMe | 3-N |
| 75 | Me | Vinyl | H | F | H | F | H | N | O | NH | OMe | 3-N |
| 76 | Me | isopropenyl | H | OMe | H | OMe | H | N | O | NH | OMe | 3-N |
| 77 | Me | isopropenyl | H | Me | H | Me | H | N | O | NH | OMe | 3-N |
| 78 | Me | OCH(iPr)-OCH₂COEt | H | OMe | H | OMe | H | N | O | NH | OMe | 3-N |
| 79 | Me | OCH(iPr)-OCH₂COEt | H | OMe | H | OMe | H | N | O | NH | OMe | 3-N |
| 80 | Me | OCH(iPr)-OCH₂COEt | H | Me | H | Me | H | N | O | NH | OMe | 3-N |

| Ex. No. | R₁ and R₂ | R₃ | R₄ | R₅ | R₆ | R₇ | R₈ | A | X | Z | Y |
|---|---|---|---|---|---|---|---|---|---|---|---|
| 81 | —CH=CH—CH=CH— | H | OMe | H | OMe | H | H | N | O | OMe | 3-N |
| 82 | —CH=CH—CH=CH— | H | Me | H | Me | H | H | N | O | OMe | 3-N |
| 83 | —CH=CH—CH=CH— | Me | Me | H | H | H | H | N | O | OMe | 3-N |
| 84 | —CH=CH—CH=CH— | H | F | H | F | H | H | N | O | OMe | 3-N |
| 85 | —CH=CH—CH=CH— | H | Cl | H | Cl | H | H | N | O | OMe | 3-N |
| 86 | —CH=CH—CH=CH— | F | H | H | H | H | H | N | O | OMe | 3-N |
| 87 | —CH=CH—CH=CH— | Cl | H | H | H | H | H | N | O | OMe | 3-N |
| 88 | —CH=CH—CH=CH— | H | Cl | H | H | H | H | N | O | OMe | 3-N |
| 89 | —CH=CH—CH=CH— | H | OH | H | H | H | H | N | O | OMe | 3-N |
| 90 | —CH=CH—CH=CH— | OMe | H | H | H | H | H | N | O | OMe | 3-N |
| 91 | —CH=CH—CH=CH— | SMe | H | H | H | H | H | N | O | OMe | 3-N |
| 92 | —CH=CH—CH=CH— | H | O-iPr | H | H | H | H | N | O | OMe | 3-N |
| 93 | —CH=CH—CH=CH— | H | OCH₂-cyclopropyl | H | H | H | H | N | O | OMe | 3-N |
| 94 | —CH=CH—CH=CH— | OMe | H | H | Me | H | H | N | O | OMe | 3-N |
| 95 | —CH=CH—CH=CH— | OMe | H | H | Ph | H | H | N | O | OMe | 3-N |
| 96 | —CH=CH—CH=CH— | Me | H | H | OMe | H | H | N | O | OMe | 3-N |
| 97 | —CH=CH—CH=CH— | —Benzo— | | H | H | H | H | N | O | OMe | 3-N |
| 98 | —CH=CH—CH=CH— | H | OMe | H | OMe | H | Me | N | O | OMe | 3-N |
| 99 | —CH=CH—CH=CH— | H | OMe | H | OMe | H | Et | N | O | OMe | 3-N |
| 100 | —CH=CH—CH=CH— | H | OMe | H | OMe | H | iPr | N | O | OMe | 3-N |
| 101 | —CH=CH—CH=CH— | H | OMe | H | OMe | H | CH₂-cyclopropyl | N | O | OMe | 3-N |
| 102 | —CH=CH—CH=CH— | H | OMe | H | OMe | H | Benzyl | N | O | OMe | 3-N |

-continued

| Ex. No. | R₁ and R₂ | R₃ | R₄ | R₅ | R₆ | R₇ | R₈ | A | X | Z | Y |
|---|---|---|---|---|---|---|---|---|---|---|---|
| 103 | —CH=CH—CH=CH— | H | Me | H | Me | H | Me | N | O | OMe | 3-N |
| 104 | —CH=CH—CH=CH— | H | Me | H | Me | H | Et | N | O | OMe | 3-N |
| 105 | —CH=CH—CH=CH— | H | Me | H | Me | H | iPr | N | O | OMe | 3-N |
| 106 | —CH=CH—CH=CH— | H | Me | H | Me | H | Benzyl | N | O | OMe | 3-N |
| 107 | —CH=CH—CH=CH— | H | O—CH(CH₃)₂ | H | H | H | Me | N | O | OMe | 3-N |
| 108 | —CH=CH—CH=CH— | H | O—CH(CH₃)₂ | H | H | H | Et | N | O | OMe | 3-N |
| 109 | —CH=CH—CH=CH— | H | OMe | H | OMe | H | H | N | S | OMe | 3-N |
| 110 | —CH=CH—CH=CH— | H | Me | H | Me | H | H | N | S | OMe | 3-N |
| 111 | —CH=CH—CH=CH— | H | F | H | F | H | H | N | S | OMe | 3-N |
| 112 | —CH=CH—CH=CH— | H | Cl | H | Cl | H | H | N | S | OMe | 3-N |
| 113 | —CH=CH—CH=CH— | H | OMe | H | H | H | H | N | S | OMe | 3-N |
| 114 | —CH=CH—CH=CH— | H | OMe | H | OMe | H | H | N | O | Me | 3-N |
| 115 | —CH=CH—CH=CH— | H | Me | H | Me | H | H | N | O | Me | 3-N |
| 116 | —CH=CH—CH=CH— | Me | Me | H | H | H | H | N | O | Me | 3-N |
| 117 | —CH=CH—CH=CH— | H | F | H | F | H | H | N | O | Me | 3-N |
| 118 | —CH=CH—CH=CH— | H | Cl | H | Cl | H | H | N | O | Me | 3-N |
| 119 | —CH=CH—CH=CH— | OMe | H | H | H | H | H | N | O | Me | 3-N |
| 120 | —CH=CH—CH=CH— | F | H | H | H | H | H | N | O | Me | 3-N |
| 121 | —CH=CH—CH=CH— | Cl | H | H | H | H | H | N | O | Me | 3-N |
| 122 | —CH=CH—CH=CH— | SMe | H | H | H | H | H | N | O | Me | 3-N |
| 123 | —CH=CH—CH=CH— | OMe | H | H | Me | H | H | N | O | Me | 3-N |
| 124 | —CH=CH—CH=CH— |  | —Benzo— | H | H | H | H | N | O | Me | 3-N |
| 125 | —CH=CH—CH=CH— | H | OMe | H | OMe | H | H | N | S | Me | 3-N |
| 126 | —CH=CH—CH=CH— | H | Me | H | Me | H | H | N | S | Me | 3-N |
| 127 | —CH=CH—CH=CH— | H | F | H | F | H | H | N | S | Me | 3-N |
| 128 | —CH=CH—CH=CH— | H | OMe | H | OMe | H | H | N | O | 2-Py | 4-N |
| 129 | —CH=CH—CH=CH— | H | OMe | H | OMe | H | H | N | O | 3-Py | 4-N |
| 130 | —CH=CH—CH=CH— | H | OMe | H | OMe | H | H | N | O | 2-Thienyl | 4-N |
| 131 | —CH=CH—CH=CH— | H | Me | H | Me | H | H | N | O | 3-Py | 4-N |

| Ex. No. | R₁ | R₂ | R₃ | R₄ | R₅ | R₆ | R₇ | R₈ | A | X | Z | Y |
|---|---|---|---|---|---|---|---|---|---|---|---|---|
| 132 | Me | Me | H | OMe | H | OMe | H | Me | N | O | OMe | 3-N |
| 133 | Me | Me | H | OMe | H | OMe | H | Et | N | O | OMe | 3-N |
| 134 | Me | Me | H | OMe | H | OMe | H | i-Pr | N | O | OMe | 3-N |
| 135 | Me | Me | H | Me | H | Me | H | Me | N | O | OMe | 3-N |
| 136 | Me | Me | OMe | H | H | H | H | Me | N | O | OMe | 3-N |
| 137 | Me | Me | OMe | H | H | H | H | Et | N | O | OMe | 3-N |
| 138 | Me | Me | OMe | H | H | H | H | Bn | N | O | OMe | 3-N |
| 139 | Me | Me | OMe | H | H | H | H | CH₂-cyclopropyl | N | O | OMe | 3-N |
| 140 | Me | Me | Me | H | H | OMe | H | Me | N | O | OMe | 3-N |
| 141 | Me | Me | Me | H | H | OMe | H | Et | N | O | OMe | 3-N |
| 142 | Me | Me | Me | H | H | OMe | H | Bn | N | O | OMe | 3-N |
| 143 | Me | Et | H | OMe | H | OMe | H | Me | N | O | OMe | 3-N |
| 144 | Me | Et | H | Me | H | Me | H | Me | N | O | OMe | 3-N |
| 145 | Me | Et | H | Me | H | Me | H | Et | N | O | OMe | 3-N |
| 146 | Me | nPr | H | OMe | H | OMe | H | Me | N | O | OMe | 3-N |
| 147 | Et | Me | H | OMe | H | OMe | H | Me | N | O | OMe | 3-N |
| 148 | nPr | Me | H | OMe | H | OMe | H | Me | N | O | OMe | 3-N |
| 149 | Me | Ac | H | OMe | H | OMe | H | Me | N | O | OMe | 3-N |
| 150 | Me | Ac | H | OMe | H | OMe | H | Et | N | O | OMe | 3-N |
| 151 | Me | Ac | H | Me | H | Me | H | Me | N | O | OMe | 3-N |
| 152 | Me | C(CH₃)₂OH | H | OMe | H | OMe | H | Me | N | O | OMe | 3-N |

-continued

| Ex. No. | R₁ | R₂ | R₃ | R₄ | R₅ | R₆ | R₇ | R₈ | A | X | Z | Y |
|---|---|---|---|---|---|---|---|---|---|---|---|---|
| 153 | Me | CH(OH)(CH₃)₂ (isopropanol) | H | OMe | H | OMe | H | Et | N | O | OMe | 3-N |
| 154 | Me | CH(OH)(CH₃)₂ | H | Me | H | Me | H | Me | N | O | OMe | 3-N |
| 155 | Me | C(OH)(CH₃)₃ (tert-butanol) | H | OMe | H | OMe | H | Me | N | O | OMe | 3-N |
| 156 | Me | C(OH)(CH₃)(CH₂CH₃) | H | Me | H | Me | H | Me | N | O | OMe | 3-N |
| 157 | Me | CH(OCH₃)(CH₃)₂ | H | OMe | H | OMe | H | Me | N | O | OMe | 3-N |
| 158 | Me | Vinyl | H | OMe | H | OMe | H | Me | N | O | OMe | 3-N |
| 159 | Me | Vinyl | H | Me | H | Me | H | Me | N | O | OMe | 3-N |
| 160 | Me | Vinyl | H | OMe | H | OMe | H | Et | N | O | OMe | 3-N |
| 161 | Me | C(=CH₂)CH₃ (isopropenyl) | H | OMe | H | OMe | H | Me | N | O | OMe | 3-N |
| 162 | Me | C(=CH₂)CH₃ | H | Me | H | Me | H | Me | N | O | OMe | 3-N |
| 163 | Me | Ac | H | OMe | H | OMe | H | CH₂C(O)OEt | N | O | OMe | 3-N |
| 164 | Me | Ac | H | Me | H | Me | H | CH₂C(O)OEt | N | O | OMe | 3-N |
| 165 | Me | Ac | H | OMe | H | OMe | H | CH₂C(O)OH | N | O | OMe | 3-N |
| 166 | Me | CH(OH)(CH₃)₂ | H | OMe | H | OMe | H | CH₂C(O)OEt | N | O | OMe | 3-N |
| 167 | Me | CH(OH)(CH₃)₂ | H | OMe | H | OMe | H | CH₂C(O)OH | N | O | OMe | 3-N |
| 168 | Me | CH(OH)(CH₃)₂ | H | Me | H | Me | H | CH₂C(O)OEt | N | O | OMe | 3-N |
| 169 | Me | CH(OH)(CH₃)₂ | H | Me | H | Me | H | CH₂C(O)OH | N | O | OMe | 3-N |
| 170 | Me | Me | H | H | H | H | H | H | CH | O | OMe | 3-N |
| 171 | Me | Me | H | OMe | H | OMe | H | H | CH | O | OMe | 3-N |
| 172 | Me | Me | H | Me | H | Me | H | H | CH | O | OMe | 3-N |

-continued

| Ex. No. | R₁ | R₂ | R₃ | R₄ | R₅ | R₆ | R₇ | R₈ | A | X | Z | Y |
|---|---|---|---|---|---|---|---|---|---|---|---|---|
| 173 | Me | Me | Me | Me | H | H | H | H | CH | O | OMe | 3-N |
| 174 | Me | Me | Me | Me | H | Me | Me | H | CH | O | OMe | 3-N |
| 175 | Me | Me | H | F | H | F | H | H | CH | O | OMe | 3-N |
| 176 | Me | Me | Cl | H | H | H | H | H | CH | O | OMe | 3-N |
| 177 | Me | Me | H | Cl | H | H | H | H | CH | O | OMe | 3-N |
| 178 | Me | Me | OH | H | H | H | H | H | CH | O | OMe | 3-N |
| 179 | Me | Me | H | OH | H | H | H | H | CH | O | OMe | 3-N |
| 180 | Me | Me | H | SH | H | H | H | H | CH | O | OMe | 3-N |
| 181 | Me | Me | OAc | H | H | H | H | H | CH | O | OMe | 3-N |
| 182 | Me | Me | H | OAc | H | H | H | H | CH | O | OMe | 3-N |
| 183 | Me | Me | OMe | H | H | H | H | H | CH | O | OMe | 3-N |
| 184 | Me | Me | H | Me | H | H | OMe | H | CH | O | OMe | 3-N |
| 185 | Me | Me | H | OMe | H | H | Me | H | CH | O | OMe | 3-N |
| 186 | Me | Me | H | OMe | H | H | Ph | H | CH | O | OMe | 3-N |
| 187 | Me | Me | isopropenyl | H | H | H | H | H | CH | O | OMe | 3-N |
| 188 | Me | Me | Benzo | | H | H | H | H | CH | O | OMe | 3-N |
| 189 | Me | Me | Naphto | | H | H | H | H | CH | O | OMe | 3-N |
| 190 | Me | Me | H | OMe | H | OMe | H | Me | CH | O | OMe | 3-N |
| 191 | Me | Me | H | Me | H | Me | H | Me | CH | O | OMe | 3-N |
| 192 | Me | Me | H | F | H | F | H | Me | CH | O | OMe | 3-N |
| 193 | Me | Me | H | OMe | H | OMe | H | Et | CH | O | OMe | 3-N |
| 194 | Me | Me | H | Me | H | Me | H | Et | CH | O | OMe | 3-N |
| 195 | Me | Me | H | F | H | F | H | Et | CH | O | OMe | 3-N |
| 196 | Me | Me | H | F | H | F | H | iPr | CH | O | OMe | 3-N |
| 197 | Me | Me | H | OMe | H | OMe | H | H | CH | S | OMe | 3-N |
| 198 | Me | Me | H | Me | H | Me | H | H | CH | S | OMe | 3-N |
| 199 | Me | Me | Me | Me | H | H | H | H | CH | S | OMe | 3-N |
| 200 | Me | Me | H | F | H | F | H | H | CH | S | OMe | 3-N |
| 201 | Me | Me | H | Cl | H | Cl | H | H | CH | S | OMe | 3-N |
| 202 | Me | Me | F | H | H | H | H | H | CH | S | OMe | 3-N |
| 203 | Me | Me | Cl | H | H | H | H | H | CH | S | OMe | 3-N |
| 204 | Me | Me | OMe | H | H | H | H | H | CH | S | OMe | 3-N |
| 205 | Me | Me | SMe | H | H | H | H | H | CH | S | OMe | 3-N |
| 206 | Me | Me | H | OH | H | H | H | H | CH | S | OMe | 3-N |
| 207 | Me | Me | OPh | H | H | H | H | H | CH | S | OMe | 3-N |
| 208 | Me | Me | isopropenyl | H | H | H | H | H | CH | S | OMe | 3-N |
| 209 | Me | Me | H | OMe | H | H | Me | H | CH | S | OMe | 3-N |
| 210 | Me | Me | Benzo | | H | H | H | H | CH | S | OMe | 3-N |
| 211 | Me | Acetyl | H | OMe | H | OMe | H | H | CH | O | OMe | 3-N |
| 212 | Me | Acetyl | H | Me | H | Me | H | H | CH | O | OMe | 3-N |
| 213 | Me | Acetyl | H | Cl | H | Cl | H | H | CH | O | OMe | 3-N |
| 214 | Me | 2-hydroxyprop-2-yl | H | OMe | H | OMe | H | H | CH | O | OMe | 3-N |
| 215 | Me | 2-hydroxyprop-2-yl | H | Me | H | Me | H | H | CH | O | OMe | 3-N |
| 216 | Me | Vinyl | H | OMe | H | OMe | H | H | CH | O | OMe | 3-N |
| 217 | Me | Vinyl | H | Me | H | Me | H | H | CH | O | OMe | 3-N |
| 218 | Me | Acetyl | H | OMe | H | OMe | H | H | CH | S | OMe | 3-N |
| 219 | Me | Acetyl | H | Me | H | Me | H | H | CH | S | OMe | 3-N |
| 220 | Me | Acetyl | H | Cl | H | Cl | H | H | CH | S | OMe | 3-N |
| 221 | Me | 2-hydroxyprop-2-yl | H | OMe | H | OMe | H | H | CH | S | OMe | 3-N |

-continued

| Ex. No. | R$_1$ | R$_2$ | R$_3$ | R$_4$ | R$_5$ | R$_6$ | R$_7$ | R$_8$ | A | X | Z | Y |
|---|---|---|---|---|---|---|---|---|---|---|---|---|
| 222 | Me | OH-C(Me)$_2$- | H | Me | H | Me | H | H | CH | S | OMe | 3-N |
| 223 | Me | OH-C(Me)$_2$- | H | Cl | H | Cl | H | H | CH | S | OMe | 3-N |
| 224 | Me | Me | H | OMe | H | OMe | H | CH$_2$COEt (C=O) | CH | O | OMe | 3-N |
| 225 | Me | Me | H | Me | H | Me | H | CH$_2$COEt (C=O) | CH | O | OMe | 3-N |
| 226 | Me | Me | H | OMe | H | OMe | H | CH$_2$COH (C=O) | CH | O | OMe | 3-N |
| 227 | Me | Me | H | Me | H | Me | H | CH$_2$COH (C=O) | CH | O | OMe | 3-N |
| 228 | Me | Me | H | OMe | H | OMe | H | H | CH | O | OH | 3-N |
| 229 | Me | Me | H | Me | H | Me | H | H | CH | O | OH | 3-N |
| 230 | Me | Me | H | F | H | F | H | H | CH | O | OH | 3-N |
| 231 | Me | Me | H | Cl | H | Cl | H | H | CH | O | OH | 3-N |

EXAMPLE 1

1-[(5,6-Dimethyl-2-methoxypyridin-3-yl)aminocarbonyl]-4-(2-methylthiophenyl)piperazine a) Phenyl N-(5,6-dimethyl-2-methoxypyridin-3-yl) carbamate 3-Amino-5,6-dimethyl-2-methoxypyridine(1.52 g, 0.01 mol) and phenylchloroformate(1.56 g, 0.01 mol) were dissolved in dichloromethane and was stirred at room temperature for 2 hours. The mixture was concentrated under the reduced pressure to remove the solvent. The concentrate was purified by column chromatography(ethylacetate:hexane= 1:6) to obtain the titled compound.

yield: 92%

$^1$H-NMR(CDCl$_3$) δ: 2.18(3H,s), 2.36(3H,s), 4.00(3H,s), 7.31(5H,m), 8.07(1H,s)

b) 1-[(5,6-Dimethyl-2-methoxypyridin-3-yl)aminocarbonyl]-4-(2-methylthiolphenyl)piperazine Phenyl N-(5,6-dimethyl-2-methoxypyridin-3-yl) carbamate(136 mg, 0.5 mmol) and 1-(2-methylthiophenyl)piperazine(104 mg, 0.5 mmol) were dissolved in anhydrous tetrahydrofuran and DBU(76 mg, 0.5 mmol) was added. The mixture was stirred at room temperature for 2 hours and concentrated under the reduced pressure to remove tetrahydrofuran. The concentrate was purified by column chromatography(ethylacetate:hexane=1:2) to obtain the titled compound.

yield: 59% m.p.: 167–169° C.

$^1$H NMR(CDCl$_3$) δ: 2.21(3H,s), 2.43(6H,s), 3.06(4H,t), 3.68(4H,t), 4.09(3H,s), 6.89(1H,s), 7.06(1H,m), 7.14(3H,s), 8.26(1H,s)

EXAMPLE 2

1-[(5,6-Dimethyl-2-methoxypyridin-3-yl)aminocarbonyl]-4-(2-isopropenylphenyl)piperazine Phenyl N-(5,6-dimethyl-2-methoxypyridin-3-yl) carbamate and 1-(2-isopropenylphenyl)piperazine were reacted by the same way with the example 1 to obtain the titled compound.

yield: 62% m.p.: 139–140° C.

$^1$H NMR(CDCl$_3$) δ: 2.20(3H,s), 2.21(6H,s), 3.10(4H,t), 3.64(4H,t), 3.84(3H,s), 5.07(1H,s), 5.13(1H,s), 6.64(1H,s), 6.98(1H,s), 7.04(3H,dd), 7.18(1H,d), 7.91(1H,s)

EXAMPLE 3

1-[(5,6-Dimethyl-2-methoxypyridin-3-yl)aminocarbonyl]-4-(2,3,5,6-tetramethylphenyl)piperazine Phenyl N-(5,6-dimethyl-2-methoxypyridin-3-yl) carbamate and 1-(2,3,5,6-tetramethylphenyl)piperazine were reacted by the same way with the example 1 to obtain the titled compound.

yield: 71% m.p.: 190–192° C.

$^1$H NMR(CDCl$_3$) δ: 2.21(15H,s), 2.42(3H,s), 3.17(4H,t), 3.61(4H,t), 4.08(3H,s), 6.84(1H,s), 6.89(1H,s), 8.26(1H,s)

EXAMPLE 4

1-[(5-Ethyl-6-methyl-2-methoxypyridin-3-yl)aminocarbonyl]-4-(2-methylthiophenyl)piperazine Phenyl N-(5-ethyl-6-methyl-2-methoxypyridin-3-yl) carbamate and 1-(2-methylthiophenyl)piperazine were reacted by the same way with the example 1 to obtain the titled compound.

yield: 56% m.p.: 160–161° C.

$^1$H NMR(CDCl$_3$) δ: 1.19(3H,t), 2.43(3H,s), 2.50(3H,s), 2.58(2H,q), 3.07(4H,t), 3.69(4H,t), 4.15(3H,s), 6.93(1H,s), 7.06(1H,m), 7.14(3H,m), 8.35(1H,s)

Mass(EI) m/z: Calcd for C$_{21}$H$_{28}$N$_4$O$_2$ 400.1932, found 400.1925

EXAMPLE 5

1-[(5-Ethyl-6-methyl-2-methoxypyridin-3-yl) aminocarbonyl]-4-(2-isopropenylphenyl)piperazine Phenyl N-(5-ethyl-6-methyl-2-methoxypyridin-3-yl) carbamate and 1-(2-isopropenylphenyl)piperazine were reacted by the same way with the example 1 to obtain the titled compound.

yield: 51% m.p.: 185–187° C.

$^1$H NMR(CDCl$_3$) δ: 1.18(3H,t), 2.21(3H,s), 2.42(3H,s), 2.56(2H,q), 3.08(4H,t), 3.62(4H,t), 4.03(3H,s), 5.08(1H,s), 5.13(1H,s), 6.90(1H,s), 7.02(3H,m), 7.18(1H,d), 8.25(1H,s)

EXAMPLE 6

1-[(5-Ethyl-2-methoxy-6-methylpyridin-3-yl) aminocarbonyl]-4-(2,3,5,6-tetramethylphenyl) piperazine Phenyl N-(5-ethyl-2-methoxy-6-methylpyridin-3-yl) carbamate and 1-(2,3,5,6-tetramethylphenyl)piperazine were reacted by the same way with the example 1 to obtain the titled compound.

yield: 69% m.p.: 176–177° C.

$^1$H NMR(CDCl$_3$) δ: 1.19(3H,t), 2.21(12H,s), 2.44(3H,s), 2.57(2H,q), 3.17(4H,t), 3.62(4H,t), 4.06(3H,s), 6.84(1H,s), 6.92(1H,s), 8.30(1H,s)

EXAMPLE 7

1-[(5-Ethyl-2-methoxy-6-methylpyridin-3-yl) aminocarbonyl]-4-(3-thiophenyl)piperazine Phenyl N-(5-ethyl-2-methoxy-6-methylpyridin-3-yl) carbamate and 1-(3-thiophenyl)piperazine were reacted by the same way with the example 1 to obtain the titled compound.

yield: 63% m.p.: 108–110° C.

$^1$H NMR(CDCl$_3$) δ: 1.17(3H,t), 2.37(3H,s), 2.49(2H,), 3.28(4H,t), 3.60(4H,t), 3.98(3H,s), 6.87(4H,m), 6.98(1H,s), 8.18(1H,s)

EXAMPLE 8

1-[(2-Methoxy-6-methyl-5-propylpyridin-3-yl) aminocarbonyl]-4- (3,5-dimethoxyphenyl)piperazine Phenyl N-(2-methoxy-6-methyl-5-propylpyridin-3-yl) carbamate and 1-(3,5-dimethoxyphenyl)piperazine were reacted by the same way with the example 1 to obtain the titled compound.

yield: 67% m.p.: 82–84° C.

$^1$H NMR(CDCl$_3$) δ: 0.94(3H,t), 1.58(2H,m), 2.37(3H,s), 2.49(2H,q), 3.25(4H,t), 3.66(4H,t), 3.78(6H,s), 3.99(3H,s), 6.07(3H,m), 6.88(1H,s), 8.16(1H,s)

Mass(EI) m/z: Calcd for C$_{23}$H$_{32}$N$_4$O$_1$ 428.2423, found 428.2447

EXAMPLE 9

1-[(2-Methoxy-6-methyl-5-propylpyridin-3-yl) aminocarbonyl]-4-(3,5-dimethylphenyl)piperazine Phenyl N-(2-methoxy-6-methyl-5-propylpyridin-3-yl) carbamate and 1-(3,5-dimethylphenyl)piperazine were reacted by the same way with the example 1 to obtain the titled compound.

yield: 64% m.p.: 145–146° C.

$^1$H NMR(CDCl$_3$) δ: 0.95(3H,t), 1.59(2H,m), 2.29(6H,s), 2.41(3H,s), 2.49(2H,q), 3.24(4H,t), 3.67(4H,t), 3.98(3H,s), 6.59(3H,m), 6.89(1H,s), 8.17(1H,s)

Mass(EI) m/z: Calcd for C$_{23}$H$_{32}$N$_4$O$_4$ 428.2423, found 428.2385

EXAMPLE 10

1-[(2-Methoxy-6-methyl-5-propylpyridin-3-yl) aminocarbonyl]-4-(3,5-difluorophenyl)piperazine Phenyl N-(2-methoxy-6-methyl-5-propylpyridin-3-yl) carbamate and 1-(3,5-difluorophenyl)piperazine were reacted by the same way with the example 1 to obtain the titled compound.

yield: 57% m.p.: 121–123° C.

$^1$H NMR(CDCl$_3$) δ: 0.95(3H,t), 1.59(2H,m), 2.38(3H,s), 2.50(2H,q), 3.29(3H,t), 3.66(3H,t), 4.00(3H,s), 6.28(1H,m), 6.36(2H,d), 6.87(1H,s), 8.17(1H,s)

EXAMPLE 11

1-[(2-Methoxy-6-methyl-5-propylpyridin-3-yl) aminocarbonyl]-4-(2-methoxyphenyl)piperazine Phenyl N-(2-methoxy-6-methyl-5-propylpyridin-3-yl) carbamate and 1-(2-methoxyphenyl)piperazine were reacted by the same way with the example 1 to obtain the titled compound.

yield: 71% m.p.: 109–110° C.

$^1$H NMR(CDCl$_3$) δ: 0.95(3H,t), 1.59(2H,m), 2.37(3H,s), 2.49(2H,q), 3.12(4H,t), 3.70(4H,t), 3.89(3H,s), 3.97(3H,s), 6.91 (4H,m), 6.95(1H,s), 8.19(1H,s)

EXAMPLE 12

1-[(6-Ethyl-2-methoxy-5-methylpyridin-3-yl) aminocarbonyl]-4-(3,5-dimethoxyphenyl)piperazine Phenyl N-(6-ethyl-2-methoxy-5-methylpyridin-3-yl) carbamate and 1-(3,5-dimethoxyphenyl)piperazine were reacted by the same way with the example 1 to obtain the titled compound.

yield: 65% m.p.: 115–116° C.

$^1$H NMR(CDCl$_3$) δ: 1.21(3H,t), 2.21(3H,s), 2.65(2H,q), 3.27(4H,t), 3.64(4H,t), 3.79(6H,s), 3.98(3H,s), 6.09(3H,m), 6.86(1H,s), 8.12(1H,s)

Mass(EI) m/z: Calcd for $C_{22}H_{30}N_4O_4$ 414.2267, found 414.2240

EXAMPLE 13

1-[(6-Ethyl-2-methoxy-5-methylpyridin-3-yl)aminocarbonyl]-4-(3,5-dimethylphenyl)piperazine Phenyl N-(6-ethyl-2-methoxy-5-methylpyridin-3-yl)carbamate and 1-(3,5-dimethylphenyl)piperazine were reacted by the same way with the example 1 to obtain the titled compound.

yield: 61% m.p.: 135–136° C.

$^1$H NMR(CDCl$_3$) δ: 1.22(3H,t), 2.21(3H,s), 2.29(6H,s), 2.65(2H,q), 3.24(4H,t), 3.66(4H,t), 3.98(3H,s), 6.59(3H,m), 6.87(1H,s), 8.12(1H,s)

Mass(EI) m/z: Calcd for $C_{22}H_{30}N_4O_2$ 382.2368, found 382.2376

EXAMPLE 14

1-[(6-Ethyl-2-methoxy-5-methylpyridin-3-yl)aminocarbonyl]-4-(3-hydroxyphenyl)piperazine Phenyl N-(6-ethyl-2-methoxy-5-methylpyridin-3-yl)carbamate and 1-(3-hydroxyphenyl)piperazine were reacted by the same way with the example 1 to obtain the titled compound.

yield: 56% m.p.: 168–170° C.

hu 1H NMR(CDCl$_3$) δ: 1.21(3H,t), 2.20(2H,s), 2.63(2H,t), 3.28(4H,t), 3.68(4H,t), 3.98(3H,s), 6.41(1H,d), 6.55(1H,d), 6.84(1H,m), 6.87(1H,s), 7.13(1H,t), 8.10(1H,s)

Mass(EI) m/z: Calcd for $C_{22}H_{26}N_4O_3$ 370.2004, found 370.1992

EXAMPLE 15

1-[(2-Methoxy-5-methyl-6-propylpyridin-3-yl)aminocarbonyl]-4-(3,5-dimethoxyphenyl)piperazine Phenyl N-(2-methoxy-5-methyl-6-propylpyridin-3-yl)carbamate and 1-(3,5-dimethoxyphenyl)piperazine were reacted by the same way with the example 1 to obtain the titled compound.

yield: 57% m.p: 121–122° C.

$^1$H NMR(CDCl$_3$) δ: 0.96(3H,t), 1.67(2H,m), 2.21(3H,s), 2.58(2H,t), 3.26(4H,t), 3.68(4H,t), 3.79(6H,s), 3.97(3H,s), 6.14(3H,m), 6.89(1H,s), 8.11(1H,s)

Mass(EI) m/z: Calcd for $C_{23}H_{32}N_4O_4$ 428.2423, found 428.2423

EXAMPLE 16

1-[(2-Methoxy-5-methyl-6-propylpyridin-3-yl)aminocarbonyl]-4-(3,5-dimethylphenyl)piperazine Phenyl N-(2-methoxy-5-methyl-6-propylpyridin-3-yl)carbamate and 1-(3,5-dimethylphenyl)piperazine were reacted by the same way with the example 1 to obtain the titled compound.

yield: 54% m.p.: 138–139° C.

$^1$H NMR(CDCl$_3$) δ: 0.96(3H,t), 1.72(2H,m), 2.21(6H,s), 2.30(3H,s), 2.59(2H,t), 3.28(4H,t), 3.76(4H,t), 3.97(3H,s), 6.70(3H,m), 6.87(1H,s), 8.11(1H,s)

Mass(EI) m/z: Calcd for $C_{23}H_{32}N_4O_2$ 396.2525, found 396.2432

EXAMPLE 17

1-[(2-Methoxy-5-methyl-6-propylpyridin-3-yl)aminocarbonyl]-4-(3-hydroxyphenyl)piperazine Phenyl N-(2-methoxy-5-methyl-6-propylpyridin-3-yl)carbamate and 1-(3-hydroxyphenyl)piperazine were reacted by the same way with the example 1 to obtain the titled compound.

yield: 52% m.p.: 153–155° C.

$^1$H NMR(CDCl$_3$) δ: 0.95(3H,t), 1.69(2H,m), 2.19(3H,s), 2.59(2H,t), 3.22(4H,t), 3.68(4H,t), 3.97(3H,s), 6.42(1H,d), 6.52(1H,d), 6.87(1H,s), 7.12(1H,t), 8.09(1H,s)

Mass(EI) m/z: Calcd for $C_{21}H_{28}N_4O_3$ 384.2161, found 384.2153

EXAMPLE 18

1-[N-(2-Methoxy-6,7-dihydro-5H-cyclopenta[b]pyridin-3-yl)aminocarbonyl]-4-(3,5-dirnethoxyphenyl)piperazine Phenyl N-(2-methoxy-6,7-dihydro-5H-cyclopenta[b]pyridin-3-yl)carbamate and 1-(3,5-dimethoxyphenyl)piperazine were reacted by the same way with the example 1 to obtain the titled compound.

yield: 59% m.p.: 143–144° C.

$^1$H NMR(CDCl$_3$) δ: 2.10(2H,m), 2.87(4H,m), 3.12(4H,t), 3.70(4H,t), 3.78(6H,s), 4.00(3H,s), 6.08(3H,m), 6.90(1H,s), 8.24(1H,s)

EXAMPLE 19

1-[N-(2-Methoxy-6,7-dihydro-5H-cyclopenta[b]pyridin-3-yl)aminocarbonyl]-4-(3,5-dimethylphenyl)piperazine Phenyl N-(2-methoxy-6,7-dihydro-5H-cyclopenta[b]pyridin-3-yl)carbamate and 1-(3,5-dimethylphenyl)piperazine were reacted by the same way with the example 1 to obtain the titled compound.

yield: 55% m.p.: 183–185° C.

$^1$H NMR(CDCl$_3$) δ: 2.08(2H,m), 2.28(6H,s), 2.87(4H,m), 3.22(4H,t), 3.67(4H,t), 4.00(3H,s), 6.57(3H,m), 6.89(1H,s), 8.24(1H,s)

EXAMPLE 20

1-[(2-Methoxy-5,6,7,8-tetrahydroquinolin-3-yl)aminocarbonyl]-4-(3,5-dimethoxyphenyl)piperazine Phenyl N-(2-methoxy-5,6,7,8-tetrahydroquinoline-3-yl)carbamate and 1-(3,5-dimethoxyphenyl)piperazine were reacted by the same way with the example 1 to obtain the titled compound.

yield: 54% m.p.: 161–163° C.

$^1$H NMR(CDCl$_3$) δ: 1.75(2H,m), 1.84(2H,m), 2.67(2H,t), 2.73(2H,t), 3.27(4H,t), 3.71(4H,t), 3.79(6H,s), 3.97(3H,s), 6.10(3H,m), 6.90(1H,s), 8.07(1H,s)

EXAMPLE 21

1-[(2-Methoxy-5,6,7,8-tetrahydroquinolin-3-yl)aminocarbonyl]-4-(3,5-dimethyphenyl)piperazine Phenyl N-(2-methoxy-5,6,7,8-tetrahydroquinolin-3-yl)carbamate and 1-(3,5-dimethylphenyl)piperazine were reacted by the same way with the example 1 to obtain the titled compound.

yield: 51% m.p.: 143–144° C.

$^1$H NMR(CDCl$_3$) δ: 1.75(2H,m), 1.84(2H,m), 2.30(6H,s), 2.68(2H,t), 2.72(2H,t), 3.26(4H,t), 3.67(4H,t), 3.97(3H,s), 6.61(3H,m), 6.91(1H,s), 8.07(1H,s)

EXAMPLE 22

1-[(5,6-Dimethyl-2-methoxypyridin-3-yl) aminothiocarbonyl]-4-(3,5-dimethylphenyl) piperazine Phenyl N-(5,6-dimethyl-2-methoxypyridin-3-yl)thiocarbamate(200 mg, 0.7 mmol) and 1-(3,5-dimethylphenyl)piperazine(154 mg 0.7 mmol) were dissolved in anhydrous tetrahydrofuran and DBU(106 mg) was added thereto. The mixture was stirred at room temperature for 2 hours and concentrated under the reduced pressure to remove the solvent. The concentrate was purified by column chromatography(ethylacetate:hexane=1:2) to obtain the titled compound.

yield: 50% m.p.: 192–193° C.

$^1$H NMR(CDCl$_3$) δ: 2.21(3H,s), 2.29(6H,s), 2.36(3H,s), 3.33(4H,t), 3.96(3H,s), 4.09(4H,t), 6.57(3H,m), 7.33(1H,s), 8.11(1H,s)

Mass(EI) m/z: Calcd for $C_{21}H_{28}N_4O_1S_1$ 384.1983, found 384.1992

EXAMPLE 23

1-[(5,6-Dimethyl-2-methoxypyridin-3-yl) aminothiocarbonyl]-4-(3,5-difluorophenyl) piperazine Phenyl N-(5,6-dimethyl-2-methoxypyridin-3-yl)thiocarbamate and 1-(3,5-difluorophenyl)piperazine were reacted by the same way with the example 22 to obtain the titled compound.

yield: 47% m.p.: 60–62° C.

$^1$H NMR(CDCl$_3$) δ: 2.21(3H,s), 2.36(3H,s), 3.39(4H,t), 3.96(3H,s), 4.10(3H,t), 6.29(3H,m), 7.33(1H,s), 8.14(1H,s)

EXAMPLE 24

1-[(5,6-Dimethyl-2-methoxypyridin-3-yl) aminothiocarbonyl]-4-(3-hydroxyphenyl)piperazine Phenyl N-(5,6-dimethyl-2-methoxypyridin-3-yl)thiocarbamate and 1-(3-hydroxyphenyl)piperazine were reacted by the same way with the example 22 to obtain the titled compound.

yield: 43% m.p.: 185–186° C.

$^1$H NMR(CDCl$_3$) δ: 2.14(3H,s), 2.36(3H,s), 3.25(4H,t), 3.89(3H,s), 4.09(4H,t), 6.30(1H,d), 6.36(2H,m), 7.03(1H,t), 7.48(1H,s), 8.56(1H,s)

EXAMPLE 25

1-[(2-Methoxy-6-methyl-5-propylpyridin-3-yl) aminothiocarbonyl]-4-(3,5-dimethoxyphenyl) piperazine Phenyl N-(2-methoxy-6-methyl-5-propylpyridin-3-yl)thiocarbamate and 1-(3,5-dimethoxyphenyl)piperazine were reacted by the same way with the example 22 to obtain the titled compound.

yield: 55% m.p.: 143–144° C.

$^1$H NMR(CDCl$_3$) δ: 0.93(3H,t), 1.66(2H,m), 2.17(3H,s), 2.65(2H,t), 3.38(4H,t), 3.79(6H,s), 3.98(3H,s), 4.15(4H,t), 6.11(3H,m), 7.43(1H,s), 8.25(1H,s)

EXAMPLE 26

1-[(2-Methoxy-5-methyl-6-propylpyridin-3-yl) aminothiocarbonyl]-4-(3,5-dimethoxyphenyl) piperazine Phenyl N-(2-methoxy-5-methyl-6-propylpyridin-3-yl)thiocarbamate and 1-(3,5-dimethoxyphenyl)piperazine were reacted by the same way with the example 22 to obtain the titled compound.

yield: 52% m.p.: 183–184° C.

$^1$H NMR(CDCl$_3$) δ: 0.98(3H,t), 1.72(2H,m), 2.17(3H,s), 2.62(2H,t), 3.39(4H,t), 3.79(6H,s), 3.96(3H,s), 4.19(4H,t), 6.15(3H,m), 7.42(1H,s), 8.08(1H,s)

Mass(EI) m/z: Calcd for $C_{23}H_{32}N_4O_3S_1$ 444.2195, found 444.2171

EXAMPLE 27

1-[(2-Methoxy-5-methyl-6-propylpyridin-3-yl) aminothiocarbonyl]-4-(3,5-dimethylphenyl) piperazine Phenyl N-(2-methoxy-5-methyl-6-propylpyridin-3-yl)thiocarbamate and 1-(3,5-dimethylphenyl)piperazine were reacted by the same way with the example 22 to obtain the titled compound.

yield: 49% m.p.: 195–197° C.

$^1$H NMR(CDCl$_3$) δ: 0.98(3H,t), 1.73(2H,m), 2.18(6H,s), 2.34(3H,s), 2.62(2H,t), 3.47(4H,t), 3.96(3H,s), 4.01(4H,t), 6.59(3H,m), 7.02(1H,s), 7.99(1H,s)

Mass(EI) m/z: Calcd for $C_{23}H_{32}N_4O_1S_1$ 412.2296, found 412.2266

EXAMPLE 28

1-[(2-Methoxy-5-methyl-6-propylpyndin-3-yl) aminothiocarbonyl]-4-(3-hydroxyphenyl)piperazine Phenyl N-(2-methoxy-5-methyl-6-propylpyridin-3-yl)thiocarbamate and 1-(3-hydroxyphenyl)piperazine were reacted by the same way with the example 22 to obtain the titled compound.

yield: 48% m.p.: 160–162° C.

$^1$H NMR(CDCl$_3$) δ: 0.98(3H,t), 1.72(2H,m), 2.22(3H,s), 2.61(3H,t), 3.31(4H,t), 3.95(3H,s), 4.10(4H,t), 6.45(3H,m), 7.12(1H,t), 7.41(1H,s), 8.08(1H,s)

Mass(EI) m/z: Calcd for $C_{21}H_{28}N_4O_2S_1$ 400.1932, found 400.1969

EXAMPLE 29

1-[N-(2-Methoxy-6,7-dihydro-5H-cyclopenta[b] pyridin-3-yl)aminothiocarbonyl]-4-(3,5-dimethoxyphenyl)piperazine Phenyl N-(2-methoxy-6,7-dihydro-5H-cyclopenta[b] pyridin-3-yl)thiocarbamate and 1-(3,5-dimethoxyphenyl)

piperazine were reacted by the same way with the example 22 to obtain the titled compound.

yield: 55% m.p.: 169–170° C.

$^1$H NMR(CDCl$_3$) δ: 2.10(2H,m), 2.89(4H,m), 3.30(4H,t), 3.77(6H,s), 3.98(3H,s), 4.20(4H,t), 6.05(3H,m), 7.37(1H,s), 8.25(1H,s)

EXAMPLE 30

1-[N-(2-Methoxy-6,7-dihydro-5H-cyclopenta[b]pyridin-3-yl)aminothiocarbonyl]-4-(3,5-dimethylphenyl)piperazine Phenyl N-(2-methoxy-6,7-dihydro-5H-cyclopenta[b]pyridin-3-yl)thiocarbamate and 1-(3,5-dimethylphenyl)piperazine were reacted by the same way with the example 22 to obtain the titled compound.

yield: 53% m.p.: 159–161° C.

$^1$H NMR(CDCl$_3$) δ: 2.09(2H,m), 2.28(6H,s), 2.87(4H,m), 3.67(4H,t), 4.00(3H,s), 4.21(4H,t), 6.57(3H,m), 6.93(1H,s), 8.24(1H,s)

EXAMPLE 31

1-[(2-Methoxy-5,6,7,8-tetrahydroquinolin-3-yl)aminothiocarbonyl]-4-(3,5-dimethoxyphenyl)piperazine Phenyl N-[(2-methoxy-5,6,7,8-tetrahydroquinolin-3-yl)thiocarbamate and 1-(3,5-dimethoxyphenyl)piperazine were reacted by the same way with the example 22 to obtain the titled compound.

yield: 56% m.p.: 160–161° C.

$^1$H NMR(CDCl$_3$) δ: 1.77(2H,m), 1.83(2H,m), 2.70(2H,t), 2.76(2H,t), 3.38(4H,t), 3.79(6H,s), 3.96(3H,s), 4.16(4H,t), 6.12(3H,m), 7.45(1H,s), 8.03(1H,s)

EXAMPLE 32

1-[(2-Methoxy-5,6,7,8-tetrahydroquinolin-3-yl)aminothiocarbonyl]-4-(3,5-dimethylphenyl)piperazine Phenyl N-(2-methoxy-5,6,7,8-tetrahydroquinolin-3-yl)thiocarbamate and 1-(3,5-dimethylphenyl)piperazine were reacted by the same way with the example 22 to obtain the titled compound.

yield: 54% m.p.: 200–201° C.

$^1$H NMR(CDCl$_3$) δ: 1.77(2H,m), 1.84(2H,m), 2.34(6H,s), 2.71(3H,t), 2.75(3H,t), 3.47(4H,t), 3.97(3H,s), 4.42(4H,t), 6.35(3H,m), 6.91(1H,s), 7.91(1H,s)

EXAMPLE 33

1-[(5,6-Dimethyl-2-methylaminopyridin-3-yl)aminocarbonyl]-4-(3,5-dimethoxyphenyl)piperazine Phenyl N-(5,6-dimethyl-2-methylaminopyridin-3-yl)carbamate and 1-(3,5-dimethoxyphenyl)piperazine were reacted by the same way with the example 1 to obtain the titled compound.

yield: 53% m.p.: 150–151° C.

$^1$H NMR(CDCl$_3$) δ: 2.29(3H,s), 2.48(3H,s), 3.29(4H,t), 3.45(3H,s), 3.77(6H,s), 3.79(4H,t), 6.10(3H,m), 7.40(1H,s)

EXAMPLE 34

1-[(5,6-Dimethyl-2-methylaminopyridin-3-yl)aminocarbonyl]-4-(3,5-dimethylphenyl)piperazine Phenyl N-(5,6-dimethyl-2-methylaminopyridin-3-yl)carbamate and 1-(3,5-dimethylphenyl)piperazine were reacted by the same way with the example 1 to obtain the titled compound.

yield: 52% m.p.: 160–162° C.

$^1$H NMR(CDCl$_3$) δ: 2.30(9H,s), 2.48(3H,s), 3.31(4H,t), 3.46(3H,s), 3.78(4H,t), 6.60(3H,m), 7.41(1H,s)

EXAMPLE 35

1-[(5-Ethyl-6-methyl-2-methylaminopyridin-3-yl)aminocarbonyl]-4-(3,5-dimethylphenyl)piperazine Phenyl N-(5-ethyl-6-methyl-2-methylaminopyridin-3-yl)carbamate and 1-(3,5-dimethylphenyl)piperazine were reacted by the same way with the example 1 to obtain the titled compound.

yield: 56% m.p.: 143–145° C.

$^1$H NMR(CDCl$_3$) δ: 1.22(3H,t), 2.28(6H,s), 2.52(3H,s), 2.72(2H,q), 3.29(4H,t), 3.45(3H,s), 3.78(4H,t), 6.59(3H,m), 7.41(1H,s)

EXAMPLE 36

1-[(2-Methylamino-6,7-dihydro-5H-cyclopenta[b]pyridin-3-yl)aminocarbonyl]-4-(3,5-dimethoxyphenyl)piperazine Phenyl N-(2-methylamino-6,7-dihydro-5H-cyclopenta[b]pyridin-3-yl)carbamate and 1-(3,5-dimethoxyphenyl)piperazine were reacted by the same way with the example 1 to obtain the titled compound.

yield: 49% m.p.: 148–150° C.

$^1$H NMR(CDCl$_3$) δ: 2.09(2H,m), 2.95(4H,m), 3.30(4H,t), 3.47(3H,s), 3.77(4H,t), 3.80(6H,s), 6.10(3H,m), 7.49(1H,s)

EXAMPLE 37

1-[(2-Methylamino-6,7-dihydro-5H-cyclopenta[b]pyridin-3-yl)aminocarbonyl]-4-(3,5-dimethylphenyl)piperazine Phenyl N-(2-methylamino-6,7-dihydro-5H-cyclopenta[b]pyridin-3-yl)carbamate and 1-(3,5-dimethylphenyl)piperazine were reacted by the same way with the example 1 to obtain the titled compound.

yield: 48% m.p.: 185–187° C.

$^1$H NMR(CDCl$_3$) δ: 2.14(2H,m), 2.29(6H,s), 2.95(4H,m), 3.32(4H,t), 3.47(3H,s), 3.79(4H,t), 6.59(3H,m), 7.48(1H,s)

EXAMPLE 38

1-{[5,6-Dimethyl-2-(4'-t-butoxycarbonylpiperazinyl)pyridin-3-yl]aminocarbonyl}-4-(3,5-dimethoxyphenyl)piperazine Phenyl N-[5,6-dimethyl-2-(4'-t-butoxycarbonylpiperazinyl)pyridin-3-yl]carbamate and 1-(3,5-dimethoxyphenyl)piperazine were reacted by the same way with the example 1 to obtain the titled compound.

yield: 58% m.p.: 74–75° C.

$^1$H NMR(CDCl$_3$) δ: 1.46(9H,s), 2.20(3H,s), 2.21(3H,s), 2.90(4H,t), 3.20(4H,t), 3.55(4H,t), 3.65(4H,t), 3.98(3H,s), 6.02(3H,m), 8.20(1H,s)

EXAMPLE 39

1-{[5,6-Dimethyl-2-(4'-t-butoxycarbonylpiperazinyl) pyridin-3-yl]aminocarbonyl}-4-(3,5-dimethylphenyl) piperazine Phenyl N-[5,6-dimethyl-2-(4'-butoxycarbonylpiperazinyl)pyridin-3-yl]carbamate and 1-(3,5-dimethylphenyl)piperazine were reacted by the same way with the example 1 to obtain the titled compound.

yield: 56% m.p.: 155–156° C.

$^1$H NMR(CDCl$_3$) δ: 1.48(9H,s), 2.22(3H,s), 2.29(6H,s), 2.35(3H,s), 2.95(4H,t), 3.25(4H,t), 3.57(4H,t), 3.67(4H,t), 6.59(3H,m), 8.21(1H,s)

EXAMPLE 40

1-{[5-Ethyl-6-methyl-2-(4'-t-butoxycarbonylpiperazinyl)pyridin-3-yl] aminocarbonyl}-4-(3,5-dimethoxyphenyl)piperazine Phenyl N-[5-ethyl-6-methyl-2-(4'-t-butoxycarbonylpiperazinyl)pyridin-3-yl]carbamate and 1-(3,5-dimethoxyphenyl)piperazine were reacted by the same way with the example 1 to obtain the titled compound.

yield: 52% m.p.: 119–120° C.

$^1$H NMR(CDCl$_3$) δ: 1.25(3H,t), 1.48(9H,s), 2.38(3H,s), 2.51(2H,q), 2.96(4H,t), 3.27(4H,t), 3.58(8H,m), 3.78(6H,s), 6.08(3H,m), 8.24(1H,s)

EXAMPLE 41

1-{[5-Ethyl-6-methyl-2-(4'-t-butoxycarbonylpiperazinyl)pyridin-3-yl] aminocarbonyl}-4-(3,5-dimethylphenyl)piperazine Phenyl N-[5-ethyl-6-methyl-2-(4'-t-butoxycarbonylpiperazinyl)pyridin-3-yl]carbamate and 1-(3,5-dimethylphenyl)piperazine were reacted by the same way with the example 1 to obtain the titled compound.

yield: 50% m.p.: 126–128° C.

$^1$H NMR(CDCl$_3$) δ: 1.20(3H,t), 1.49(9H,s), 2.29(6H,s), 2.39(3H,s), 2.52(2H,q), 2.98(4H,t), 3.23(4H,t), 3.59(8H,m), 6.59(3H,m), 7.58(1H,s), 8.26(1H,s)

EXAMPLE 42

1-[(5,6-Dimethyl-2-piperazinylpyridin-3-yl) aminocarbonyl]-4-(3,5-dimethoxyphenyl)piperazine 1-{[5,6-Dimethyl-2-(4'-t-butoxycarbonylpiperazinyl) pyridin-3-yl]aminocarbonyl}-4-(3,5-dimethoxyphenyl) piperazine(0.218 g, 0.4 mmol) was dissolved in dichloromethane:nitromethane=2:1(10 ml) and anisole(0.26 g, 2.4 mmol) and aluminum chloride(0.3 g, 2.4 mmol) were added slowly thereto. The mixture was stirred at room temperature for 20 min. Distilled water(50 ml) was added into the mixture and the mixture was made basic with saturated NaHCO$_3$ and extracted with dichloromethane and then concentrated under the reduced pressure to remove the solvent. The concentrate was purified by column chromatography(methanol:dichloromethane=8:1) to obtain the titled compound.

yield: 89% m.p.: oil phase $^1$H NMR(CDCl$_3$) δ: 2.21(3H,s), 2.35(3H,s), 3.02(4H,t), 3.34(4H,t), 3.59(4H,t), 3.62(4H,t), 3.78(6H,s), 6.08(3H,m), 8.18(1H,s)

EXAMPLE 43

1-[(5,6-Dimethyl-2-piperazinylpyridin-3-yl) aminocarbonyl]-4-(3,5-dimethylphenyl)piperazine 1-{[5,6-Dimethyl-2-(4'-t-butoxycarbonylpiperazinyl) pyridin-3-yl]aminocarbonyl}-4-(3,5-dimethylphenyl) piperazine was reacted by the same way with the example 42 to obtain the titled compound.

yield: 85% m.p.: 103–105° C.

$^1$H NMR(CDCl$_3$) δ: 2.16(3H,s), 2.24(6H,s), 2.40(3H,s), 3.30(4H,t), 3.44(4H,t), 3.50(4H,t), 3.81(4H,t), 6.95(3H,m), 7.72(1H,s)

EXAMPLE 44

1-[(5-Ethyl-6-methyl-2-piperazinylpyridin-3-yl) aminocarbonyl]-4-(3,5-dimethoxyphenyl)piperazine 1-{[5-Ethyl-6-methyl-2-(4'-t-butoxycarbonylpiperazinyl) pyridin-3-yl]aminocarbonyl}-4-(3,5-dimethoxyphenyl) piperazine was reacted by the same way with the example 42 to obtain the titled compound.

yield: 88% m.p.: 68–70° C.

$^1$H NMR(CDCl$_3$) δ: 1.20(3H,t), 2.40(3H,s), 2.52(2H,q), 2.75(4H,t), 3.32(4H,t), 3.70(8H,m), 3.78(6H,s), 6.09(3H,m), 7.68(1H,s), 8.23(1H,s)

EXAMPLE 45

1-[(5-Ethyl-6-methyl-2-piperazinylpyridin-3-yl) aminocarbonyl]-4-(3,5-dimethylphenyl)piperazine 1-{[5-Ethyl-6-methyl-2-(4'-t-butoxycarbonylpiperazinyl) pyridin-3-yl]aminocarbonyl}-4-(3,5-dimethylphenyl) piperazine was reacted by the same way with the example 42 to obtain the titled compound.

yield: 85% m.p.: 100–102° C.

$^1$H NMR(CDCl$_3$) δ: 1.20(3H,t), 2.28(6H,s), 2.39(3H,s), 2.65(2H,q), 2.76(4H,t), 3.00(4H,t), 3.23(4H,t), 3.70(4H,t), 6.58(3H,m), 7.66(1H,s), 8.24(1H,s)

EXAMPLE 46

1-[(5-Acetyl-2-methoxy-6-methylpyridin-3-yl) amninocarbonyl]-4-(3,5-dimethoxyphenyl) piperazine Phenyl N-(5-acetyl-2-methoxy-6-methylpynrdin-3-yl) carbamate(200 mg, 0.67 mmol) and 1-(3,5-dimethoxyphenyl)piperazine(150 mg, 0.67 mmol) were dissolved in anhydrous tetrahydrofuran(15 ml) and DBU(100 mg, 0.67 mmol) was added. The mixture was stirred at room temperature for 2 hrs and concentrated under the reduced pressure to remove tetrahydrofuran. The concentrate was purified by column chromatography(ethylacetate:hexane= 1:2) to obtain the titled compound.

yield: 83% m.p.: 149–151° C.

$^1$H NMR(CDCl$_3$) δ: 2.57(3H,s), 2.65(3H,s), 3.28(4H,t,J= 4.65 Hz), 3.70(4H,t, J=4.65 Hz), 3.79(6H,s), 4.06(3H,s), 6.09(1H,s), 6.14(2H,d),6.94(1H,s), 8.87(1H,s)

EXAMPLE 47

1-[(5-Acetyl-2-methoxy-6-methylpyridin-3-yl) aminocarbonyl]-4-(3,5-dimethylphenyl)piperazine Phenyl N-(5-acetyl-2-methoxy-6-methylpyridin-3-yl) carbamate and 1-(3,5-dimethylphenyl)piperazine were reacted by the same way with the example 46 to obtain the titled compound.

yield: 82% m.p.: 66–69° C.

$^1$H NMR(CDCl$_3$) δ: 2.31(6H,s), 2.57(3H,s), 2.65(3H,s), 3.08(4H,t), 3.30(4H,t), 4.10(3H,s), 6.71(2H,d), 6.94(1H,s), 8.89(1H,s)

EXAMPLE 48

1-[(5-Acetyl-2-methoxy-6-methylpyridin-3-yl) aminocarbonyl]-4-(3,5-difluorophenyl)piperazine Phenyl N-(5-acetyl-2-methoxy-6-methylpyridin-3-yl) carbamate and 1-(3,5-difluorophenyl)piperazine were reacted by the same way with the example 46 to obtain the titled compound.

yield: 77% m.p.: 180–181° C.

$^1$H NMR(CDCl$_3$) δ: 2.57(3H,s), 2.65(3H,s), 3.33(4H,t,J= 5.0 Hz), 3.74(4H,t, J=5.0 Hz), 4.07(3H,s), 6.37(1H,s), 6.46 (2H,d), 6.93(1H,s), 8.85(1H,s)

EXAMPLE 49

1-[(5-Acetyl-2-methoxy-6-methylpyridin-3- yl) aminocarbonyl]-4-(3,5-dichlorophenyl)piperazine Phenyl N-(5-acetyl-2-methoxy-6-methylpyridin-3-yl) carbamate and 1-(3,5-dichlorophenyl)piperazine were reacted by the same way with the example 46 to obtain the titled compound.

yield: 81% m.p.: oil phase $^1$H NMR(CDCl$_3$) δ: 2.57(3H,s), 2.65(3H,s), 3.34(4H,t), 3.78(4H,t), 4.04(3H,s), 6.93(3H,m), 8.80(1H,s)

EXAMPLE 50

1-[(5-Acetyl-2-methoxy-6-methylpyridin-3-yl) aminocarbonyl]-4-(2,3-dimethylphenyl)piperazine Pheny N-(5-acetyl-2-methoxy-6-methylpyridin-3-yl) carbamate and 1-(2,3-dimethylphenyl)piperazine were reacted by the same way with the example 46 to obtain the titled compound.

yield: 81% m.p.: 173–174° C.

$^1$H NMR(CDCl$_3$) δ: 2.29(6H,s), 2.58(3H,s), 2.65(3H,s), 2.98(4H,t), 3.70(4H,t), 4.06(3H,s), 6.91(1H,d), 6.97(1H,s), 7.10(1H,t), 8.89(1H,s)

EXAMPLE 51

1-[(5-Acetyl-2-methoxy-6-methylpyridin-3-yl) aminocarbonyl]-4-(2-methoxyphenyl)piperazine Phenyl N-(5-acetyl-2-methoxy-6-methylpyridin-3-yl) carbamate and 1-(2-methoxyphenyl)piperazine were reacted by the same way with the example 46 to obtain the titled compound.

yield: 79% m.p.: 153–154° C.

$^1$H NMR(CDCl$_3$) δ: 2.58(3H,s), 2.65(3H,s), 3.15(4H,t), 3.73(4H,t), 3.90(3H,s), 4.06(3H,s), 6.91(1H,d), 6.96(1H,d), 6.97(1H,s), 7.10(1H, 8.89(1H,s)

EXAMPLE 52

1-[(5-Acetyl-2-methoxy-6-methylpyridin-3-yl) aminocarbonyl]-4-(3-hydroxyphenyl)piperazine Phenyl N-(5-acetyl-2-methoxy-6-methylpyridin-3-yl) carbamate and 1-(3-hydroxyphenyl)piperazine were reacted by the same way with the example 46 to obtain the titled compound.

yield: 76% m.p.: oil phase $^1$H NMR(CDCl$_3$) δ: 2.60(3H,s), 2.72(3H,s), 3.34(4H,t), 3.79(4H,t), 3.98(3H,s), 6.45(3H,m), 6.98(1H,m), 8.97(1H,s)

EXAMPLE 53

1-[(5-Acetyl-2-methoxy-6-methylpyridin-3-yl) aminothiocarbonyl]-4-( 3,5-dimethoxyphenyl) piperazine Phenyl N-(5-acetyl-2-methoxy-6-methylpyridin-3-yl) thiocarbamate and 1-(3,5-dimethoxyphenyl)piperazine were reacted by the same way with the example 22 to obtain the titled compound.

yield: 77% m.p.: 167–169° C.

$^1$H NMR(CDCl$_3$) δ: 2.58(3H,s), 2.68(3H,s), 3.47(4H,t), 3.81(6H,s), 4.05(3H,s), 4.36(4H,t), 6.42(3H,m), 7.49(1H,s), 9.05(1H,s)

EXAMPLE 54

1-[(5-Acetyl-2-methoxy-6-methylpyridin-3-yl) aminothiocarbonyl]-4-(3,5-dimethylphenyl) piperazine Phenyl N-(5-acetyl-2-methoxy-6-methylpyridin-3-yl) thiocarbamate and 1-(3,5-dimethylphenyl)piperazine were reacted by the same way with the example 22 to obtain the titled compound.

yield: 75% m.p.: 176–177° C.

$^1$H NMR(CDCl$_3$) δ: 2.34(6H,s), 2.58(3H,s), 2.68(3H,s), 3.48(4H,t), 4.06(3H,s), 4.43(4H,t), 7.05(3H,m), 7.52(1H,s), 9.04(1H,s)

EXAMPLE 55

1-[(5-Acetyl-2-methoxy-6-methylpyridin-3-yl) aminothiocarbonyl]-4-(3-hydroxyphenyl)piperazine Phenyl N-(5-acetyl-2-methoxy-6-methylpynidin-3-yl) thiocarbamate and 1-(3-hydroxyphenyl)piperazine were reacted by the same way with the example 22 to obtain the titled compound.

yield: 71% m.p.: 114–115° C.

$^1$H NMR(CDCl$_3$) δ: 2.56(3H,s), 2.75(3H,s), 3.68(4H,t), 4.05(3H,s), 4.45(4H,t), 7.30(4H,m), 9.03(1H,s)

Mass(EI) m/z: Calcd for C$_{23}$H$_{30}$N$_4$O$_4$S$_1$ 458.1987, found 458.2527

EXAMPLE 56

1-{[5-(1-Hydroxyethyl)-2-methoxy-6-methylpyridin-3-yl]aminocarbonyl}-4-(3,5-dimethoxyphenyl)piperazine 1-[(5-Acetyl-2-methoxy-6-methylpyridin-3-yl)aminocarbonyl]-4-(3,5-dimethoxyphenyl)piperazine(100 mg, 0.23 mmol) was dissolved in anhydrous ethanol(15 ml) and NaBH$_4$(8.66 mg) was added. The reaction solution was stirred at room temperature for 2 hours. The mixture was concentrated under the reduced pressure to remove ethanol and purified by column chromatography (ethylacetate:hexane=2:1) to obtain the titled compound.

yield: 97% m.p.: 124–126° C.

$^1$H NMR(CDCl$_3$) δ: 1.48(3H,d), 2.42(3H,s), 3.27(4H,t), 3.69(4H,t), 3.79(6H,s), 3.99(3H,s), 5.03(1H,q), 6.09(1H,s), 6.15(2H,d), 6.90(1H,s), 8.46(1H,s)

Mass(EI) m/z: Calcd for C$_{22}$H$_{30}$N$_4$O$_5$ 430.2216, found 430.2265

EXAMPLE 57

1-{[5-(1-Hydroxyethyl)-2-methoxy-6-methylpyridin-3-yl]aminocarbonyl}-4-(3,5-dimethylphenyl)piperazine 1-[(5-Acetyl-2-methoxy-6-methylpyridin-3-yl)aminocarbonyl]-4-(3,5-dimethylphenyl)piperazine was reacted by the same way with the example 56 to obtain the titled compound.

yield: 95% m.p.: 153–154° C.

$^1$H NMR(CDCl$_3$) δ: 1.48(3H,d), 2.30(6H,s), 2.42(3H,s), 3.26(4H,t), 3.68(4H,t), 3.99(3H,s), 5.05(1H,q), 6.71(2H,d), 6.96(1H,s), 8.46(1H,s)

Mass(EI) m/z: Calcd for C$_{22}$H$_{30}$N$_4$O$_3$ 398.2317, found 398.2343

EXAMPLE 58

1-{[5-(1-Hydroxyethyl)-2-methoxy-6-methylpyridin-3-yl]aminocarbonyl}-4-(2,3-dimethylphenyl)piperazine 1-[(5-Acetyl-2-methoxy-6-methylpyridin-3-yl]aminocarbonyl]-4-(2,3-dimethylphenyl)piperazine was reacted by the same way with the example 56 to obtain the titled compound.

yield: 96% m.p.: 100–102° C.

$^1$H NMR(CDCl$_3$) δ: 1.47(3H,d), 1.59(3H,s), 2.25(3H,s), 2.28(3H,s), 2.43(3H,s), 2.93(4H,t), 3.66(4H,t), 3.99(3H,s), 5.05(1H,q), 6.93(3H,m), 7.11(1H,m), 8.48(1H,s)

EXAMPLE 59

1-{[5-(1-Hydroxyethyl)-2-methoxy-6-methylpyridin-3-yl]aminocarbonyl}-4-(3,5-difluorophenyl)piperazine 1-[(5-Acetyl-2-methoxy-6-methylpyridin-3-yl)aminocarbonyl]-4-(3,5-difluorophenyl)piperazine was reacted by the same way with the example 56 to obtain the titled compound.

yield: 97% m.p.: 184–186° C.

$^1$H NMR(CDCl$_3$) δ: 1.48(3H,d), 2.50(3H,s), 3.30(4H,t), 3.70(4H,t), 4.11(3H,s), 5.06(1H,q), 6.33(1H,s), 6.42(2H,d), 6.92(1H,s), 8.54(1H,s)

EXAMPLE 60

1-{[5-(1-Hydroxyethyl)-2-methoxy-6-methylpyridin-3-yl]aminocarbonyl}-4-(3,5-dichlorophenyl)piperazine 1-[(5-Acetyl-2-methoxy-6-methylpyridin-3-yl)aminocarbonyl]-4-(3,5-dichlorophenyl)piperazine was reacted by the same way with the example 56 to obtain the titled compound.

yield: 95% m.p.: 197–200° C.

$^1$H NMR(CDCl$_3$) δ: 1.46(3H,d), 2.41(3H,s), 3.28(4H,t), 3.66(4H,t), 3.96(3H,s), 5.20(1H,q), 7.02(3H,m), 8.42(1H,s)

EXAMPLE 61

1-{[5-(1-Hydroxyethyl)-2-methoxy-6-methylpyridin-3-yl]aminocarbonyl}-4-(2-methoxyphenyl)piperazine 1-[(5-Acetyl-2-methoxy-6-methylpyridin-3-yl)aminocarbonyl]-4-(2-methoxyphenyl)piperazine was reacted by the same way with the example 56 to obtain the titled compound.

yield: 97% m.p. 88–90° C.

$^1$H NMR(CDCl$_3$) δ: 1.47(3H,d), 2.42(3H,s), 3.11(4H,t), 3.70(4H,t), 3.89(3H,s), 3.99(3H,s), 5.03(1H,q), 6.89(3H,m), 6.94(1H,s), 7.05(1H,m), 8.48(1H,s)

EXAMPLE 62

1-{[5-(1-Hydroxyethyl)-2-methoxy-6-methylpyridin-3-yl]aminocarbonyl}-4-(3-hydroxyphenyl)piperazine 1-[5-Acetyl-2-methoxy-6-methylpyridin-3-yl)aminocarbonyl]-4-(3-hydroxyphenyl)piperazine was reacted by the same way with the example 56 to obtain the titled compound.

yield: 87% m.p.: 194–196° C.

$^1$H NMR(CDCl$_3$) δ: 1.47(3H,d), 2.41(3H,s), 3.27(4H,t), 3.79(4H,t), 3.98(3H,s), 5.04(1H,q), 6.57(3H,m), 6.90(1H,s), 7.13(1H,t), 8.41(1H,s)

EXAMPLE 63

1-{[5-(1-Hydroxyethyl)-2-methoxy-6-methylpyridin-3-yl]aminothiocarbonyl}-4-(3,5-dimethoxyphenyl)piperazine 1-[(5-Acetyl-2-methoxy-6-methylpyridin-3-yl)aminothiocarbonyl]-4-(3,5-dimethoxyphenyl)piperazine was reacted by the same way with the example 56 to obtain the titled compound.

yield: 89% m.p.: 189–190° C.

¹H NMR(CDCl₃) δ: 1.47(3H,d), 2.43(3H,s), 3.35(4H,t), 3.78(6H,s), 3.97(3H,s), 4.09(4H,t), 5.05(1H,q), 6.07(3H,m), 7.35(1H,s), 8.42(1H,s)

EXAMPLE 64

1-{[5-(1-Hydroxyethyl)-2-methoxy-6-methylpyridin-3-yl]aminothiocarbonyl}-4-(3,5-dimethylphenyl)piperazine 1-[(5-Acetyl-2-methoxy-6-methylpyridin-3-yl)aminothiocarbonyl]-4-(3,5-dimethylphenyl)piperazine was reacted by the same way with the example 56 to obtain the titled compound.

yield: 88%
m.p.: 170–172° C.
¹H NMR(CDCl₃) δ: 1.46(3H,d), 2.29(6H,s), 2.43(3H,s), 3.43(4H,t), 3.97(3H,s), 4.10(4H,t), 5.06(1H,q), 6.60(3H,m), 7.37(1H,s), 9.40(1H,s)

EXAMPLE 65

1-{[5-(1-Hydroxy-1-methylethyl)-2-methoxy-6-methylpyridin-3-yl]aminocarbonyl}-4-(3,5-dimethoxyphenyl)piperazine 1-{(5-Acetyl-2-methoxy-6-methylpyridin-3-yl)aminocarbonyl]-4-(3,5-dimethoxyphenyl)piperazine(214 mg, 0.50 mmol) was dissolved in tetrahydrofuran(10 ml) and CH₃MgBr(0.50 ml, 1.50 mmol) was added slowly. The mixture solution was refluxed for 15 hrs and concentrated under the reduced pressure to remove the solvent and extracted with ethylacetate, dried and filtered. The resultant was purified by column chromatography (ethylacetate:hexane=1:2) to obtain the titled compound.

yield: 84%
m.p.: 146–148° C.
¹H NMR(CDCl₃) δ: 1.64(6H,s), 2.64(3H,s), 3.25(4H,t), 3.67(4H,t), 3.78(6H,s), 3.99(3H,s), 6.07(3H,m), 6.86(1H,s), 8.47(1H,s)

EXAMPLE 66

1-{[5-(1-Hydroxy-1-methylethyl)-2-methoxy-6-methylpyridin-3-yl]aminocarbonyl}-4-(3,5-dimethylphenyl)piperazine 1-[(5-Acetyl-2-methoxy-6-methylpyridin-3-yl)aminocarbonyl]-4-(3,5-dimethylphenyl)piperazine was reacted by the same way with the example 65 to obtain the titled compound.

yield: 81%
m.p.: oil phase
¹H NMR(CDCl₃) δ: 1.64(6H,s), 2.29(6H,s), 2.65(3H,s), 3.24(4H,t), 3.67(4H,t), 3.99(3H,s), 6.59(3H,m), 7.05(1H,s), 8.48(1H,s)

EXAMPLE 67

1-{[5-(1-Hydroxy-1-methylpropyl)-2-methoxy-6-methylpyridin-3-yl]aminocarbonyl}-4-(3,5-dimethoxyphenyl)piperazine 1-[(5-Acetyl-2-methoxy-6-methylpyridin-3-yl)aminocarbonyl]-4-(3,5-dimethoxyphenyl)piperazine(214 mg, 0.50 mmol) was dissolved in tetrahydrofuran(10 ml) and C₂H₅MgBr(0.50 mg, 1.50 mmol) was added slowly. The mixture solution was refluxed for 15 hours and concentrated under the reduced pressure to remove the solvent and extracted with ethylacetate, dried and filtered. The resultant was purified by column chromatography (ethylacetate:hexane=1:2) to obtain the titled compound.

yield: 76%
m.p.: 127–129° C.
¹H NMR(CDCl₃) δ: 0.83(3H,t), 1.63(3H,s), 1.94(2H,m), 2.61(3H,s), 3.26(4H,t), 3.68(4H,t), 3.79(6H,s), 3.99(3H,s), 6.08(3H,m), 6.86(1H,s), 8.44(1H,s)

EXAMPLE 68

1-{[5-(1-Hydroxy-1-methylpropyl)-2-methoxy-6-methylpyridin-3-yl]aminocarbonyl)-4-(3,5-dimethylphenyl)piperazine 1-[(5-Acetyl-2-methoxy-6-methylpyridin-3-yl)aminocarbonyl]-4-(3,5-dimethylphenyl)piperazine was reacted by the same way with the example 67 to obtain the titled compound.

yield: 74%
m.p.: 164–165° C.
¹H NMR(CDCl₃) δ: 0.83(3H,t), 1.60(3H,s), 1.95(2H,m), 2.29(6H,s), 2.61(3H,s), 3.23(4H,t), 3.67(4H,t), 3.99(3H,s), 6.59(3H,m), 6.87(1H,s), 8.45(1H,s)

EXAMPLE 69

1-[5-({[4-(3,5-Dimethoxyphenyl)piperazino]carbonyl}amino)-6-methoxy-2-methylpyridin-3-yl] ethyl ethanthioate Triphenylphosphine(262 mg, 1.0 mmol) was dissolved in tetrahydrofuran(15 ml) and diethyl azodicarboxylate(157 µl, 1.0 mmol) was added and then the mixture was stirred at 0° C. for 30 min.

1-{([5-(1-Hydroxyethyl)-2-methoxy-6-methylpyridin-3-yl]aminocarbonyl}-4-(3,5-dimethoxyphenyl)piperazine(213 mg, 0.5 mmol) and thioacetic acid(72 µl, 1.0 mmol) were dissolved in tetrahydrofuran and was added into the above solution. The mixture solution was stirred at 0° C. for 1 hour and at room temperature for 1 hour and then was concentrated under the reduced pressure to remove the solvent. The concentrate was purified by column chromatography (ethylacetate:hexane=1:2) to obtain the titled compound.

yield: 62%
m.p.: oil phase
¹H NMR(CDCl₃) δ: 1.55(3H,d), 2.20(3H,s), 2.39(3H,s), 3.15(4H,t), 3.57(4H,t), 3.69(6H,s), 3.90(3H,s), 4.74(1H,q), 6.01(3H,m), 6.89(1H,s), 8.33(1H,s)

EXAMPLE 70

1-[5-({[4-(3,5-Dimethylphenyl)piperazino]carbonyl}amino)-6-methoxy-2-methylpyridin-3-yl] ethyl ethanthioate 1-{[5-(1-Hydroxyethyl)-2-methoxy-6-methylpyridin-3-yl]aminocarbonyl}-4-(3,5-dimethylphenyl)piperazine was reacted by the same way with the example 69 to obtain the titled compound.

yield: 60%
m.p.: oil phase
¹H NMR(CDCl₃) δ: 1.60(3H,d), 2.26(6H,s), 2.52(3H,s), 3.20(4H,t), 3.64(4H,t), 3.96(3H,s), 4.80(1H,q), 6.56(3H,m), 6.91(1H,s), 8.38(1H,s)

EXAMPLE 71

1-{[2-Methoxy-6-methyl-5-(1-sulfanylmethyl)]aminocarbonyl}-4-(3,5-dimethoxyphenyl)piperazine 1-[5-({[4-(3,5-Dimethoxyphenyl)piperazino]carbonyl}amino)-6-methoxy-2-methylpyridin-3-yl]ethyl ethanthioate(180 mg, 0.37 mmol) was dissolved in tetrahydrofuran(15ml) and LiAlH$_4$(15 mg, 0.4 mmol) was added and then the mixture was stirred at 0° C. for 20 min. 2N-HCl was added the above solution. The mixture was concentrated under the reduced pressure to remove the solvent and extracted with dichloromethane, dried and filtered. The resultant was concentrated under the reduced pressure and purified by column chromatography (ethylacetate:hexane=1:2) to obtain the titled compound.

yield: 88% m.p.: oil phase $^1$H NMR(CDCl$_3$) δ: 1.42(3H,d), 2.39(3H,s), 3.25(4H,t), 3.66(4H,t), 3.76(6H,s), 3.96(3H,s), 5.02(1H,q), 6.17(3H,m), 6.87(1H,s), 8.41(1H,s)

EXAMPLE 72

1-{[2-Methoxy-6-methyl-5-(1-sulfanylmethyl)]aminocarbonyl}-4-(3,5-dimethylphenyl)piperazine 1-[5-({[4-(3,5-Dimethylphenyl)piperazino]carbonyl}amino)-6-methoxy-2-methylpyridin-3-yl]ethyl ethanthioate was reacted by the same way with the example 71 to obtain the titled compound.

yield: 87% m.p.: oil phase $^1$H NMR(CDCl$_3$) δ: 1.43(3H,d), 2.28(6H,s), 2.40(3H,s), 3.25(4H,t), 3.72(4H,t), 5.03(1H,q), 6.64(3H,m), 6.88(1H,s), 8.42(1H,s)

EXAMPLE 73

1-[(2-Methoxy-6-methyl-5-vinylpyridin-3-yl)aminocarbonyl]-4-(3,5-dimethoxyphenyl)piperazine 1-{[5-(1-Hydroxyethyl-2-methoxy-6-methylpyridin-3-yl)aminocarbonyl}-4-(3,5-dimethoxyphenyl)piperazine was dissolved in chloroform(15 ml) and pyridinum p-toluensulfonate(60 mg, 0.23 mmol) was added and then the mixture solution was refluxed 16 hours. The above solution was concentrated under the reduced pressure to remove chloroform and purified by column chromatography to obtain the titled compound.

yield: 93% m.p.: 140–141° C.

$^1$H NMR(CDCl$_3$) δ: 2.43(3H,s), 3.27(4H,t), 3.69(4H,t), 3.79(6H,s), 4.00(3H,s), 5.25(1H,d), 5.65(1H,d), 6.08(1H,s), 6.13(2H,d), 6.82(1H,d), 6.91(1H,s), 8.53(1H,s)

Mass(EI) m/z: Calcd for C$_{22}$H$_{28}$N$_4$O$_4$ 412.2110, found 412.2119

EXAMPLE 74

1-[(2-Methoxy-6-methyl-5-vinylpyridin-3-yl)aminocarbonyl]-4-(3,5-dimethylphenyl)piperazine 1-{[5-(1-Hydroxyethyl)-2-methoxy-6-methylpyridin-3-yl]aminocarbonyl}-4-(3,5-dimethylphenyl)piperazine was reacted by the same way with the example 73 to obtain the titled compound.

yield: 94% m.p.: 131–132° C.

$^1$H NMR(CDCl$_3$) δ: 1.57(3H,s), 2.31(6H,s), 2.43(1H,s), 3.25(4H,t), 3.68(4H,t), 4.00(3H,s), 5.25(1H,d), 5.65(1H,d) 6.60(3H,m), 6.82(1H,dd), 6.92(1H,s), 8.53(1H,s)

Mass(EI) m/z: Calcd for C$_{22}$H$_{28}$N$_4$O$_2$ 380.2212, found 380.2236

EXAMPLE 75

1-[(2-Methoxy-6-methyl-5-vinylpyridin-3-yl)aminocarbonyl]-4-(3,5-difluorophenyl)piperazine 1-{[5-(1-Hydroxyethyl)-2-methoxy-6-methylpyridin-3-yl]aminocarbonyl}-4-(3,5-difluorophenyl)piperazine was reacted by the same way with the example 73 to obtain the titled compound.

yield: 93% m.p.: 160–161° C.

$^1$H NMR(CDCl$_3$) δ: 2.44(3H,s), 3.30(4H,t,J=5.5 Hz), 3.68(4H,t,J=5.5 Hz), 4.01(3H,s), 5.26(1H,d), 5.65(1H,d), 6.30(1H,s), 6.39(2H,d), 6.81(1H,dd), 8.53(1H,s)

Mass(EI) m/z: Calcd for C$_{22}$H$_{28}$N$_4$O$_4$ 412.2110, found 412.2102

EXAMPLE 76

1-[(5-Isopropenyl-2-methoxy-6-methylpyridin-3-yl)aminocarbonyl]-4-(3,5-dimethoxyphenyl)piperazine -{[5-(1-Hydroxy-1-methylethyl)-2-methoxy-6-methylpyridin-3-yl)aminocarbonyl]}-4-(3,5-dimethoxyphenyl)piperazine was reacted by the same way with the example 73 to obtain the titled compound.

yield: 96% m.p.: 83–85° C.

$^1$H NMR(CDCl$_3$) δ: 2.01(3H,s), 2.38(3H,s), 3.25(4H,t) 3.66(4H,t), 3.78(6H,s), 3.99(3H,s), 4.86(1H,s), 5.30(1H,s), 6.11(3H,m), 6.90(1H,s), 8.18(1H,s)

EXAMPLE 77

1-[(5-Isopropenyl-2-methoxy-6-methylpyridin-3-yl)aminocarbonyl]-4-(3,5-dimethylphenyl)piperazine 1-{[5-(1-Hydroxy-1-methylethyl)-2-methoxy-6-methylpylidin-3-yl]aminocarbonyl}-4-(3,5-dimethylphenyl)piperazine was reacted by the same way with example 73 to obtain the titled compound.

yield: 93% m.p.: 140–142° C.

$^1$H NMR(CDCl$_3$) δ: 2.01(3H,s), 2.29(6H,s), 2.28(3H,s), 3.23(4H,t), 3.66(4H,t), 3.99(3H,s), 4.86(1H,s), 5.18(1H,s), 6.59(3H,m), 6.91(1H,s), 8.18(1H,s)

EXAMPLE 78

Ethyl 2-{1-[5-({[4-(3,5-dimethoxyphenyl)piperazino]carbonyl}amino)-6-methoxy-2-methylpyridin-3-yl]ethoxy}acetate 1-{[5-(1-Hydroxy)-2-methoxy-6-methylpyridin-3-yl]aminocarbonyl}-4-(3,5-dimethoxyphenyl)piperazine(0.5 mmol) was dissolved in dimethylformamide(15 ml) and NaH(18.5 mg, 0.5 mmol) was added and then the mixture solution was stirred at room temperature for 15 min. Ethylbromoacetate(83.5 mg, 0.5 mmol) was added into the above mixture and stirred at room temperature for 3 hours. The mixture was concentrated under the reduced pressure to remove the solvent and purified by column chromatography (ethylacetate:hexane=1:2) to obtain the titled compound.

yield: 89% m.p.: oil phase $^1$H NMR(CDCl$_3$) δ: 1.25(3H,t), 1.34(3H,d), 2.42(3H,s), 3.00(4H,t), 3.29(4H,t), 3.74(6H,s), 3.97(3H,s), 4.16(4H,s), 4.53(1H,q), 6.03(3H,m), 7.58(1H,s)

EXAMPLE 79

4-{1-[5-({[4-(3,5-Dimethoxyphenyl)piperazino]carbonyl}amino)-6-methoxy-2-methylpyridin-3-yl]ethoxy}-4-oxobutanoic acid 1-{[5-(1-Hydroxyethyl)-2-methoxy-6-methylpyridin-3-yl]aminocarbonyl}-4-(3,5-dimethoxyphenyl)piperazine(107 mg, 0.25 mmol) and dimethylaminopyridine(3 mg, 0.025 mmol) were dissolved in pyridine and anhydrous succinic acid(50 mg, 0.5 mmol) was added. The mixture was stirred at room temperature for 5 hrs. Distilled water was added into the above mixture. The above solution was extracted with $CH_2Cl_2$ and the organic phase washed with 1N-HCl and then concentrated under the reduced pressure to remove the solvent. The concentrate was purified by column chromatography(dichloromethane:methanol=20:1) to obtain the titled compound.

yield: 78% m.p.: 158–160° C.

$^1$H NMR($CDCl_3$) δ: 1.42(3H,d), 2.43(3H,s), 2.61(4H,m), 3.24(4H,t), 3.66(4H,t), 3.76(6H,s), 3.95(3H,s), 5.94(1H,q), 6.04(3H,m), 6.89(1H,s), (8.13(1H,s)

EXAMPLE 80

4-{1-[5-({[4-(3,5-Dimethylphenyl)piperazino]carbonyl}amino)-6-methoxy- 2-methylpyridin-3-yl]ethoxy}-4-oxobutanoic acid 1-{[5-(1-hydroxyethyl)-2-methoxy-6-methylpyridin-3-yl]aminocarbonyl}-4-(3,5-dimethylphenyl)piperazine was reacted by the same way with the example 79 to obtain the titled compound.

yield: 76% m.p.: 138–140° C.

$^1$H NMR($CDCl_3$) δ: 1.43(3H,d), 2.27(6H,s), 2.55(3H,s), 2.65(4H,m), 3.24(4H,t), 3.69(4H,t), 3.95(3H,s), 5.95(1H,q), 6.60(3H,m), 6.88(1H,s), 8.11(1H,s)

EXAMPLE 81

1-[(2-Methoxyquinolin-3-yl)aminocarbonyl]-4-(3,5-dimethoxyphenyl)piperazine a) Phenyl N-(2-methoxyquinolin-3-yl)carbamate 3-Amino-2-methoxyquinoline(4 g, 23 mmol) and phenyl chloroformate(4.04 g, 25 mmol) were dissolved in dichloromethane and stirred at room temperature for 2 hours. The above mixture was concentrated under the reduced pressure to remove dichloromethane and purified by column chromatography(hexane:ether=8:1) to obtain the titled compound.

yield: 75% m.p.: oil phase $^1$H NMR ($CDCl_3$): δ 4.01(3H,s), 7.30(5H,s), 7.41(1H,t), 7.70(1H,d), 7.71 (1H,d), 8.71 (1H,s)

b) 1-[(2-Methoxyquinolin-3-yl)aminocarbonyl]-4-(3,5-dimethoxyphenyl)piperazine

Phenyl N-(2-methoxyquinolin-3-yl)carbamate(148 mg, 0.5 mmol) and 1-(3,5-dimethoxyphenyl)piperazine(112 mg, 0.5 mmol) were dissolved in anhydrous tetrahydrofuran and DBU(117 mg, 0.75 mmol) was added. The solution was stirred at room temperature for 2 hours. The mixture was concentrated under the reduced pressure to remove tetrahydrofuran and purified by column chromatography (hexane:ether=5:1) to obtain the titled compound.

yield: 81% m.p.: 200–201° C.

$^1$H NMR ($CDCl_3$): δ 3.31(4H,t,J=5.0 Hz), 3.74(4H,t), 3.79(6H,s), 4.17(3H,s), 6.09(1H,s), 6.17(2H,s), 7.35(1H,t), 7.49(1H,t), 7.71(1H,d), 7.78(1H,d), 8.78(1H,s)

Mass(EI) m/z: Calcd for $C_{23}H_{26}N_4O_4$ 422.1954, found 422.1952

EXAMPLE 82

1-[(2-Methoxyquinolin-3-yl)aminocarbonyl]-4-(3,5-dimethylphenyl)piperazine

Phenyl N-(2-methoxyquinolin-3-yl)carbamate and 1-(3, 5-dimethylphenyl)piperazine were reacted by the same way with the example 81 to obtain the titled compound.

yield: 79% m.p.: 143–145° C.

$^1$H NMR ($CDCl_3$): δ 2.30(6H,s), 3.29(4H,t), 3.80(4H,t), 4.18(3H,s), 6.62(3H,m), 7.36(1H,t), 7.49(1H,t), 7.71(1H,d), 7.78(1H,d), 8.79(1H,s)

Mass(EI) m/z: Calcd for $C_{23}H_{26}N_4O_2$ 390.2055, found 390.2066

EXAMPLE 83

1-[(2-Methoxyquinolin-3-yl)aminocarbonyl]-4-(2,3-dimethylphenyl)piperazine

Phenyl N-(2-methoxyquinolin-3-yl)carbamate and 1-(2, 3-dimethylphenyl)piperazine were reacted by the same way with the example 81 to obtain the titled compound.

yield: 83% m.p.: 174–175° C.

$^1$H NMR ($CDCl_3$): δ 2.20(3H,s), 2.39(3H,s), 3.28(4H,t), 3.69(4H,t), 3.93(3H,s), 5.98(1H,s), 6.30(1H,t), 6.37(1H,s), 6.39(1H,s), 6.63(1H,s)

EXAMPLE 84

1-[(2-Methoxyquinolin-3-yl)aminocarbonyl]-4-(3,5-difluorophenyl)piperazine

Phenyl N-(2-methoxyquinolin-3-yl)carbamate and 1-(3, 5-difluorophenyl)piperazine were reacted by the same way with the example 81 to obtain the titled compound.

yield: 78% m.p.: 158–159° C.

$^1$H NMR ($CDCl_3$): δ 3.32(4H,t,J=5.0 Hz), 3.72(4H,t,J= 5.0 Hz), 4.19(3H,s), 6.29(1H,s), 6.39(2H,d), 7.36(1H,t), 7.50(1H,t), 7.71(1H,d), 7.81(1H,d), 8.78(1H,s)

EXAMPLE 85

1-[(2-Methoxyquinolin-3-yl)aminocarbonyl]-4-(3,5-dichlorolphenyl)piperazine

Phenyl N-(2-methoxyquinolin-3-yl)carbamate and 1-(3, 5-dichlorophenyl)piperazine were reacted by the same way with the example 81 to obtain the titled compound.

yield: 56% m.p.: 156–158° C.

$^1$H NMR ($CDC_3$): δ 3.33(4H,t), 3.73(4H,t), 4.21(3H,s) 6.79(1H,s), 6.83(1H,d), 6.93(1H,t), 7.26(1H,t), 7.38(1H,t), 7.52(1H,t), 7.71(1H,d), 7.83(1H,d)

Mass(EI) m/z: Calcd for $C_{21}H_{20}N_4O_2Cl_1$ 430.0963, found 430.0977

EXAMPLE 86

1-[(2-Methoxyquinolin-3-yl)aminocarbonyl]-4-(2-fluorophenyl)piperazine

Phenyl N-(2-methoxyquinolin-3-yl)carbamate and 1-(2-fluorophenyl)piperazine were reacted by the same way with the example 81 to obtain the titled compound.

yield: 81% m.p.: 156–158° C.

$^1$H NMR (CDCl$_3$): δ 3.18(4H,t), 3.74(4H,t), 4.18(3H,s), 6.99(2H,q), 7.07(2H,m), 7.35(2H,m), 7.50(1H,t), 7.70(1H,d), 7.77(1H,d)

EXAMPLE 87

1-[(2-Methoxyquinolin-3-yl)aminocarbonyl]-4-(2-chlorophenyl)piperazine

Phenyl N-(2-methoxyquinoline-3-yl)carbamate and 1-(2-chlorophenyl)piperazine were reacted by the same way with the example 81 to obtain the titled compound.

yield: 78% m.p.: 79–80° C.

$^1$H NMR (CDCl$_3$): δ 3.32(4H,t), 3.74(41H,t), 4.20(3H,s), 6.82(2H,q), 6.94(2H,m), 7.34(2H,m), 7.48(1H,d), 7.70(1H,d), 7.78(1H,d)

EXAMPLE 88

1-[(2-Methoxyquinolin-3-yl)aminocarbonyl]-4-(3-chlorophenyl)piperazine

Phenyl N-(2-methoxyquinolin-3-yl)carbamate and 1-(3-chlorophenyl)piperazine were reacted by the same way with the example 81 to obtain the titled compound.

yield: 73% m.p.: 97–98° C.

$^1$H NMR (CDCl$_3$): δ 3.31(4H,t), 3.73(4H,t), 4.18(3H,s), 6.82(1H,d), 6.87(1H,d), 6.92(1H,s), 7.21(1H,t), 7.32(1H,s), 7.37(1H,t), 7.51(1H,t), 7.70(1H,d), 7.78(1H,d), 8.80(1H,s)

EXAMPLE 89

1-[(2-Methoxyquinolin-3-yl)aminocarbonyl]-4-(3-hydroxyphenyl)piperazine

Phenyl N-(2-methoxyquinolin-3-yl)carbamate and 1-(3-hydroxyphenyl)piperazine were reacted by the same way with the example 81 to obtain the titled compound.

yield: 75% m.p.: 190–191° C.

$^1$H NMR (CDCl$_3$): δ 3.33(4H,t), 3.80(4H,t), 4.19(3H,s), 6.47(1H,s), 6.62(2H,s), 7.16(1H,t), 7.32(1H,s), 7.37(1H,t), 7.51(1H,t), 7.72(1H,d), 7.78(1H,d), 8.78(1H,s)

EXAMPLE 90

1-[(2-Methoxyquinolin-3-yl)aminocarbonyl]-4-(2-methoxyphenyl)piperazine

Phenyl N-(2-methoxyquinolin-3-yl)carbamate and 1-(2-methoxyphenyl)piperazine were reacted by the same way with the example 81 to obtain the titled compound.

yield: 88% m.p.: 159–161° C.

$^1$H NMR (CDCl$_3$): δ 3.28(4H,t), 3.71(4H,t), 3.81(3H,s), 4.18(3H,s), 6.52(2H,s), 6.62(1H,s), 7.23(1H,t), 7.31–7.53 (3H,m), 7.72(2H,m), 8.81(1H,s)

EXAMPLE 91

1-[(2-Methoxyquinolin-3-yl)aminocarbonyl]-4-(2-methylthiophenyl)piperazine

Phenyl N-(2-methoxyquinolin-3-yl)carbamate and 1-(2-methylthiophenyl)piperazine were reacted by the same way with the example 81 to obtain the titled compound.

yield: 78% m.p.: 147–149° C.

$^1$H NMR (CDCl$_3$): δ 2.44(3H,s), 3.07(4H,t), 3.75(4H,t), 4.18(3H,s), 7.13(3H,m), 7.18(1H,d), 7.39(2H,m), 7.70(3H,m), 8.81(1H,s)

EXAMPLE 92

1-[(2-Methoxyquinolin-3-yl)aminocarbonyl]-4-(3-isopropoxyphenyl)piperazine

Phenyl N-(2-methoxyquinolin-3-yl)carbamate and 1-(3-isopropoxyphenyl)piperazine were reacted by the same way with the example 81 to obtain the titled compound.

yield: 93% m.p.: 111–113° C.

$^1$H NMR (CDCl$_3$): δ 1.34(6H,d), 3.30(4H,t), 3.74(4H,t), 4.18(3H,s), 4.55(1H,m), 6.49(2H,s), 7.05(1H,s), 7.20(1H,t), 7.32(1H,s), 7.37(1H,t), 7.50(3H,t), 7.70(1H,d), 7.77(2H,d), 8.80(1H,s)

EXAMPLE 93

1-[(2-Methoxyquinolin-3-yl)aminocarbonyl]-4-(3-cyclopropylmethoxyphenyl)piperazine Phenyl N-(2-methoxyquinolin-3-yl)carbamate and 1-(3-cyclopropylmethoxyphenyl)piperazine were reacted by the same way with the example 81 to obtain the titled compound.

yield: 90% m.p.: 146–147° C.

$^1$H NMR (CDCl$_3$): δ 0.36(2H,t), 0.65(2H,m), 1.28(4H,m), 3.31(4H,t), 3.75(4H,t), 3.80(2H,d), 4.10(3H,s), 6.50(1H,s), 6.60(2H,s), 7.19(1H,t), 7.32(1H,s), 7.37(1H,t), 7.50(1H,t), 7.70(1H,d), 7.77(1H,d), 8.79(1H,s)

EXAMPLE 94

1-[(2-Methoxyquinolin-3-yl)aminocarbonyl]-4-(2-methoxy-5-methylphenyl)piperazine Phenyl N-(2-methoxyquinolin-3-yl)carbamate and 1-(2-methoxy-5-methylphenyl)piperazine were reacted by the same way with the example 81 to obtain the titled compound.

yield: 76% m.p.: 115–116° C.

$^1$H NMR (CDCl$_3$): δ 2.30(3H,s), 3.14(4H,t), 3.75(4H,t), 3.87(3H,s), 4.18(3H,s), 6.79(2H,m), 6.84(1H,d), 7.35(2H,m), 7.50(1H,t), 7.72(1H,d), 7.77(1H,d), 8.82(1H,s)

EXAMPLE 95

1-[(2-Methoxyquinolin-3-yl)aminocarbonyl]-4-(2-methoxy-5-phenylphenyl)piperazine Phenyl N-(2-methoxyquinolin-3-yl)carbamrate and 1-(2-methoxy-5-phenylphenyl)piperazine were reacted by the same way with the example 81 to obtain the titled compound.

yield: 77% m.p.: 122–123° C.

$^1$H NMR (CDCl$_3$): δ 3.38(4H,t) 3.86(4H,t), 3.97(3H,s), 4.18(3H,s), 7.05(2H,m), 7.34–7.45(6H,m), 7.50(1H,t), 7.56 (2H,d), 7.71(2H,d), 7.78(2H,d), 8.88(1H,s)

EXAMPLE 96

1-[(2-Methoxyquinolin-3-yl)aminocarbonyl]-4-(5-methoxy-2-methylphenyl)piperazine Phenyl N-(2-methoxyquinolin-3-yl)carbamate and 1-(5-methoxy-2-methylphenyl)piperazine were reacted by the same way with the example 81 to obtain the titled compound.

yield: 82% m.p.: 128–130° C.

$^1$H NMR (CDCl$_3$): δ 2.30(3H,s), 3.37(4H,t), 3.84(4H,t), 3.78(3H,s), 3.97(3H,s), 7.05(2H,m), 7.13(1H,d), 7.38(3H, m), 7.62(1H,d), 7.80(1H,s), 8.88(1H,s)

EXAMPLE 97

1-[(2-Methoxyquinolin-3-yl)aminocarbonyl]-4-(1-naphthyl)piperazine

Phenyl N-(2-methoxyquinolin-3-yl)carbamate and 1-(1-naphthyl)piperazine were reacted by the same way with the example 81 to obtain the titled compound.

yield: 68% m.p.: 158–160° C.

$^1$H NMR (CDCl$_3$): δ 3.22(4H,t), 3.86(4H,t), 4.20(3H,s), 7.13(1H,d), 7.38(2H,m), 7.43(1H,t), 7.53(3H,m), 7.62(1H, d), 7.72(1H,d), 7.80(1H,d), 7.86(1H,d), 8.24(1H,d), 8.84 (1H,s)

EXAMPLE 98

1-[N-(2-Methoxyquinolin-3-yl)-N-methylaminocarbonyl]-4-(3,5-dimethoxyphenyl) piperazine 1-[(2-Methoxyquinolin-3-yl)aminocarbonyl]-4-(3,5-dimethoxyphenyl)piperazine(106 mg, 0.25 mmol) was dissolved in dimethylfonnamide(15 ml) and sodium hydride (6.0 mg, 0.25 mmol) was added and the solution was stirred at room temperature for 15 min. Iodomethane(35 mg, 0.25 mmol) was added to the above solution. The mixture was stirred at room temperature for 16 hours and concentrated under the reduced pressure to remove dimethylformamide. The concentrate was purified by column chromatography (ethylacetate:hexane=1:2) to obtain the titled compound.

yield: 93% m.p.: 88–89° C.

$^1$H NMR (CDCl$_3$): δ 2.93(4H,t), 3.17(3H,s), 3.34(4H,t), 3.72(6H,s), 4.15(3H,t), 5.95(2H,s), 5.98(1H,s), 7.40(1H,t), 7.61(2H,m), 7.73(1H,s), 7.94(1H,d)

Mass(EI) m/z: Calcd for C$_{24}$H$_{28}$N$_4$O$_4$ 436.2110, found 436.2105

EXAMPLE 99

1-[N-Ethyl-N-(2-methoxyquinolin-3-yl) aminocarbonyl]-4-(3,5-dimethoxyphenyl)piperazine 1-[(2-Methoxyquinolin-3-yl)aminocarbonyl]-4-(3,5-dimethoxyphenyl)piperazine(106 mg, 0.25 mmol) was dissolved in dimethylformamide(15 ml) and was sodium hydride(6.0 mg, 0.25 mmol) was added and the solution was stirred at room temperature for 15 min. Iodoethane(35 mg, 0.25 mmol) was added to the above solution. The mixture was stirred at room temperature for 16 hours and concentrated under the reduced pressure to remove dimethylformamide. The concentrate was purified by column chromatography(ethylacetate:hexane=1:2) to obtain the titled compound.

yield: 91% m.p.: 118–120° C.

$^1$H NMR (CDCl$_3$): δ 1.16(3H,t), 2.89(4H,t), 3.30(4H,t), 3.63(2H,m), 3.71(6H,s), 4.13(3H,s), 5.93(2H,s), 5.98(1H,s), 7.41(1H,t), 7.60(1H,t), 7.66(1H,d), 7.71(1H,s), 7.84(1H,d)

Mass(EI) m/z: Calcd for C$_{25}$H$_{30}$N$_4$O$_4$ 450.2227, found 450.2206

EXAMPLE 100

1-N-Isopropyl-N-(2-methoxyquinolin-3-yl) aminocarbonyl]-4-(3,5-dimethoxyphenyl)phenyl 1-[(2-Methoxyquinolin-3-yl)aminocarbonyl]-4-(3,5-dimethoxyphenyl)piperazine(106 mg, 0.25 mmol) was dissolved in dimethlylformamide(15 ml) and sodium hydride (6.0 mg, 0.25 mmol) was added and the reaction solution was stirred at room temperature for 15 min.

2-Propyliodide(42 mg, 0.25 mmol) was added to the above solution. The mixture was stirred at room temperature for 16 hours and concentrated under the reduced pressure to remove the dimethylformamide. The concentrate was purified by column chromatography(ethylacetate:hexane=1:2) to obtain the titled compound.

yield: 87% m.p.: 123–125° C.

$^1$H NMR (CDCl$_3$): δ 1.21(6H,d), 2.79(4H,t), 3.29(4H,t), 3.70(6H,s), 4.08(3H,s), 4.41(1H,m), 5.90(2H,s), 5.96(1H,s), 7.43(1H,t), 7.63(1H,t), 7.69(1H,d), 7.75(1H,s), 7.83(1H,d)

EXAMPLE 101

1-[N-Cyclopropylmethyl-N-(2-methoxyquinolin-3-yl)aminocarbonyl]-4-(3,5-dimethoxyphenyl) piperazine 1-[(2-methoxyquinolin-3-yl)aminocarbonyl]-4-(3,5-dimethoxyphenyl)piperazine(106 mg, 0.25 mmol) was dissolved in dimethylformamide(15 ml) and sodium hydride (6.2 mg, 0.26 mmol) was added and the solution was stirred at room temperature for 15 min. Bromomethylcyclopropane (22 mg, 0.26 mmol) was added to the above solution. The mixture was stirred at room temperature for 16 hours and concentrated under the reduced pressure to remove dimethylformamide. The concentrate was purified by column chromatography(ethylacetate:hexane=1:2) to obtain the titled compound.

yield: 78% m.p.: 118–120° C.

$^1$H NMR (CDCl$_3$): δ 0.41(2H,m), 0.85(2H,m), 1.28(1H, m), 2.88(4H,t), 3.24(4H,t), 3.42(2H,d), 3.71(6H,s), 4.13(3H, s), 5.94(3H,s), 7.44(1H,d), 7.62(1H,d), 7.78(3H,m)

EXAMPLE 102

1-[N-Benzyl-N-(2-methoxyquinolin-3-yl) aminocarbonyl]-4-(3,5-dimethoxyphenyl)piperazine 1-[(2-Methoxyquinolin-3-yl)aminocarbonyl]-4-(3,5-dimethoxyphenyl)piperazine(114 mg, 0.27 mmol) was dissolved in dimethylformamide(15 ml) and sodium hydride (6.6 mg, 0.27 mmol) was added and the solution was stirred at room temperature for 15 min. Benzylbromide(46 mg, 0.27 mmol) was added to the above solution. The mixture was stirred at room temperature for 16 hours and concentrated under the reduced pressure to remove dimethylformamide. The concentrate was purified by column chromatography (ethylacetate:hexane=1:2) to obtain the titled compound.

yield: 90% m.p.: oil phase $^1$H NMR (CDCl$_3$): δ 2.92(4H,t), 3.39(4H,t), 3.72(6H,s), 4.13(3H,s), 4.79(2H,s), 6.01(3H,m), 7.21(1H,m), 7.25(2H,m), 7.33(3H,m), 7.51(1H,s), 7.57(2H,m), 7.81(2H,d)

EXAMPLE 103

1-[N-(2-Methoxyquinolin-3-yl)-N-methylaminocarbonyl]-4-(3,5-dimethylphenyl)piperazine 1-[(2-Methoxyquinolin-3-yl)aminocarbonyl]-4-(3,5-dimethylphenyl)piperazine was reacted by the same way with the example 98 to obtain the titled compound.

yield: 92% m.p: 142–143° C.

$^1$H NMR (CDCl$_3$): δ 2.27(6H,d), 2.90(4H,t), 3.17(3H,s), 3.34(4H,t), 4.15(3H,s), 6.41(2H,s), 6.49(1H,s), 7.40(1H,t), 7.63(1H,t), 7.65(1H,d), 7.73(1H,s), 7.84(1H,d)

Mass(EI) m/z: Calcd for C$_{24}$H$_{28}$N$_4$O$_2$ 404.2212, found 404.2225

EXAMPLE 104

1-[N-Ethyl-N-(2-methoxyquinolin-3-yl)aminocarbonyl]-4-(3,5-dimethylphenyl)piperazine 1-[(2-Methoxyquinolin-3-yl)aminocarbonyl]-4-(3,5-dimethylphenyl)piperazine was reacted by the same way with the example 99 to obtain the titled compound.

yield: 89% m.p.: 84–86° C.

$^1$H NMR (CDCl$_3$): δ 1.16(3H,t), 2.21(6H,s), 2.87(4H,t), 3.30(4H,t), 3.64(2H,q), 4.13(3H,t), 6.40(2H,s), 6.48(1H,s), 7.40(1H,t), 7.62(1H,t), 7.66(1H,d), 7.71(1H,s), 7.84(1H,d)

EXAMPLE 105

1-[N-Isopropyl-N-(2-methoxyquinolin-3-yl)aminocarbonyl]-4-(3,5-dimethylphenyl)piperazine 1-[(2-Methoxyquinolin-3-yl)aminocarbonyl]-4-(3,5-dimethylphenyl)piperazine was reacted by the same way with the example 100 to obtain the titled compound.

yield: 84% m.p.: 114–115° C.

$^1$H NMR (CDCl$_3$): δ 1.21(6H,d), 2.20(6H,s), 2.77(4H,t), 3.28(4H,t), 4.08(3H,s), 4.39(1H,m), 6.37(2H,s), 6.46(1H,s), 7.41(1H,t), 7.63(1H,t), 7.69(1H,d), 7.75(1H,s), 7.83(1H,d)

EXAMPLE 106

1-[N-Benzyl-N-(2-methoxyquinolin-3-yl)aminocarbonyl]-4-(3,5-dimethylphenyl)piperazine 1-[(2-Methoxyquinolin-3-yl)aminocarbonyl]-4-(3,5-dimethylphenyl)piperazine was reacted by the same way with the example 102 to obtain the titled compound.

yield: 90% m.p.: oil phase $^1$H NMR (CDCl$_3$): δ 2.24(6H,s), 2.87(4H,t), 3.31(4H,t), 4.13(3H,s), 4.80(2H,s), 6.42(3H,s), 7.49(1H,t), 7.62(2H,m), 7.72(2H,m)

EXAMPLE 107

1-[N-(2-Methoxyquinolin-3-yl)-N-methylaminocarbonyl]-4-(3-isopropoxyphenyl)piperazine 1-[(2-Methoxyquinolin-3-yl)aminocarbonyl]-4-(3-isopropoxylphenyl)piperazine was reacted by the same way with the example 98 to obtain the titled compound.

yield: 92% m.p.: oil phase $^1$H NMR (CDCl$_3$): δ 1.28(6H,d), 2.97(4H,t), 3.18(3H,s), 3.37(4H,t), 4.14(3H,s), 4.49(1H,m), 6.41(3H,m), 7.13(1H,m), 7.40(1H,t), 7.62(1H,t), 7.66(1H,d), 7.74(1H,s), 7.84(1H,d)

EXAMPLE 108

1-[N-Ethyl-N-(2-methoxyquinolin-3-yl)aminocarbonyl]-4-(3-isopropoxyphenyl)piperazine 1-[(2-Methoxyquinolin-3-yl)aminocarbonyl]-4-(3-isopropoxyphenyl)piperazine was reacted by the same way with the example 99 to obtain the titled compound.

yield: 87% m.p.: oil phase $^1$H NMR (CDCl$_3$): δ 1.16(3H,t), 1.34(6H,d), 2.89(4H,t), 3.30(4H,t), 3.63(2H,m), 4.13(3H,s), 4.55(1H,m), 6.49(2H,s), 7.05(1H,s), 7.20(1H,t), 7.32(1H,s), 7.37(1H,t), 7.50(1H,t), 7.70(1H,d), 7.77(1H,d), 8.80(1H,s)

EXAMPLE 109

1-[(2-Methoxyquinolin-3-yl)aminothiocarbonyl]-4-(3,5-dimethoxyphenyl)piperazine

Phenyl N-(2-methoxyquinolin-3-yl)thiocarbamate(56 mg, 0.5 mmol) and 1-(3,5-dimethoxyphenyl)piperazine(111 mg, 0.5 mmol) were dissolved in anhydrous tetrahydrofuran and DBU(117 mg, 0.75 mmol) was added. The reaction solution was stirred at room temperature for 2 hours. The above solution was concentrated under the reduced pressure to remove tetrahydrofuran and concentrated was purified by column chromatography(Hexane:ether=5:1) to obtain the titled compound.

yield: 76% m.p.: 171–172° C.

$^1$H NMR (CDCl$_3$): δ 3.41(4H,t), 3.81(6H,s), 4.17(3H,s), 4.21(4H,t), 6.12(1H,s), 6.20(1H,d), 7.38(1H,t), 7.54(1H,t), 7.74(1H,d), 7.81(1H,d), 8.96(1H,s)

EXAMPLE 110

1[(2-Methoxyquinolin-3-yl)aminothiocarbonyl]-4-(3,5-dimethylphenyl)piperazine

Phenyl N-(2-methoxyquinolin-3-yl)thiocarbamate and 1-(3,5-dimethylphenyl)piperazine were reacted by the same way with the example 109 to obtain the titled compound.

yield: 79% m.p.: 170–171° C.

¹H NMR (CDCl₃): δ 2.30(6H,s), 3.38(4H,t), 4.09(3H,s), 4.17(4H,t), 6.63(3H,m), 7.38(1H,t), 7.54(1H,t), 7.72(1H,d), 7.81(1H,d), 8.96(1H,s)

EXAMPLE 111

1-[(2-Methoxyquinolin-3-yl)aminothiocarbonyl]-4-(3,5-difluorophenyl)piperazine

Phenyl N-(2-methoxyquinolin-3-yl)thiocarbamate and 1-(3,5-difluorophenyl)piperazine were reacted by the same way with the example 109 to obtain the titled compound.

yield: 78% m.p.: 140–142° C.

¹H NMR (CDCl₃): δ 3.44(4H,t), 4.20(4H,t), 4.25(3H,s), 6.33(2H,m), 6.45(1H,d), 7.41(1H,t), 7.56(1H,m), 7.72(1H,m), 7.97(1H,m), 8.96(1H,s)

EXAMPLE 112

1-[(2-Methoxyquinolin-3-yl)aminothiocarbonyl]-4-(3,5-dichlorophenyl)piperazine

Phenyl N-(2-methoxyquinolin-3-yl)thiocarbamate and 1-(3,5-dichlorophenyl)piperazine were reacted by the same way with the example 109 to obtain the titled compound.

yield: 62% m.p).: 181–183° C.

¹H NMR (CDCl₃): δ 3.44(4H,t), 4.20(4H,t), 4.26(3H,s), 6.77(1H,s), 6.88(2H,t), 7.41(1H,t), 7.59(1H,t), 7.70(2H,m), 8.01(1H,t), 8.11(1H,s), 8.93(1H,s)

EXAMPLE 113

1-[(2-Methoxyquinolin-3-yl)aminothiocarbonyl]-4-(3-methoxyphenyl)piperazine

Phenyl N-(2-methoxyquinolin-3-yl)thiocarbamate and 1-(3-methoxyphenyl)piperazine were reacted by the same way with the example 109 to obtain the titled compound.

yield: 81% m.p.: oil phase

¹H NMR (CDCl₃): δ 3.17(4H,t), 3.89(3H,s), 4.17(4H,t), 6.90(4H,m), 7.34(1H,t), 7.48(1H,t), 7.70(1H,d), 7.77(1H,d), 8.80(1H,s)

EXAMPLE 114

1-[(2-Methylquinolin-3-yl)aminocarbonyl]-4-(3,5-dimethoxyphenyl)piperazine a) Phenyl N-(2-methylquinolin-3-yl)carbamate 3-amino-2-methylquinoline(4 g, 25 mmol) and phenyl chloroformate(4.04 g, 25 mmol) were dissolved in methylene chloride and then was stirred at room temperature for 2 hrs. The mixture solution was concentrated under the reduced pressure to remove methylene chloride and purified by column chromatography(ethylacetate:hexane=1:10) to obtain the titled compound.

yield: 88%

¹H NMR (CDCl₃): δ 2.77(3H,s), 7.30–7.53(9H,m), 8.67(1H,s)

b) 1-[(2-Methylquinolin-3-yl)aminocarbonyl]-4-(3,5-dimethoxyphenyl)piperazine

Phenyl N-(2-methylquinolin-3-yl)carbamate(140 mg, 0.5 mmol) and 1-(3,5-dimethoxyphenyl)piperazine(112 mg, 0.5 mmol) were dissolved in tetrahydrofuran and DBU(117 mg, 0.75 mmol) was added and then the mixture was stirred at room temperature for 2 hrs. The above solution was concentrated under the reduced pressure to remove tetrahydrofuran and purified by column chromatography (ethylacetate:hexane=1:2) to obtain the titled compound.

yield: 84% m.p.: 199–200° C.

¹H NMR (CDCl₃): δ 2.81(3H,s), 3.30(4H,t), 3.76(4H,t), 3.80(6H,s), 6.08(1H,s), 6.12(2H,d), 7.48(1H,t), 7.62(1H,t), 7.71(1H,d), 8.03(1H,d), 8.59(1H,s)

EXAMPLE 115

1-[(2-Methylquinolin-3-yl)aminocarbonyl]-4-(3,5-dimethylphenyl)piperazine

Phenyl N-(2-methylquinolin-3-yl)carbamate and 1-(3,5-dimethylphenyl)piperazine were reacted by the same way with the example 114 to obtain the titled compound.

yield: 86% m.p.: 230–232° C.

¹H NMR (CDCl₃): δ 2.31(6H,s), 2.82(3H,s), 3.29(4H,t), 3.76(4H,t), 6.60(3H,s), 7.49(1H,t), 7.63(1H,t), 7.73(1H,d), 8.05(1H,d), 8.61(1H,s)

EXAMPLE 116

1-[(2-methylquinolin-3-yl)aminocarbonyl]-4-(2,3-dimethyliphenyl)piperazine

Phenyl N-(2-methylquinolin-3-yl)carbamate and 1-(2,3-dimethylphenyl)piperazine were reacted by the same way with the example 114 to obtain the titled compound.

yield: 81% m.p.: 169–170° C.

¹H NMR (CDCl₃): δ 2.28(6H,d), 2.84(3H,s), 3.00(4H,t), 3.76(4H,t), 6.94(2H,m), 7.11(1H,t), 7.49(1H,t), 7.63(1H,t), 7.72(1H,d), 8.07(1H,d), 8.64(1H,s)

EXAMPLE 117

1-[(2-Methoxyquinolin-3-yl)aminocarbonyl]-4-(3,5-difluorophenyl)piperazine

Phenyl N-(2-methylquinolin-3-yl)carbamate and 1-(3,5-difluorophenyl)piperazine were reacted by the same way with the example 114 to obtain the titled compound.

yield: 81% m.p.: 238–240° C.

¹H NMR (CDCl₃): δ 2.81(3H,t), 3.34(4H,t), 3.77(4H,t), 6.32(1H,t), 6.39(2H,d), 7.49(1H,t), 7.63(1H,t), 7.72(1H,d), 8.03(1H,d), 8.58(1H,s)

EXAMPLE 118

1-[(2-Methylquinolin-3-yl)aminocarbonyl]-4-(3,5-dichlorophenyl)piperazine

Phenyl N-(2-methylquinolin-3-yl)carbamate and 1-(3,5-dichlorophenyl)piperazine were reacted by the same way with the example 114 to obtain the titled compound.

yield: 65% m.p.: 247–249° C.

¹H NMR (CDCl₃): δ 2.79(3H,s), 3.33(4H,t), 3.75(4H,t), 6.78(2H,s), 6.87(1H,s), 7.49(1H,t), 7.63(1H,t), 7.72(1H,d), 8.56(1H,s)

EXAMPLE 119

1-[(2-Methylquinolin-3-yl)aminocarbonyl]-4-(2-methoxyphenyl)piperazine

Phenyl N-(2-methylquinolin-3-yl)carbamate and 1-(2-methoxyphenyl)piperazine were reacted by the same way with the example 114 to obtain the titled compound.

yield: 83% m.p.: 135–136° C.

$^1$H NMR (CDCl$_3$): δ 2.82(3H,s), 3.18(4H,t), 3.79(4H,t), 3.91(3H,s), 6.88(1H,d), 6.97(2H,s), 7.07(1H,m), 7.48(1H,t), 7.62(1H,t), 7.72(1H,d), 8.04(1H,d), 8.63(1H,s)

EXAMPLE 120

1-[(2-Methylquinolin-3-yl)aminocarbonyl]-4-(2-fluorophenyl)piperazine

Phenyl N-(2-methylquinolin-3-yl)carbamate and 1-(2-fluorophenyl)piperazine were reacted by the same way with the example 114 to obtain the titled compound.

yield: 84% m.p.: 201–203° C.

$^1$H NMR (CDCl$_3$): δ 2.84(3H,s), 3.20(4H,t), 3.80(4H,t), 6.99(2H,m), 7.07(2H,m), 7.49(1H,t), 7.62(1H,t), 7.71(1H,d), 8.04(1H,d), 8.62(1H,s)

EXAMPLE 121

1-[(2-Methylquinolin-3-yl)aminocarbonyl]-4-(2-chlorophenyl)piperazine

Phenyl N-(2-methylquinolin-3-yl)carbamate and 1-(2-chlorophenyl)piperazine were reacted by the same way with the example 114 to obtain the titled compound.

yield: 72% m.p.: 180–181° C.

$^1$H NMR (CDCl$_3$): δ 2.83(3H,s), 3.16(4H,t), 3.80(4H,t), 7.04(3H,m), 7.40(1H,d), 7.49(1H,t), 7.63(1H,t), 7.71(1H,d), 8.05(1H,d), 8.62(1H,s)

EXAMPLE 122

1-[(2-Methylquinolin-3-yl)aminocarbonyl]-4-(2-methylthiophenyl)piperazine

Phenyl N-(2-methylquinolin-3-yl)carbamate and 1-(2-methylthiophenyl)piperazine were reacted by the same way with the example 114 to obtain the titled compound.

yield: 76% m.p.: 165–166° C.

$^1$H NMR (CDCl$_3$): δ 2.45(3H,s), 2.85(3H,s), 3.11(4H,t), 3.79(4H,t), 7.05(1H,m), 7.15(3H,d), 7.49(1H,t), 7.63(1H,t), 7.69(1H,d), 8.07(1H,d), 8.62(1H,s)

EXAMPLE 123

1-[(2-Methylquinolin-3-yl)aminocarbonyl]-4-(2-methoxy-5-methylphenyl)piperazine

Phenyl N-(2-methylquinolin-3-yl)carbamate and 1-(2-methoxy-5-methylphenyl)piperazine were reacted by the same way with the example 114 to obtain the titled compound.

yield: 80% m.p.: oil phase $^1$H NMR (CDCl$_3$): δ 2.30(3H,s), 2.72(3H,s), 3.17(4H,t), 3.70(4H,t), 3.87(3H,s), 6.77(1H,s), 6.82(2H,s), 7.73(4H,m), 8.60(1H,s)

EXAMPLE 124

1-[(2-Methylquinolin-3-yl)aminocarbonyl]-4-(1-naphthyl)piperazine

Phenyl N-(2-methylquinolin-3-yl)carbamate and 1-(1-naphthyl)piperazine were reacted by the same way with the example 114 to obtain the titled compound.

yield: 64% m.p.: 220–222° C.

$^1$H NMR (CDCl$_3$): δ 2.83(3H,s), 3.23(4H,t), 3.80(4H,t), 6.91(1H,s), 7.12(1H,d), 7.44(1H,d), 7.50(3H,m), 7.61(2H,m), 7.73(1H,d), 7.86(1H,d), 8.05(1H,d), 8.23(1H,d), 8.64(1H,s)

EXAMPLE 125

1-[(2-Methylquinolin-3-yl)aminothiocarbonyl]-4-(3,5-dimethoxyphenyl)piperazine a) Phenyl N-(2-methylquinolin-3-yl)thiocarbamate 3-Amino-2-methylquinoline(4 g, 25 mmol) and phenyl chlorothionoformate(4.32 g, 25 mmol) were dissolved in methylene chloride and then was stirred at room temperature for 2 hours. The mixture solution was concentrated under reduced pressure to remove methylene chloride and purified by column chromatography(ethylacetate:hexane=1:2) to obtain the titled compound.

yield: 78%

$^1$H NMR (CDCl$_3$): δ 2.77(3H,s), 7.09–7.90(9H,m), 9.14(1H,s)

b) 1-[(2-Methylquinolin-3-yl)aminothiocarbonyl]-4-(3,5-dimethoxyphenyl)piperazine Phenyl N-(2-methylquinolin-3-yl)thiocarbamate(147 mg, 0.5 mmol) and 1-(3,5-dimethoxyphenyl)piperazine(112 mg, 0.5 mmol) were dissolved in anhydrous tetrahydrofuran and DBU(117 mg, 0.75 mmol) was added and then the mixture was stirred at room temperature for 2 hrs. The above solution was concentrated under the reduced pressure to remove tetrahydrofuran and purified by column chromatography (ethylacetate:hexane=1:2) to obtain the titled compound.

yield: 86% m.p.: 211–212° C.

$^1$H NMR (CDCl$_3$): δ 2.81(3H,s), 3.35(4H,t), 3.79(6H,s), 4.14(4H,t), 6.07(3H,s), 7.49(2H,t), 7.68(2H,m), 8.01(1H,s), 8.07(1H,d)

EXAMPLE 126

1-[(2-Methylquinolin-3-yl)aminothiocarbonyl]-4-(3,5-dimethylphenyl)piperazine

Phenyl N-(2-methylquinolin-3-yl)thiocarbamate and 1-(3,5-dimethylphenyl)piperazine were reacted by the same way with the example 125 to obtain the titled compound.

yield: 81% m.p.: 196–197° C.

$^1$H NMR (CDCl$_3$): δ 2.27(6H,s), 2.81(3H,s), 3.31(4H,t), 4.11(4H,t), 6.53(2H,s), 6.58(1H,s), 7.48(2H,t), 7.67(2H,m), 7.96(1H,s), 8.04(1H,d)

EXAMPLE 127

1-[(2-Methylquinolin-3-yl)aminothiocarbonyl]-4-(3,5-difluorophenyl)piperazine

Phenyl N-(2-methylquinolin-3-yl)thiocarbamate and 1-(3,5-difluorophenyl)piperazine were reacted by the same way with the example 125 to obtain the titled compound.

yield: 74% m.p.: 211–213° C.

$^1$H NMR (CDCl$_3$): δ 2.85(3H,s), 3.43(4H,t), 4.22(4H,t), 6.33(2H,m), 7.49(1H,t), 7.64(1H,d), 7.72(1H,t), 8.16(2H,m)

EXAMPLE 128

1-{[2-(Pyridin-2-yl)quinolin-4-yl]aminocarbonyl}-4-(3,5-dimethoxyphenyl)piperazine Phenyl N-[2-(pyridin-3-yl)quinolin-4-yl]carbamate(171 mg, 0.5 mmol) and 1-(3,5-dimethoxyphenyl)piperazine(111 mg, 0.5 mmol) were dissolved in anhydrous tetrahydrofuran and DBU(117 mg, 0.75 mmol) was added and then the mixture was stirred at room temperature for 2 hrs. The above solution was concentrated under the reduced pressure to remove tetrahydrofuran and purified by column chromatography (dichloromethane:methanol=20:1) to obtain the titled compound.

yield: 73% m.p.: 97–98° C.

$^1$H NMR (CDCl$_3$): δ 3.34(4H,t), 3.79(6H,s), 3.90(4H,t), 6.07(1H,s), 6.12(2H,s), 7.43(1H,t), 7.50(1H,t), 7.68(1H,t), 7.93(1H,t), 8.26(1H,d), 8.59(1H,d), 8.80(1H,d), 8.98(1H,s)

Mass(EI) m/z: Calcd for C$_{31}$H$_{27}$N$_5$O$_3$ 517.2113, found 517.3244

EXAMPLE 129

1-{[2-(Pyridin-3-yl)quinolin-4-yl]aminocarbonyl}-4-(3,5-dimethoxyphenyl)piperazine Phenyl N-[2-pyridin-3-yl)quinolin-4-yl]carbamate(171 mg, 0.5 mmol) and 1-(3,5-dimethoxyphenyl)piperazine(111 mg, 0.5 mmol) were dissolved in anhydrous tetrahydrofuran and DBU(117 mg, 0.75 mmol) was added and then the mixture was stirred at room temperature for 2 hours. The above solution was concentrated under the reduced pressure to remove tetrahydrofuran and purified by column chromatography (dichloromethane:methanol=20:1) to obtain the titled compound.

yield: 67% m.p.: 95–96° C.

$^1$H NMR (CDCl$_3$): δ 3.36(4H,t), 3.87(6H,s), 3.90(4H,t), 6.08(1H,s), 6.12(2H,s), 7.50(1H,t), 7.71(1H,t), 7.93(1H,t), 8.25(1H,d), 8.53(1H,d), 8.67(1H,d), 8.73(1H,d), 9.35(1H,s)

EXAMPLE 130

1-{[2-Thien-2-yl)quinolin-4-yl]aminocarbonyl}-4-(3,5-dimethoxyphenyl)piperazine

Phenyl N-[2-(thien-2-yl)quinolin-4-yl]carbamate(173 mg, 0.5 mmol) and 1-(3,5-dimethoxyphenyl)piperazine(111 mg, 0.5 mmol) were dissolved in anhydrous tetrahydrofuran and DBU(117 mg, 0.75 mmol) was added. The resulting mixture was stirred at room-temperature for 2 hours, concentrated under the reduced pressure to remove tetrahydrofuran and purified by column chromatography (ethylaetate:hexane=1:1) to obtain the titled compound.

yield: 61% m.p.: oil phase $^1$H NMR (CDCl$_3$): δ 3.37(4H,t), 3.59(6H,s), 3.97(4H,t), 7.01(3H,m), 7.49(1H,t), 7.69(1H,t), 7.93(1H,t), 8.20(1H,d), 8.52(1H,d), 8.64(1H,s), 8.71(1H,d), 9.35(1H,s)

EXAMPLE 131

1-{[2-(Pyridin-3-yl)quinolin-4-yl]aminocarbonyl}-4-(3,5-dimethylphenyl)piperazine Phenyl N-[2-(pyridin-3-yl)quinolin-4-yl]carbamate(171 mg, 0.5 mmol) and 1-(3,5-dimethylphenyl)piperazine(95 mg, 0.5 mmol) were dissolved in anhydrous tetrahydrofuran and DBU(117 mg, 0.75 mmol) was added. The resulting mixture was stirred at room temperature for 2 hours, concentrated under the reduced pressure to remove tetrahydrofuran, and purified by column chromatography (ethylacetate:hexane=1:1) to obtain the titled compound.

yield: 64% m.p.: 211–213° C.

$^1$H NMR (CDCl$_3$): δ 2.31(6H,s), 3.32(4H,t), 3.85(4H,t), 6.61(3H,s), 7.47(1H,t), 7.55(1H,t), 7.72(1H,t), 7.86(1H,t), 8.25(1H,d), 8.53(1H,d), 8.66(1H,s), 8.72(1H,d), 9.37(1H,s)

EXAMPLE 132

1-[N-(5,6-Dimethyl-2-methoxypyridin-3-yl)-N-methylaminocarbonyl]-4-(3,5-dimethoxyphenyl) piperazine 1-[(5,6-Dimethyl-2-methoxypyridin-3-yl) aminocarbonyl]-4-(3,5-dimethoxyphenyl)piperazine(100 mg, 0.25 mmol) was dissolved in dimethylformamide(15 ml) and thereto sodium hydride(6.0 mg, 0.25 mmol) was added. The resulting mixture was stirred at room temperature for 15 min and thereto iodomethane(35 mg, 0.25 mmol) was added. The resulting mixture was stirred at room temperature for 16 hrs, concentrated under the reduced pressure to remove dimethylformamide, and purified by column chromatography(ethylacetate:hexane=1:2) to obtain the titled compound.

yield: 94% m.p.: oil phase $^1$H NMR(CDCl$_3$) δ: 2.17(3H,s), 2.38(3H,s), 2.92(4H,t), 3.04(3H,s), 3.29(4H,t), 3.74(6H,s), 3.96(3H,s), 6.00(3H,m), 7.08(1H,s)

EXAMPLE 133

1-[N-Ethyl-N-(5,6-dimethyl-2-methoxypyridin-3-yl) aminocarbonyl]-4-(3,5-dimethoxyphenyl)piperazine 1-[(5,6-Dimethyl-2-methoxypyridin-3-yl) aminocarbonyl]-4-(3,5-dimethoxyphenyl)piperazine(100 mg, 0.25 mmol) was dissolved in dimethylformamide(15 ml) and thereto sodium hydride(6.0 mg, 0.25 mmol) was added, followed by stirring at room temperature for 15 min and then iodoethane(39.2 mg, 0.25 mmol) was added. The resulting mixture was stirred at room temperature for 16 hrs, concentrated under the reduced pressure to remove dimethylformamide, and purified by column chromatography(ethylacetate:hexane=1:2) to obtain the titled compound.

yield: 86% m.p.: oil phase $^1$H NMR(CDCl$_3$) δ: 1.08(3H,t), 2.04(3H,s), 2.38(3H,s), 2.90(4H,t), 3.26(4H,t), 3.52(2H,q), 3.74(6H,s), 5.99(3H,m), 7.06(1H,s)

EXAMPLE 134

1-[N-Isopropyl-N-(5,6-dimethyl-2-methoxypyridin-3-yl)aminocarbonyl]-4-(3,5-dimethoxyphenyl) piperazine 1-[(5,6-Dimethyl-2-methoxypyridin-3-yl) aminocarbonyl]-4-(3,5-dimethoxyphenyl)piperazine(100 mg, 0.25 mmol) was dissolved in dimethylformamide(15 ml) and thereto sodium hydride(6.0 mg, 0.25 mmol) was added, followed by stirring at room temperature for 15 min, and then 2-iodopropane(42 mg, 0.25 mmol) was added. The resulting mixture was stirred at room temperature for 16 hrs, concentrated under the reduced pressure to remove dimethylformamide, purified by column chromatography (ethylacetate:hexane=1:2) to obtain the titled compound.

yield: 78% m.p.: oil phase $^1$H NMR(CDCl$_3$) δ: 1.13(6H,d), 2.19(3H,s), 2.38(3H,s), 2.82(4H,t), 3.26(4H,t), 3.74(6H,s), 3.89(3H,s), 4.27(1H,m), 6.06(1H,s), 6.10(2H,d), 7.07(1H,s), 8.14(1H,s)

Mass(EI) m/z: Calcd for C$_{24}$H$_{34}$N$_4$O$_4$ 442.2580, found 442.2538

EXAMPLE 135

1-[N-(5,6-Dimethyl-2-methoxypyridin-3-yl)-N-methylaminocarbonyl]-4-(3,5-dimethylphenyl) piperazine 1-[(5,6-Dimethyl-2-methoxypyridin-3-yl) aminocarbonyl]-4-(3,5-dimethylphenyl)piperazine was reacted by the same way with the example 132 to obtain the titled compound.

yield: 97% m.p.: oil phase $^1$H NMR(CDCl$_3$) δ: 2.15(6H,s), 2.23(3H,s), 2.37(3H,s), 2.89(4H,t), 3.04(3H,s), 3.30(4H,t), 3.97(3H,s), 6.46(3H,m), 7.08(1H,s)

EXAMPLE 136

1-[N-(5,6-Dimethyl-2-methoxypyridin-3-yl)-N-methylaminocarbonyl]-4-(2-methoxyphenyl) piperazine 1-[(5,6-Dimethyl-2-methoxypyridin-3-yl) aminocarbonyl]-4-(2-methoxylphenyl)piperazine was reacted by the same way with the example 132 to obtain the titled compound.

yield: 94% m.p.: 131–132° C.

$^1$H NMR(CDCl$_3$) δ: 2.16(3H,s), 2.38(3H,s), 2.80(4H,t), 3.05(3H,s), 3.35(4H,t), 3.82(3H,s), 3.97(3H,s), 6.83(4H,m), 7.08(1H,s)

EXAMPLE 137

1-[N-Ethyl-N-(5,6-dimethyl-2-methoxypyridin-3-yl) aminocarbonyl]-4-(2-methoxyphenyl)piperazine 1-[(5,6-Dimethyl-2-methoxypyridin-3-yl) aminocarbonyl]-4-(2-methoxyphenyl)piperazine was reacted by the same way with the example 133 to obtain the titled compound.

yield: 87% m.p.: 112–113° C.

$^1$H NMR(CDCl$_3$) δ: 1.08(3H,t), 2.16(3H,s), 2.38(3H,s), 2.77(4H,t), 3.31(4H,t), 3.58(2H,q), 3.81(3H,s), 3.96(3H,s), 6.88(4H,m), 7.06(1H,s)

EXAMPLE 138

1-[N-Benzyl-N-(5,6-dimethyl-2-methoxypyridin-3-yl)aminocarbonyl]-4-(2-methoxyphenyl)piperazine 1-[(5,6-Dimethyl-2-methoxypyridin-3-yl) aminocarbonyl]-4-(2-methoxyphenyl)piperazine(100 mg, 0.27 mmol) was dissolved in dimethylformamide(15 ml) and thereto sodium hydride(6.5 mg, 0.27 mmol) was added, followed by stirring at room temperature for 1 hr, and successively benzyl bromide(46.2 mg, 0.27 mmol) was added. The resulting mixture was stirred at room temperature for 16 hrs, concentrated under the reduced pressure and purified by column chromatography(ethylacetate:hexane= 1:2) to obtain the titled compound.

yield: 93% m.p.: oil phase $^1$H NMR(CDCl$_3$) δ: 2.08(3H,s), 2.35(3H,s), 2.85(4H,t), 3.32(4H,t), 3.81(3H,s), 3.96(3H,s), 4.76(2H,s), 6.96(4H,m), 7.41(5H,m)

EXAMPLE 139

1-[N-Cyclopropylmethyl-N-(5,6-dimethyl-2-methoxypyridin-3-yl)aminocarbonyl]-4-(2-methoxyphenyl)piperazine 1-[(5,6-Dimethyl-2-methoxypyridin-3-yl) aminocarbonyl]-4-(2-methoxyphenyl)piperazine(100 mg, 0.26 mmol) was dissolved in dimethylformamide(15 ml) and thereto sodium hydride(6.2 mg, 0.26 mmol) was added, followed by stirring at room temperature for 15 min, and successively bromomethylcyclopropane(21.8 mg, 0.26 mmol) was added. The resulting mixture was stirred at room temperature for 16 hrs, concentrated under the reduced pressure and purified by column chromatography (ethylacetate:hexane=1:2) to obtain the titled compound.

yield: 78% m.p.: oil phase $^1$H NMR(CDCl$_3$) δ: 0.34(2H,m), 0.49(2H,m), 1.35(1H, m), 2.85(4H,t), 3.28(4H,t), 3.40(2H,s), 3.89(3H,s), 3.97(3H, s), 6.97(4H,m), 7.11(1H,s)

EXAMPLE 140

1-[N-(5,6-Dimethyl-2-methoxypyridin-3-yl)-N-methylaminocarbonyl]-4-(5-methoxy-2-methylphenyl)piperazine 1-[(5,6-Dimethyl-2-methoxypyridin-3-yl) aminocarbonyl]-4-(5-methoxy-2-methylphenyl)piperazine was reacted by the same way with the example 132 to obtain the titled compound.

yield: 74% m.p.: 91–93° C.

$^1$H NMR(CDCl$_3$) δ: 2.15(3H,s), 2.18(3H,s), 2.39(3H,s), 2.67(4H,t), 3.05(3H,s), 3.30(4H,t), 3.75(3H,s), 3.97(3H,s), 6.48(3H,m), 7.10(1H,s)

EXAMPLE 141

1-[N-Ethyl-N-(5,6-dimethyl-2-methoxypyridin-3-yl) aminocarbonyl]-4-(5-methoxy-2-methylphenyl) piperazine 1-[(5,6-Dimethyl-2-methoxypyridin-3-yl) aminocarbonyl]-4-(5-methoxy-2-methylphenyl)piperazine was reacted by the same way with the example 133 to obtain the titled compound.

yield: 94% m.p.: oil phase $^1$H NMR(CDCl$_3$) δ: 1.09(3H,t), 2.15(3H,s), 2.18(3H,s), 2.39(3H,s), 2.60(4H,t), 3.27(4H,t), 3.59(2H,q), 3.75(3H,s), 3.96(3H,s), 6.45(3H m), 7.08(1H,s)

EXAMPLE 142

1-[N-Benzyl-N-(5,6-dimethyl-2-methoxypyridin-3-yl)aminocarbonyl]-4-(5-methoxy-2-methylphenyl)piperazine 1-[(5,6-Dimethyl-2-methoxypyridin-3-yl)aminocarbonyl]-4-(5-methoxy-2-methylphenyl)piperazine was reacted by the same way with the example 138 to obtain the titled compound.

yield: 97% m.p.: oil phase $^1$H NMR(CDCl$_3$) δ: 1.25(3H,t), 2.08(3H,s), 2.14(3H,s), 2.35(3H,s), 2.60(4H,t), 3.32(4H,t), 3.74(3H,s), 3.95(3H,s), 4.66(2H,s), 6.44(4H,m), 6.96(5H,m), 7.12(1H,s)

EXAMPLE 143

1-[N-(5-Ethyl-2-methoxy-6-methylpyridin-3-yl)-N-methylaminocarbonyl]-4-(3,5-dimethoxyphenyl)piperazine 1-[(5-Ethyl-2-methoxy-6-methylpyridin-3-yl)aminocarbonyl]-4-(3,5-dimethoxyphenyl)piperazine was reacted by the same way with the example 132 to obtain the titled compound.

yield: 87% m.p.: 78–79° C.

$^1$H NMR(CDCl$_3$) δ: 1.14(3H,t), 2.41(3H,s), 2.52(2H,q), 2.91(4H,t), 3.02(3H,s), 3.28(4H,t), 3.74(6H,s), 3.98(3H,s), 5.98(3H,m), 7.11(1H,s)

Mass(EI) m/z: Calcd for C$_{23}$H$_{32}$N$_4$O$_4$ 428.2423, found 428.2434

EXAMPLE 144

1-[N-(5-Ethyl-2-methoxy-6-methylpyridin-3-yl)-N-methylaminocarbonyl]-4-(3,5-dimethylphenyl)piperazine 1-[(5-Ethyl-2-methoxy-6-methylpyridin-3-yl)aminocarbonyl]-4-(3,5-dimethylphenyl)piperazine was reacted by the same way with the example 132 to obtain the titled compound.

yield: 84% m.p.: 86–87° C.

$^1$H NMR(CDCl$_3$) δ: 1.14(3H,t), 2.23(6H,s), 2.45(3H,s), 2.58(2H,q), 2.87(4H,t), 3.05(3H,s), 3.30(4H,t), 3.98(3H,s), 6.46(3H,m), 7.11(1H,s)

Mass(EI) m/z: Calcd for C$_{23}$H$_{32}$N$_4$O$_2$ 396.2525, found 396.2575

EXAMPLE 145

1-[N-Ethyl-N-(5-ethyl-2-methoxy-6-methylpyridin-3-yl)aminocarbonyl]-4-(3,5-dimethylphenyl)piperazine 1-[(5-Ethyl-2-methoxy-6-methylpyridin-3-yl)aminocarbonyl]-4-(3,5-dimethylphenyl)piperazine was reacted by the same way with the example 133 to obtain the titled compound.

yield: 86% m.p.: 84–85° C.

$^1$H NMR(CDCl$_3$) δ: 1.13(6H,m), 2.23(6H,s), 2.41(3H,s), 2.58(2H,q), 2.85(4H,t), 3.26(4H,t), 3.46(2H,q), 3.96(3H,s), 6.45(3H,m), 7.08(1H,s)

EXAMPLE 146

1-[N-(2-Methoxy-6-methyl-5-propylpyridin-3-yl)-N-methylaminocarbonyl]-4-(3,5-dimethoxyphenyl)piperazine 1-[(2-Methoxy-6-methyl-5-propylpyridin-3-yl)aminocarbonyl]-4-( 3,5-dimethylphenyl)piperazine was reacted by the same way with the example 132 to obtain the titled compound.

yield: 89% m.p.: oil phase $^1$H NMR(CDCl$_1$) δ: 1.01(3H,t), 1.78(2H,m), 2.21(3H,s), 2.78(2H,t), 3.78(6H,s), 3.86(4H,t), 3.99(3H,s), 4.00(3H,s), 4.22(4H,t), 6.01(3H,m), 7.02(1H,s)

EXAMPLE 147

1-[N-(6-Ethyl-2-methoxy-5-methylpyridin-3-yl)-N-methylaminocarbonyl]-4-(3,5-dimethoxyphenyl)piperazine 1-[(6-Ethyl-2-methoxy-5-methylpyridin-3-yl)aminocarbonyl]-4-(3,5-dimethoxyphenyl)piperazine was reacted by the same way with the example 132 to obtain the titled compound.

yield: 85% m.p.: oil phase $^1$H NMR(CDCl$_3$) δ: 2.21(3H,t), 2.21(3H,s), 2.45(2H,q), 3.21(4H,t), 3.40(3H,s), 3.67(4H,t), 3.77(6H,s), 4.01(3H,s), 6.07(3H,m), 6.96(1H,s), 8.07(1H,s)

EXAMPLE 148

1-[N-(2-Methoxy-5-methyl-6-propylpyridin-3-yl)-N-methylaminocarbonyl]-4-(3,5-dimethoxyphenyl)piperazine 1-[(2-Methoxy-5-methyl-6-propylpyridin-3-yl)aminocarbonyl]-4-(3,5-dimethoxyphenyl)piperazine was reacted by the same way with the example 132 to obtain the titled compound.

yield: 86% m.p.: 106–107° C.

$^1$H NMR(CDCl$_3$) δ: 0.98(3H,t), 1.73(2H,q), 2.18(3H,s), 2.63(2H,t), 2.92(4H,t), 3.05(3H,s), 3.29(4H,t), 3.74(6H,s), 3.96(3H,s), 6.00(3H,m), 7.11 (1H,s)

Mass(EI) m/z: Calcd for C$_{24}$H$_{34}$N$_4$O$_4$ 442.2580, found 442.2543

EXAMPLE 149

1-[N-(5-Acetyl-2-methoxy-6-methylpyridin-3-yl)-N-methylaminocarbonyl]-4-(3,5-dimethoxyphenyl)piperazine 1-[(5-Acetyl-2-methoxy-6-methylpyridin-3-yl)aminocarbonyl]-4-(3,5-dimethylphenyl)piperazine was reacted by the same way with the example 132 to obtain the titled compound.

yield: 89% m.p.: oil phase $^1$H NMR(CDCl$_3$) δ: 2.50(3H,s), 2.70(3H,s), 2.97(4H,t), 3.09(3H,s), 3.33(4H,t), 3.75(6H,s), 4.06(3H,s), 6.03(3H,m), 7.72(1H,s)

Mass(EI) m/z: Calcd for C$_{23}$H$_{30}$N$_4$O$_5$ 442.2216, 442.2229

EXAMPLE 150

1-[N-Ethyl-N-(5-acetyl-2-methoxy-6-methylpyridin-3-yl)aminocarbonyl]-4-(3,5-dimethoxyphenyl)piperazine 1-[(5-Acetyl-2-methoxy-6-methylpyridin-3-yl)aminocarbonyl]-4-(3,5-dimethoxyphenyl)piperazine was reacted by the same way with the example 133 to obtain the titled compound.

yield: 87% m.p.: oil phase $^1$H NMR(CDCl$_3$) δ: 1.09(3H,t), 2.49(3H,s), 2.70(3H,s), 3.00(4H,t), 3.32(4H,t), 3.77(6H,s), 4.01(3H,s), 4.09(2H,q), 5.98(3H,m), 7.76(1H,s)

EXAMPLE 151

1-[N-(5-Acetyl-2-methoxy-6-methylpyridin-3-yl)-N-methylaminocarbonyl]-4-(3,5-dimethylphenyl)piperazine 1-[(5-Acetyl-2-methoxy-6-methylpyridin-3-yl)aminocarbonyl]-4-(3,5-dimethylphenyl)piperazine was reacted by the same with the example 132 to obtain the titled compound.

yield: 88% m.p.: oil phase $^1$H NMR(CDCl$_3$) δ: 2.24(6H,s), 2.50(3H,s), 2.70(3H,s), 2.93(4H,t), 3.09(3H,s), 3.28(4H,t), 4.06(3H,s), 6.46(3H,m), 7.73(1H,s)

EXAMPLE 152

1-{N-[5-(1-Hydroxyethyl)-2-methoxy-6-methylpyridin-3-yl]-N-methylaminocarbonyl}-4-(3,5-dimethoxyphenyl)piperazine 1-[N-(5-Acetyl-2-methoxy-6-methylpyridin-3-yl)-N-methylaminocarbonyl]-4-(3,5-dimethoxyphenyl)piperazine (0.47 mmol) was dissolved in anhydrous ethanol(15 ml) and thereto sodium borohydride(17.3 mg) was added, then followed by stirring at room temperature for 2 hrs. The resulting mixture was concentrated under the reduced pressure to remove ethanol and purified by column chromatography(ethylacetate:hexane=2:1) to obtain the titled compound.

yield: 97% m.p.: oil phase $^1$H NMR(CDCl$_3$) δ: 1.14(3H,d), 2.44(3H,s), 2.93(4H,t), 3.06(3H,s), 3.30(4H,t), 3.74(6H,s), 3.98(3H,s), 5.03(1H,q), 6.02(3H,m), 7.50(1H,s)

EXAMPLE 153

1-{N-Ethyl-N-[5-(1-hydroxyethyl)-2-methoxy-6-methylpyridin-3-yl]aminocarbonyl}-4-(3,5-dimethoxyphenyl)piperazine 1-[N-Ethyl-N-(5-cetyl-2-methoxy-6-methylpyridin-3-yl)aminocarbonyl]-4-(3,5-dimethoxyphenyl)piperazine was reacted by the same way with the example 152 to obtain the titled compound.

yield: 96% m.p.: oil phase $^1$H NMR(CDCl$_3$) δ: 1.09(3H,t), 1.41(3H,d), 2.44(3H,s), 2.91(4H,t), 3.27(4H,t), 3.54(1H,q), 3.74(6H,s), 3.96(3H,s), 5.03(1H,q), 6.02(3H,m), 8.46(1H,s)

EXAMPLE 154

1-{N-[5-(1-Hydroxyethyl)-2-methoxy-6-methylpyridin-3-yl]-N-methylaminocarbonyl]-4-(3,5-dimethylphenyl)piperazine 1-[N-Methyl-N-(5-acetyl-2-methoxy-6-methylpyridin-3-yl)aminocarbonyl]-4-(3,5-dimethylphenyl)piperazine was reacted by the same way with the example 152 to obtain the titled compound.

yield: 97% m.p.: oil phase $^1$H NMR(CDCl$_3$) δ: 1.41(3H,d), 2.24(6H,s), 2.44(3H,s), 2.91(4H,t), 3.06(3H,s), 3.26(4H,t), 3.99(3H,s), 5.03(1H,q), 6.49(3H,m), 7.50(1H,s)

EXAMPLE 155

1-{N-[5-(1-Hydroxy-1-methylethyl)-2-methoxy-6-methylpyridin-3-yl]-N-methylaminocarbonyl}-4-(3,5-dimethoxyphenyl)piperazine 1-[N-Methyl-N-(5-acetyl-2-methoxy-6-methylpyridin-3-yl)aminocarbonyl]-4-(3,5-dimethoxyphenyl)piperazine(221 mg, 0.5 mmol) was dissolved in tetrahydrofuran(10 ml) and thereto methyl magnesium bromide(0.50 ml, 1.50 mmol). The resulting mixture was refluxed for 15 hrs, concentrated under the reduced pressure to remove used solvent, extracted with ethylacetate, filtered to dryness, and purified by column chromatography(ethylacetate:hexane=1:2) to obtain the titled compound.

yield: 92% m.p.: oil phase $^1$H NMR(CDCl$_3$) δ: 1.59(6H,s), 2.66(3H,s), 2.93(4H,t), 3.06(3H,s), 3.30(4H,t), 3.74(6H,s), 3.99(3H,s), 6.03(3H,m), 7.45(1H,s)

EXAMPLE 156

1-{N-[5-(1-Hydroxy-1-methylpropyl)-2-methoxy-6-methylpyridin-3-yl]-N-methylaminocarbonyl}-4-(3,5-dimethylphenyl)piperazine 1-[N-Methyl-N-(5-acetyl-2-methoxy-6-methylpyridin-3-yl)aminocarbonyl]-4-(3,5-dimethylphenyl)piperazine(213 mg, 0.5 mmol) was dissolved in tetrahydrofuran(10 ml) and thereto methyl magnesium bromide(0.50 ml, 1.50 mmol) was added slowly, then refluxed for 15 hrs. The resulting mixture was concentrated under the reduced pressure to remove the used solvent, extracted with ethylacetate, filtered to dryness, and purified by column chromatography (ethylacetate:hexane=1:2) to obtain the titled compound.

yield: 88% m.p).: oil phase $^1$H NMR(CDCl$_3$) δ: 0.79(3H,t), 1.58(3H,s), 1.85(2H,q), 2.61(3H,s), 2.99(4H,t), 3.07(3H,s), 3.30(4H,t), 3.76(6H,s), 6.12(3H,m), 7.47(1H,s)

EXAMPLE 157

1-{N-[2-Methoxy-5-(1-methoxyethyl)-6-methylpyridin-3-yl]-N-methylaminocarbonyl}-4-(3,5-dimethoxyphenyl)piperazine 1-{N-[5-(1-Hydroxyethyl)-2-methoxy-6-methylpyridin-3-yl]aminocarbonyl}-4-(3,5-dimethoxyphenyl)piperazine was reacted by the same way with the example 132 to obtain the titled compound.

yield: 95% m.p.: 117–119° C.

$^1$H NMR(CDCl$_3$) δ: 1.34(3H,t), 2.43(3H,s), 2.94(4H,t), 3.06(3H,s), 3.18(3H,s), 3.30(4H,t), 3.74(6H,s), 3.99(3H,s), 4.44(1H,q), 6.02(3H,m), 7.37(1H,s)

EXAMPLE 158

1-[N-(2-Methoxy-6-methyl-5-vinylpyridin-3-yl)-N-methylaminocarbonyl]-4-(3,5-dimethoxyphenyl)piperazine 1-[(2-Methoxy-6-methyl-5-vinylpyridin-3-yl)aminocarbonyl]-4-(3,5-dimethoxyphenyl)piperazine was reacted by the same way with the example 132 to obtain the titled compound.

yield: 94% m.p.: oil phase $^1$H NMR(CDCl$_3$) δ: 2.46(3H,s), 2.93(4H,t), 3.07(3H,s), 3.30(4H,t), 3.73(6H,s), 3.99(3H,s), 5.25(1H,d), 5.48(1H,d), 6.01(3H,m). 6.78(1H,s), 7.43(1H,s)

EXAMPLE 159

1-[N-(2-Methoxy-6-methyl-5-vinylpyridin-3-yl)-N-methylaminocarbonyl]-4-(3,5-dimethylphenyl)piperazine 1-[(2-Methoxy-6-methyl-5-vinylpyridin-3-yl)aminocarbonyl]-4-(3,5-dimethylphenyl)piperazine was reacted by the same way with the example 132 to obtain the titled compound.

yield: 89% m.p.: oil phase $^1$H NMR(CDCl$_3$) δ: 2.24(6H,s), 2.43(3H,s), 2.90(4H,t), 3.04(3H,s), 3.27(4H,t), 3.99(3H,s), 5.23(1H,d), 5.45(1H,d), 6.05(3H,m), 6.77(1H,s), 7.40(1H,s)

EXAMPLE 160

1-[N-Ethyl-N-(2-methoxy-6-methyl-5-vinylpyridin-3-yl)aminocarbonyl]-4-(3,5-dimethoxyphenyl)piperazine 1-[(2-Methoxy-6-methyl-5-vinylpyridin-3-yl)aminocarbonyl]-4-(3,5-dimethoxyphenyl)piperazine was reacted by the same way with the example 133 to obtain the titled compound.

yield: 92% m.p.: oil phase $^1$H NMR(CDCl$_3$) δ: 1.09(3H,t), 2.43(3H,s), 2.94(4H,t), 3.28(4H,t), 3.77(6H,s), 4.01(3H,s), 4.11(2H,q), 5.25(1H,d), 5.49(1H,d), 5.98(3H,m), 6.77(1H,s), 7.44(1H,s)

EXAMPLE 161

1-[N-(5-Isopropenyl-2-methoxy-6-methylpyridin-3-yl)-N-methylaminocarbonyl]-4-(3,5-dimethoxyphenyl)piperazine 1-[(5-Isopropenyl-2-methoxy-6-methylpyridin-3-yl)aminocarbonyl]-4-(3,5-dimethoxyphenyl)piperazine was reacted by the same way with the example 132 to obtain the titled compound.

yield: 92% m.p.: oil phase $^1$H NMR(CDCl$_3$) δ: 1.98(3H,s), 2.43(3H,s), 2.92(4H,t), 3.06(3H,s), 3.29(4H,t), 3.74(6H,s), 3.99(3H,s), 4.84(1H,s), 5.30(1H,s), 6.01(3H,m), 7.10(1H,s)

EXAMPLE 162

1-[N-(5-Isopropenyl-2-methoxy-6-methylpyridin-3-yl)-N-methylaminocarbonyl]-4-(3,5-dimethylphenyl)piperazine 1-[(5-Isoprophenyl-2-methoxy-6-methylpyridin-3-yl)aminocarbonyl]-4-(3,5-dimethylphenyl)piperazine was reacted by the same way with the example 132 to obtain the titled compound.

yield: 91% m.p.: oil phase $^1$H NMR(CDCl$_3$) δ: 1.98(3H,s), 2.24(6H,s), 2.43(3H,s), 2.90(4H,t), 3.06(3H,s), 3.28(4H,t), 4.00(3H,s), 4.84(1H,s), 5.19(1H,s), 6.46(3H,m), 7.10(1H,s)

EXAMPLE 163

Ethyl 2-({[4-(3,5-dimethoxyphenyl)piperazino]carbonyl}(5-acetyl-2-methoxy-6-methylpyridin-3-yl)amino)acetate 1-[(5-Acetyl-2-methoxy-6-methylpyridin-3-yl)aminocarbonyl]-4-(3,5-dimethoxylphenyl)piperazine(200 mg, 0.5 mmol) was dissolved in dimethylformamide(15 ml) and thereto sodium hydride(18.5 mg, 0.5 mmol) was added, then followed by stirring at room temperature for 15 min, and ethylbromoacetate(83.5 mg, 0.5 mmol) was added. The resulting mixture was stirred at room temperature for 3 hrs, concentrated under the reduced pressure to remove the used solvent, and purified by column chromatography (ethylacetate:hexane=1:2) to obtain the titled compound.

yield: 84% m.p.: oil phase $^1$H NMR(CDCl$_3$) δ: 1.26(3H,t), 2.51(3H,s), 2.69(3H,s), 3.04(4H,t), 3.43(4H,t), 3.75(6H,s), 4.05(3H,s), 4.15(2H,q), 4.19(2H,s), 6.08(3H,s), 7.96(1H,s)

EXAMPLE 164

Ethyl 2-({[4-(3,5-dimethylphenyl)piperazino]carbonyl}(5-acetyl-2-methoxy-6-methylpyridin-3-yl)amino)acetate 1-[(5-Acetyl-2-methoxy-6-methylpyridin-3-yl)aminocarbonyl]-4-(3,5-dimethylphenyl)piperazine was reacted by the same way with the example 163 to obtain the titled compound.

yield: 80% m.p.: oil phase $^1$H NMR(CDCl$_3$) δ: 1.25(3H,t), 2.56(3H,s), 2.69(3H,s), 3.00(4H,t), 3.29(4H,t), 3.78(6H,s), 4.06(3H,s), 4.18(2H,s), 5.99(3H,m), 7.98(1H,s)

EXAMPLE 165

2-({[4-(3,5-Dimethoxyphenyl)piperazino]carbonyl}(5-acetyl-2-methoxy-6-methylpyridin-3-yl)amino)acetic acid Ethyl ({[4-(3,5-dimethoxyphenyl)piperazino]carbonyl}(5-acetyl-2-methoxy-6-methyllpyridin-3-yl)amino)acetate (200 mg, 0.38 mmol) was dissolved in mixed solvent of dioxane:distilled water=4:1(15 ml), and lithium hydroxide hydrate(48.1 mg, 1.14 mmol) was added, then followed by stirring at room temperature for 3 hrs. The resulting mixture was made acidic with 1N-HCl, extracted with ethylacetate, filtered to dryness, concentrated under the reduced pressure and purified by column chromatography (ethylacetate:hexane=1:2) to obtain the titled compound.

yield: 94%

135–137° C.

$^1$H NMR(CDCl$_3$) δ: 2.52(3H,s), 2.69(3H,s), 3.11(4H,t), 3.49(4H,t), 3.74(6H,s), 4.05(3H,s), 4.24(2H,s), 6.15(3H,m), 7.83(1H,s)

EXAMPLE 166

Ethyl 2-({[4-(3,5-dimethoxyphenyl)piperazino] carbonyl}[5-(1-hyvdroxyethyl)-2-methoxy-6-methylpyridin-3-yl]amino)acetate Ethyl 2-({[4-(3,5-dimethoxyphenyl)piperazino]carbonyl} (5-acetyl-2-methoxy-6-methylpyridin-3-yl)amino)acetate was reacted by the same way with the example 152 to obtain the titled compound.

yield: 97% m.p.: 125–127° C.

$^1$H NMR(CDCl$_3$) δ: 1.26(3H,t), 1.42(3H,d), 2.44(3H,s), 3.04(4H,t), 3.31(4H,t), 3.75(6H,s), 3.97(3H,s), 4.16(2H,q), 4.19(2H,s), 6.15(3H,m), 7.69(1H,s)

EXAMPLE 167

Ethyl 2-({[4-(3,5-dimethoxyphenyl)piperazino] carbonyl}[5-(1hydroxyethyl)-2-methoxy-6-methylpyridin-3-yl]amino)acetate Ethyl 2-({[4-(3,5-dimethoxyphenyl)piperazino]carbonyl} [5-(1-hydroxyethyl)-2-methoxy-6-methylpyridin-3-yl] amino)acetate was reacted by the same way with the example 164 to obtain the titled compound.

yield: 92% m.p.: oil phase $^1$H NMR(CDCl$_3$) δ: 1.41(3H,d), 2.44(3H,s), 2.98(4H,t), 3.36(4H,t), 3.74(6H,s), 3.98(3H,s), 4.40(2H,s), 5.00(1H,q), 6.08(3H,m), 7.69(1H,s)

EXAMPLE 168

Ethyl 2-({[4-(3,5-dimethylphenyl)piperazino] carbonyl}[5-(1-hydroxyethyl)-2-methoxy-6-methylpyridin-3-yl]amino)acetate Ethyl 2-({[4-(3,5-dimethylphenyl)piperazino]carbonyl} (5-acetyl-2-methoxy-6-methylpyridin-3-yl)amino)acetate was reacted by the same way with the example 152 to obtain the titled compound.

yield: 94% m.p. 68–70° C.

$^1$H NMR(CDCl$_3$) δ: 1.13(3H,t), 1.47(3H,d), 2.33(6H,s), 2.44(3H,s), 2.95(4H,t), 3.30(4H,t), 3.98(3H,s), 4.10(2H,q), 5.01(1H,q), 6.46(3H,m), 7.71(1H,s)

EXAMPLE 169

2-({[4-(3,5-Dimethylphenyl)piperazino]carbonyl}[5-(1-hydroxyethyl)-2-methyloxy-6-methylpyridin-3-yl]amino)acetic acid Ethyl 2-({[4-(3,5-dimethylphenyl)piperazino]carbonyl} [5-(1-hydroxyethyl)-2-methoxy-6-methylpyridin-3-yl] amino)acetate was reacted by the same way with the example 165 to obtain the titled compound.

yield: 92% m.p.: 114–116° C.

$^1$H NMR(CDCl$_3$) δ: 1.40(3H,d), 2.23(6H,s), 2.40(3H,s), 2.91(4H,t), 3.21(4H,t), 3.98(3H,s), 4.06(2H,s), 4.90(1H,q), 6.50(3H,m). 6.51(1H,s)

EXAMPLE 170

1-[(4,5-Dimethyl-2-methoxyphenyl)aminocarbonyl]-4-phenylpiperzine a) 3,4-Dimethyl anisole To 3,4-dimethylphenol(19.3 g, 0.16 mol), methanol(150 ml) and KOH(9.65 g, 0.25 mol) were added and then refluxed for 2 hrs. Methyl iodide(36.5 g, 0.25 mol) was added thereto, refluxed for 3 hours and then followed by addition of water(150 ml). The resulting mixture was extracted with ethylacetate and purified by column chromatography to obtain the titled compound.

yield: 81%

$^1$H NMR(500 MHz, CDCl$_3$): δ 2.20(3H,s), 2.24(3H,s), 3.77(3H,s), 6.71(2H,m), 6.97(1H,s)

b) 4,5-Dimethyl-2-nitroanisole

Trifluoroacetic acid(250 ml) was added into 3,4-dimethylanisole(17.1 g, 0.13 mol), successively sodium nitrite(16.6 g, 0.24 mol) was added slowly in water bath, and stirred at room temperature for 14 hrs. After trifluoroacetic acid was removed and water was added thereto, the resulting mixture was extracted with ether, and purified by column chromatography to obtain the titled compound.

yield: 55%

$^1$H NMR(500 MHz, CDCl$_3$): δ 2.25(3H,s), 2.32(3H,s), 3.94(3H,s), 6.85(1H,s), 7.70(1H,s)

c) 4,5-Dimethyl-2-methoxyaniline

Tetrahydrofuran(100 ml) and ethanol(40 ml) were added into 4,5-dimethyl-2-nitroanisole(7.80 g, 0.043 mol) and then added 10% Pd/activated carbon(0.57 g) slowly, hydrogenated for 5 hrs. The reaction was completed by the same way with the above and the resulting product was purified by column chromatography to obtain the titled compound.

yield: 82%

$^1$H NMR(500 MHz, CDCl$_3$): δ 2.23(3H,s), 2.27(3H,s), 3.90(3H,s), 6.80(1H,s), 7.68(1H,s)

d) Phenyl N-(4,5-dimethyl-2-methoxyphenyl) carbamate

To 4,5-dimethyl-2-methoxyaniline(4.50 g, 0.03 mol), methylene chloride(100 ml) was added and phenyl chloroformate(4.80 g, 0.03 mol) was added slowly. The resulting solution was stirred for 2 hrs and thereto water(150 ml) was added, and extracted with methylene chloride and purified by column chromatography to obtain the titled compound.

yield: 98%

$^1$H NMR(500 MHz, CDCl$_3$): δ 2.24(3H,s), 2.27(3H,s), 3.89(3H,s), 6.85(1H,s), 7.20(5H,m), 7.90(1H,s)

e) 1-[(4,5-Dimethyl-2-methoxyphenyl) aminocarbonyl]-4-phenylpiperazine

Phenyl N-(4,5-dimethyl-2-methoxyphenyl)carbamate (5.422 g, 0.02 mol) and 1-phenylpiperazine(3.44 g, 0.02 mol) were dissolved in tetrahydrofuran(10 ml). After DBU (3.04 g, 0.02 mol) was added, the resulting solution was stirred at room temperature for 2 hrs, concentrated and purified by column chromatography to obtain the titled compound.

yield: 85% m.p.: 143–144° C.

$^1$H NMR(500 MHz, CDCl$_3$): δ 2.20(3H,s), 2.21(3H,s), 3.25(4H,t), 3.67(4H,t), 3.85(3H,s), 6.64(1H,s), 6.94(3H,m), 6.99(1H,s), 7.29(1H,t), 7.91(1H,s)

EXAMPLE 171

1-[(4,5-Dimethyl-2-methoxyphenyl)aminocarbonyl]-4-(3,5-dimethoxyphenyl)piperazine Phenyl N-(4,5-dimethyl-2-methoxyphenyl)carbamate and 1-(3,5-dimethoxyphenyl)piperazine were reacted by the same way with the example 170 to obtain the titled compound.

yield: 85% m.p.: 119–120° C.

$^1$H NMR(500 MHz, CDCl$_3$): δ 2.20(3H,s), 2.21(3H,s), 3.27(4H,t), 3.70(4H,t), 3.79(6H,s), 3.85(3H,s), 6.17(2H,m), 6.65(1H,s), 6.98(1H,s), 7.90(1H,s)

Mass(EI) m/z: Calcd for C$_{22}$H$_{29}$N$_3$O$_4$ 399.2158, found 399.2168

EXAMPLE 172

1-[(4,5-Dimethyl-2-methoxyphenyl)aminocarbonyl]-4-(3,5-dimethylphenyl)piperazine Phenyl N-(4,5-dimethyl-2-methoxyphenyl)carbamate and 1-(3,5-dimethylphenyl)piperazine were reacted by the same way with the example 170 to obtain the titled compound.

yield: 88% m.p.: 177–178° C.

$^1$H NMR(500 MHz, CDCl$_3$): δ 2.20(3H,s), 2.21(3H,s), 2.29(6H,s), 3.23(4H,t), 3.66(4H,t), 3.85(3H,s), 6.58(2H,m), 6.65(1H,s), 6.99(1H,s), 7.92(1H,s)

Mass(EI) m/z: Calcd for C$_{22}$H$_{29}$N$_3$O$_2$ 367.2259, found 367.2290

EXAMPLE 173

1-[4,5-Dimethyl-2-methoxyphenyl)aminocarbonyl]-4-(2,3-dimethylphenyl)piperazine

Phenyl N-(4,5-dimethyl-2-methoxyphenyl)carbamate and 1-(2,3-dimethylphenyl)piperazine were reacted by the same way with the example 170 to obtain the titled compound.

yield: 95% m.p.: 140–142° C.

$^1$H NMR(500 MHz, CDCl$_3$): δ 2.21(3H,s), 2.22(3H,s), 2.27(3H,s), 2.29(3H,s), 2.95(4H,t), 3.67(4H,t), 3.85(3H,s), 6.65(1H,s), 7.01(3H,m), 7.93(1H,s)

EXAMPLE 174

1-[(4,5-Dimethyl-2-methoxyphenyl)aminocarbonyl]-4-(2,3,5,6-tetramethylphenyl)piperazine Phenyl N-(4,5-dimethyl-2-methoxyphenyl)carbamate and 1-(2,3,5,6-tetramethylphenyl)piperazine were reacted by the same way with the example 170 to obtain the titled compound.

yield: 93% m.p.: oil phase $^1$H NMR(500 MHz, CDCl$_3$): δ 2.20(9H,s), 2.21(9H,s), 3.17(4H,t), 3.63(4H,t), 3.84(3H,s), 6.64(1H,s), 6.84(1H,s), 7.95(1H,s)

EXAMPLE 175

1-[(4,5-Dimethyl-2-methoxyphenyl)aminocarbonyl]-4-(3,5-difluorophenyl)piperazine Phenyl N-(4,5-dimethyl-2-methoxyphenyl)carbamate and 1-(3,5-difluorophenyl)piperazine were reacted by the same way with the example 170 to obtain the titled compound.

yield: 89% m.p.: 102–103° C.

$^1$H NMR(50 MHz, CDCl$_3$): δ 2.20(3H,s), 2.22(3H,s), 3.29(4H,t), 3.68(4H,t), 3.85(3H,s), 6.65(1H,s), 6.97(3H,m), 7.89(1H,s)

EXAMPLE 176

1-[(4,5-Dimethyl-2-methoxyphenyl)aminocarbonyl]-4-(2-chlorophenyl)piperazine

Phenyl N-(4,5-dimethyl-2-methoxyphenyl)carbamate and 1-(2-chlorophenyl)piperazine were reacted by the same way with the example 170 to obtain the titled compound.

yield: 90% m.p.: 176–177° C.

$^1$H NMR(500 MHz, CDCl$_3$): δ 2.21(3H,s), 2.22(3H,s), 3.10(4H,t,J=5.0 Hz), 3.69(4H,t,J=5.0 Hz), 3.85(3H,s), 6.65(1H,s), 7.02(2H,m), 7.24(1H,m), 7.39(1H,d,J=4.0 Hz), 7.92(1H,s)

EXAMPLE 177

1-[(4,5-Dimethyl-2-methoxyphenyl)aminocarbonyl]-4-(3-chlorophenyl)piperazine

Phenyl N-(4,5-dimethyl-2-methoxyphenyl)carbamate and 1-(3-chlorophenyl)piperazine were reacted by the same way with the example 170 to obtain the titled compound.

yield: 84% m.p.: 75–76° C.

$^1$H NMR(500 MHz, CDCl$_3$): δ 2.20(3H,s), 2.22(3H,s), 3.27(4H,t,J=5.0 Hz), 3.68(4H,t,J=5.0 Hz), 3.85(3H,s), 6.65(1H,s), 6.90(3H,m), 7.21(1H,t), 7.90(1H,s)

Mass(EI) m/z: Calcd for C$_{20}$H$_{24}$N$_3$O$_2$Cl$_1$ 373.1557, found 373.1590

EXAMPLE 178

1-[(4,5-Dimethyl-2-methoxyphenyl)aminocarbonyl]-4-(2-hydroxyphenyl)piperazine

Phenyl N-(4,5-dimethyl-2-methoxyphenyl)carbamate and 1-(2-hydroxyphenyl)piperazine were reacted by the same way with the example 170 to obtain the titled compound.

yield: 87% mp.: 197–199° C.

$^1$H NMR(500 MHz, CDCl$_3$): δ 2.20(3H,s), 2.21(3H,s), 2.98(4H,t), 3.72(4H,t) 3.84(3H,s), 6.65(1H,s), 6.89(1H,t), 7.00(2H,m), 7.13(2H,m), 7.89(1H,s)

EXAMPLE 179

1-[(4,5-Dimethyl-2-methoxyphenyl)aminocarbonyl]-4-(3-hydroxylphenyl)piperazine

Phenyl N-(4,5-dimethyl-2-methoxyphenyl)carbamate and 1-(3-hydroxyphenyl) were reacted by the same way with the example 170 to obtain the titled compound.

yield: 88% m.p.: 177–178° C.

$^1$H NMR(50 MHz, CDCl$_3$): δ 2.19(3H,s), 2.21(3H,s), 3.24(4H,t), 3.68(4H,t), 3.85(3H,s), 6.41(3H,m), 6.65(1H,s), 6.98(1H,s), 7.13(1H,t), 7.88(1H,s)

EXAMPLE 180

1-[(4,5-Dimethyl-2-methoxyphenyl)aminocarbonyl]-4-(3-thiophenyl)piperazine

Phenyl N-(4,5-dimethyl-2-methoxyphenyl)carbamate and 1-(3-thiophenyl)piperazine were reacted by the same way with the example 170 to obtain the titled compound.

yield: 79% m.p.: 108–110° C.

$^1$H NMR(500 MHz, CDCl$_3$): δ 2.20(3H,s), 2.21(3H,s), 3.26(4H,t), 3.65(4H,t), 3.84(3H,s), 6.64(1H,s), 6.97(4H,m), 7.05(1H,s), 7.89(1H,s)

EXAMPLE 181

1-[(4,5-Dimethyl-2-methoxyphenyl)aminocarbonyl]-4-(2-acetoxyphenyl)piperazine

Phenyl N-(4,5-dimethyl-2-methoxyphenyl)carbamate and 1-(2-acetoxyphenyl)piperazine were reacted by the same way with the example 170 to obtain the titled compound.

yield: 84% m.p.: 129–131° C.

$^1$H NMR(500 MHz, CDCl$_3$): δ 2.20(3H,s), 2.21(3H,s), 2.32(3H,s), 3.05(4H,t), 3.63(4H,t), 3.85(3H,s), 6.64(1H,s), 6.99(1H,s), 7.04(1H,m), 7.17(2H,m), 7.22(1H,m), 7.90(1H,s)

EXAMPLE 182

1-[(4,5-Dimethyl-2-methoxyphenyl)aminocarbonyl]-4-(3-acetoxyphenyl)piperazine

Phenyl N-(4,5-dimethyl-2-methoxyphenyl)carbamate and 1-(3-acetoxyphenyl)piperazine were reacted by the same way with the example 170 to obtain the titled compound.

yield: 87% m.p.: 154–156° C.

$^1$H NMR(500 MHz, CDCl$_3$): δ 2.20(3H,s), 2.21(3H,s), 2.29(3H,s), 3.27(4H,t), 3.68(4H,t), 3.85(3H,s), 6.64(1H,s), 6.66(2H,m), 6.82(1H,m), 6.98(1H,s), 7.90(1H,s)

EXAMPLE 183

1-[(4,5-Dimethyl-2-methoxyphenyl)aminocarbonyl]-4-(2-methoxyphenyl)piperazine

Phenyl N-(4,5-dimethyl-2-methoxyphenyl)carbamate and 1-(2-methoxyphenyl)piperazine were reacted by the same way with the example 170 to obtain the titled compound.

yield: 90% m.p.: 144–145° C.

$^1$H NMR(500 MHz, CDCl$_3$): δ 2.20(3H,s), 2.22(3H,s), 2.26(3H,s), 2.95(4H,t, J=5.0 Hz), 3.65(4H,t,J=5.0 Hz), 3.78(3H,s), 3.85(3H,s), 6.59(1H,s), 6.65(1H,s), 7.00(1H,s), 7.11(1H,s), 7.93(1H,s)

EXAMPLE 184

1-[(4,5-Dimethyl-2-methoxyphenyl)aminocarbonyl]-4-(5-methoxy-2-methylphenyl)piperazine Phenyl N-(4,5-dimethyl-2-methoxyphenyl)carbamate and 1-(5-methoxy-2-methylphenyl)piperazine were reacted by the same way with the example 170 to obtain the titled compound.

yield: 88% m.p.: 140–141° C.

$^1$H NMR(500 MHz, CDCl$_3$): δ 2.20(3H,s), 2.22(3H,s), 2.26(3H,s), 2.95(4H,t, J=5.0 Hz), 3.65(4H,t,J=5.0 Hz), 3.78(3H,s), 3.85(3H,s), 6.59(1H,s), 6.65(1H,s), 7.00(1H,s), 7.11(1H,s), 7.93(1H,s)

EXAMPLE 185

1-[(4,5-Dimethyl-2-methoxyphenyl)aminocarbonyl]-4-(2-methoxy-5-methylphenyl)piperazine Phenyl N-(4,5-dimethyl-2-methoxyphenyl)carbamate and 1-(2-methoxy-5-methylphenyl)piperazine were reacted by the same way with the example 170 to obtain the titled compound.

yield: 80% m.p.: 107–108° C.

$^1$H NMR(500 MHz, CDCl$_3$): δ 2.20(3H,s), 2.21(3H,s), 2.29(3H,s), 3.10(4H,t, J=5.0 Hz), 3.69(4H,t,J=5.0 Hz), 3.85(3H,s), 3.86(3H,s), 6.55(1H,s), 6.79(2H,m), 7.01(1H,s), 9.94(1H,s)

EXAMPLE 186

1-[(4,5-Dimethyl-2-methoxyphenyl)aminocarbonyl]-4-(2-methoxy-5-phenylphenyl)piperazine Phenyl N-(4,5-dimethyl-2-methoxyphenyl)carbamate and 1-(2-methoxy-5-phenylphenyl)piperazine were reacted by the same way with the example 170 to obtain the titled compound.

yield: 91% m.p.: 139–140° C.

$^1$H NMR(500 MHz, CDCl$_3$): δ 2.21(3H,s), 2.22(3H,s), 3.20(4H,t), 3.74(4H,t), 3.85(3H,s), 3.94(3H,s), 6.65(1H,s), 7.02(2H,m), 7.32(2H,m), 7.42(2H,t), 7.55(2H,d), 7.93(1H,s)

EXAMPLE 187

1-[(4,5-Dimethyl-2-methoxyphenyl)aminocarbonyl]-4-(2-isopropenylphenyl)piperazine Phenyl N-(4,5-dimethyl-2-methoxyphenyl)carbamate and 1-(2-isopropenylphenyl)piperazine were reacted by the same way with the example 170 to obtain the titled compound.

yield: 80% m.p.: 134–135° C.

$^1$H NMR(500 MHz, CDCl$_3$): δ 2.20(3H,s), 2.21(6H,s), 3.10(4H,t), 3.64(4H,t), 3.85(3H,s), 5.08(1H,s), 5.14(1H,s), 6.64(1H,s), 7.05(3H,m), 7.70(1H,m), 7.92(1H,s)

EXAMPLE 188

1-[(4,5-Dimethyl-2-methoxyphenyl)aminocarbonyl]-4-(1-naphthyl)piperazine

Phenyl N-(4,5-dimethyl-2-methoxyphenyl)carbamate and 1-(1-naphthyl)piperazine were reacted by the same way with the example 170 to obtain the titled compound.

yield: 92% m.p.: 160–162° C.

$^1$H NMR(500 MHz, CDCl$_3$): δ 2.20(3H,s), 2.24(3H,s), 3.31(4H,t,J=5.0 Hz), 3.83(3H,s), 4.04(4H,t), 6.39(2H,m), 6.69(1H,s), 7.13(1H,t), 7.30(1H,s), 7.46(1H,s)

EXAMPLE 189

1-[(4,5-Dimethyl-2-methoxyphenyl)aminocarbonyl]-4-(1-anthranyl)piperazine

Phenyl N-(4,5-dimethyl-2-methoxyphenyl)carbamate and 1-(1-anthranyl)piperazine were reacted by the same way with the example 170 to obtain the titled compound.

yield: 94% m.p.: 74–75° C.

$^1$H NMR(500 MHz, CDCl$_3$): δ 2.20(3H,s), 2.22(3H,s), 3.24(4H,t), 3.70(4H,t), 3.86(3H,s), 6.70(1H,s), 7.05(3H,m), 7.45(5H,m), 8.00(2H,m)

EXAMPLE 190

1-[N-(4,5-Dimethyl-2-methoxyphenyl)-N-methylaminocarbonyl]-4-(3,5-dimethoxyphenyl)piperazine 1-[(4,5-dimethyl-2-methoxyphenyl)aminocarbonyl]-4-(3,5-dimethoxyphenyl)piperazine(0.2 g, 0.5 mmole) was dissolved in dimethylformamide(15 ml), sodium hydride(12 mg, 0.5 mmole) was added thereto slowly, and then the resulting mixture was stirred at room temperature for 15 min, then followed by addition of iodomethane(71 mg, 0.5 mmole) and subsequently at room temperature for 16 hours. The resulting mixture was concentrated under the reduced pressure to remove the used solvent, extracted with methylene chloride, dried, filtered and purified by column chromatography to obtain the titled compound.

yield: 92% m.p: 86–88° C.

$^1$H NMR(500 MHz, CDCl$_3$): δ 2.21(3H,s), 2.24(3H,s), 2.92(4H,t), 3.06(3H,s), 3.31(4H,t), 3.75(6H,s), 3.83(3H,s), 6.00(3H,m), 6.71(1H,s), 6.83(1H,s)

Mass(EI) m/z: Calcd for C$_{23}$H$_{31}$N$_3$O$_4$ 413.2314, found 413.2293

EXAMPLE 191

1-[N-(4,5-Dimethyl-2-methoxyphenyl)-N-methylaminocarbonyl]-4-(3,5-dimethylphenyl)piperazine 1-[(4,5-Dimethyl-2-methoxyphenyl)aminocarbonyl]-4-(3,5-dimethylphenyl)piperazine was reacted by the same way with the example 190 to obtain the titled compound.

yield: 90% m.p.: 137–138° C.

$^1$H NMR(500 MHz, CDCl$_3$): δ 2.15(3H,s), 2.24(9H,s), 2.88(4H,t), 3.06(3H,s), 3.29(4H,t), 3.83(3H,s), 6.45(3H,m), 6.71(1H,s), 6.83(1H,s)

Mass(EI) m/z: Calcd for C$_{23}$H$_{29}$N$_3$O$_2$ 381.2416, 381.2436

EXAMPLE 192

1-[N-(4,5-Dimethyl-2-methoxyphenyl)-N-methylaminocarbonyl]-4-(3,5-difluorophenyl)piperazine 1-[(4,5-Dimethyl-2-methoxyphenyl)aminocarbonyl]-4-(3,5-difluorophenyl)piperazine was reacted by the same way with the example 190 to obtain the titled compound.

yield: 87% m.p.: 98–100° C.

$^1$H NMR(500 MHz, CDCl$_3$): δ 2.16(3H,s), 2.25(3H,s), 2.92(4H,t), 3.06(3H,s), 3.29(4H,t), 3.83(3H,s), 6.23(3H,m), 6.72(1H,s), 6.83(1H,s)

EXAMPLE 193

1-[N-Ethyl-N-(4,5-dimethyl-2-methoxyphenyl)aminocarbonyl]-4-(3,5-dimethoxyphenyl)piperazine 1-[(4,5-Dimethyl-2-methoxyphenyl)aminocarbonyl]-4-(3,5-dimethoxyphenyl)piperazine(0.2 g, 0.5 mmole) was dissolved in dimethylformamide(15 ml), and thereto sodium hydride(12 mg, 0.5 mmole) was added slowly. The resulting mixture was stirred at room temperature for 15 min. After iodoethane(78 mg, 0.5 mmol) was added, the resulting mixture was stirred at room temperature for 16 hours. The resulting mixture was concentrated under the reduced pressure to remove the used solvent, extracted with methylene chloride, dried, filtered and purified by column chromatography to obtain the titled compound.

yield: 89% m.p.: oil phase $^1$H NMR(500 MHz, CDCl$_3$): δ 1.09(3H,t), 2.16(3H,s), 2.24(3H,s), 2.75(4H,t), 3.28(4H,t), 3.52(2H,q), 3.75(6H,s), 3.81(3H,s), 5.98(3H,m), 6.70(1H,s), 6.80(1H,s)

EXAMPLE 194

1-[N-(4,5-Dimethyl-2-methoxyphenyl)-N-ethylaminocarbonyl]-4-(3,5-dimethylphenyl)piperazine 1-[(4,5-Dimethyl-2-methoxyphenyl)aminocarbonyl]-4-(3,5-dimethylphenyl)piperazine was reacted by the same way with the example 193 to obtain the titled compound.

yield: 93% m.p.: 80–82° C.

$^1$H NMR(500 MHz, CDCl$_3$): δ 1.21(3H,t), 2.15(3H,s), 2.23(9H,s), 2.90(4H,t), 3.25(4H,t), 3.59(2H,q), 3.81(3H,s), 6.45(3H,m), 6.69(1H,s), 6.81(1H,s)

EXAMPLE 195

1-[N-(4,5-Dimethyl-2-methoxyphenyl)-N-ethylaminocarbonyl]-4-(3,5-difluorophenyl)piperazine 1-[(4,5-Dimethyl-2-methoxyphenyl)aminocarbonyl]-4-(3,5-difluorophenyl)piperazine was reacted by the same way with the example 193 to obtain the titled compound.

yield: 87% m.p.: oil phase $^1$H NMR(500 MHz, CDCl$_3$): δ 1.09(3H,t), 2.16(3H,s), 2.25(3H,s), 2.90(4H,t), 3.27(4H,t), 3.52(2H,q), 3.81(3H,s), 6.24(3H,m), 6.70(1H,s), 6.81(1H,s)

EXAMPLE 196

1-[N-Isopropyl-N-(4,5-dimethyl-2-methoxyphenyl)aminocarbonyl]-4-(3,5-difluorophenyl)piperazine 1-[(4,5-Dimethyl-2-methoxyphenyl)aminocarbonyl]-4-(3,5-difluorophenyl)piperazine(0.2 g, 0.52 mmole) was dissolved in dimethylformamide(15 ml) and thereto sodium hydride(12.48 mg, 0.52 mmole) was slowly added. The resulting mixture was stirred at room temperature for 15 min. After 2-iodopropane(87.88 mg, 0.52 mmole) was added thereto, the resulting mixture was stirred at room temperature for 16 hours. The resulting mixture was concentrated under the reduced pressure to remove the used solvent, extracted with methylene chloride, dryed, filtered and purified by column chromatography to obtain the titled compound.

yield: 84% m.p.: oil phase $^1$H NMR(500 MHz, CDCl$_3$): δ 1.10(3H,s), 1.26(3H,s), 2.20(3H,s), 2.25(3H,s), 2.86(4H,t), 3.26(4H,t), 3.77(3H,s), 4.25(1H,m), 6.17(3H,m), 6.68(1H,s), 6.82(1H,s)

EXAMPLE 197

1-[(4,5-Dimethyl-2-methoxyphenyl)aminothiocarbonyl]-4-(3,5-dimethoxyphenyl)piperazine (a) Phenyl N-(4,5-dimethyl-2-methoxyphenyl)thiocarbamate To 3,4-dimethyl-2-methoxyaniline(4.50 g, 0.03 mol), methylene chloride(100 ml) was added and then phenyl chlorothionoformate(5.16 g, 0.03 mol) was added slowly. The resulting mixture was stirred for 2 hours, and thereto water(150 ml) was added. The resulting mixture was extracted with methylene chloride and purified by column chromatography to obtain the titled compound.

yield: 92%
$^1$H NMR(500 MHz, CDCl$_3$): δ 2.21(3H,s), 2.25(3H,s), 3.85(3H,s), 6.80(1H,s), 6.93(5H,m), 7.31(1H,s)

(b) 1-[(4,5-Dimethyl-2-methoxyphenyl)aminothiocarbonyl]-4-(3,5-dimethoxyphenyl)piperazine Phenyl N-(4,5-dimethyl-2-methoxyphenyl)thiocarbamate (0.2 g, 0.7 mmol) and 1-(3,5-dimethoxyphenyl)piperazine (0.16 g, 0.7 mmol) were dissolved in tetrahydrofuran(10 ml) and thereto DBU(0.11 g, 0.7 mmole) was added, followed by stirring at room temperature for 2 hours. The resulting product was concentrated and purified by chromatography to obtain the titled compound.

yield: 84%
m.p.: 128–129° C.
$^1$H NMR(500 MHz, CDCl$_3$): δ 2.20(3H,s), 2.24(3H,s), 2.32(6H,s), 3.37(4H,t), 3.83(3H,s), 4.08(4H,t), 6.69(3H,m), 7.39(1H,m), 7.47(1H,s)

Mass(EI) m/z: Calcd for C$_{22}$H$_{29}$N$_3$O$_3$S$_1$ 415.1929, found 415.1912

EXAMPLE 198

1-[(4,5-Dimethyl-2-methoxyphenyl)aminothiocarbonyl]-4-(3,5-dimethylphenyl)piperazine Phenyl N-(4,5-dimethyl-2-methoxyphenyl)thiocarbamate and 1-(3,5-dimethylphenyl)perazine were reacted by the same way with the example 197 to obtain the titled compound.

yield: 90%
m.p.: 164–165° C.
$^1$H NMR(500 MHz, CDCl$_3$): δ 2.20(3H,s), 2.24(3H,s), 2.32(6H,s), 3.37(4H,t), 3.83(3H,s), 4.08(4H,t), 6.69(3H,m), 7.39(1H,m), 7.47(1H,s)

Mass(EI) m/z: Calcd for C$_{22}$H$_{29}$N$_3$O$_1$S$_1$ 383.2031, found 383.2086

EXAMPLE 199

1-[(4,5-Dimethyl-2-methoxyphenyl)aminothiocarbonyl]-4-(2,3-dimethylphenyl)piperazine Phenyl N-(4,5-dimethyl-2-methoxyphenyl)thiocarbamate and 1-(2,3-dimethylphenyl)piperazine were reacted by the same way with the example 197 to obtain the titled compound.

yield: 89%
m.p.: 151–152° C.
$^1$H NMR(500 MHz, CDCl$_3$): δ 2.21(3H,s), 2.24(3H,s), 2.29(6H,s), 3.03(4H,t), 3.83(3H,s), 4.10(4H,t), 6.69(1H,s), 6.97(2H,m), 7.11(1H,t)

EXAMPLE 200

1-[(4,5-Dimethyl-2-methoxyphenyl)aminothiocarbonyl]-4-(3,5-difluorophenyl)piperazine Phenyl N-(4,5-dimethyl-2-methoxyphenyl)thiocarbamate and 1-(3,5-difluorophenyl)piperazine were reacted by the same way with the example 197 to obtain the titled compound.

yield: 92%
m.p.: 167–168° C.
$^1$H NMR(500 MHz, CDCl$_3$): δ 2.20(3H,s), 2.24(3H,s), 2.27(3H,s), 2.32(3H,s), 3.39(4H,t,J=5.0 Hz), 3.83(3H,s), 4.14(4H,t), 6.70(1H,s), 6.80(2H,m), 7.36(1H,s), 7.44(1H,s)

EXAMPLE 201

1-[(4,5-Dimethyl-2-methoxyphenyl)aminothiocarbonyl]-4-(3,5-dichlorophenyl)piperazine Phenyl N-(4,5-dimethyl-2-methoxyphenyl)thiocarbamate and 1-(3,5-dichlorophenyl)piperazine were reacted by the same way with the example 197 to obtain the titled compound.

yield: 85%
m.p.: 188–189° C.
$^1$H NMR(500 MHz, CDCl$_3$): δ 2.20(3H,s), 2.24(3H,s), 3.35(4H,t,J=5.0 Hz), 3.83(3H,s), 4.04(4H,t,J=5.0 Hz), 6.70(2H,m), 6.83(1H,s), 7.30(1H,s), 7.48(1H,s)

Mass(EI) m/z: Calcd for C$_{20}$H$_{24}$N$_3$O$_2$Cl$_1$ 423.0938, 423.0956

EXAMPLE 202

1-[(4,5-Dimethyl-2-methoxyphenyl)amminothiocarbonyl]-4-(2-fluorophenyl)piperazine Phenyl N-(4,5-dimethyl-2-methoxyphenyl)thiocarbamate and 1-(2-fluorophenyl)piperazine were reacted by the same way with the example 197 to obtain the titled compound.

yield: 87%
m.p.: 139–140° C.
$^1$H NMR(500 MHz, CDCl$_3$): δ 2.21(3H,s), 2.24(3H,s), 3.40(4H,t), 3.83(3H,s), 4.25(4H,t), 6.70(1H,s), 7.13(3H,m), 7.37(2H,m)

EXAMPLE 203

1-[(4,5-Dimethyl-2-methoxyphenyl)aminothiocarbonyl]-4-(2-chlorophenyl)piperazine Phenyl N-(4,5-dimethyl-2-methoxyphenyl)thiocarbamate and 1-(2-chlorophenyl)piperazine were reacted by the same way with the example 197 to obtain the titled compound.

yield: 85%
m.p.: 115–116° C.
$^1$H NMR(500 MHz, CDCl$_3$): δ 2.21(3H,s), 2.24(3H,s), 3.18(4H,t), 3.83(3H,s), 4.09(4H,t), 6.69(1H,s), 7.05(2H,m), 7.33(1H,s), 7.41(2H,m)

EXAMPLE 204

1-[(4,5-Dimethyl-2-methoxyphenyl)
aminothiocarbonyl]-4-(2-methoxyphenyl)piperazine Phenyl N-(4,5-dimethyl-2-methoxyphenyl)thiocarbamate and 1-(2-methoxyphenyl)piperazine were reacted by the same way with the example 197 to obtain the titled compound.

yield: 90%
m.p.: oil phase
$^1$H NMR(500 MHz, CDCl$_3$): δ 2.20(3H,s), 2.23(3H,s), 3.14(4H,t,J=5.0 Hz), 3.82(3H,s), 3.88(3H,s), 4.06(4H,t,J=5.0 Hz), 6.69(1H,s), 6.94(3H,m), 7.30(1H,s), 7.40(1H,s)

EXAMPLE 205

1-[(4,5-Dimethyl-2-methoxyphenyl)
aminothiocarbonyl]-4-( 2-methylthiophenyl)
piperazine Phenyl N-(4,5-dimethyl-2-methoxyphenyl)thiocarbamate and 1-(2-methylthiophenyl)piperazine were reacted by the same way with the example 197 to obtain the titled compound.

yield: 93%
m.p.: 136–137° C.
$^1$H NMR(500 MHz, CDCl$_3$): δ 2.20(3H,s), 2.26(3H,s), 2.45(3H,s), 3.33(4H,t), 3.82(3H,s), 4.39(4H,t), 6.74(1H,s), 7.16(3H,m), 7.47(2H,m)

EXAMPLE 206

1-[(4,5-Dimethyl-2-methoxyphenyl)
aminothiocarbonyl]-4-(3-hydroxyphenyl)piperazine Phenyl N-(4,5-dimethyl-2-methoxyphenyl)thiocarbamate and 1-(3-hydroxyphenyl)piperazine were reacted by the same way with the example 197 to obtain the titled compound.

yield: 77%
m.p.: Decomposed(200° C.)
$^1$H NMR(500 MHz, CDCl$_3$): δ 2.17(3H,s), 2.23(3H,s), 3.31(4H,t), 3.82(3H,s), 4.03(3H,t), 6.37(2H,m), 6.47(1H,d), 6.69(1H,s), 7.13(1H,t), 7.45(1H,s)

EXAMPLE 207

1-[(4,5-Dimethyl-2-methoxyphenyl)
aminothiocarbonyl]-4-(2-phenoxyphenyl)piperazine Phenyl N-(4,5-dimethyl-2-methoxyphenyl)thiocarbamate and 1-(2-phenoxyphenyl)piperazine were reacted by the same way with the example 197 to obtain the titled compound.

yield: 86%
m.p.: oil phase
$^1$H NMR(500 MHz, CDCl$_3$): δ 2.17(3H,s), 2.24(3H,s), 3.19(4H,t), 3.80(3H,s), 3.85(4H,t), 6.66(1H,s), 6.91(2H,m), 6.98(1H,m), 7.05(3H,m), 7.13(1H,m), 7.23(1H,m), 7.31 (2H,m), 7.36(1H,s)

EXAMPLE 208

1-[(4,5-Dimethyl-2-methoxyphenyl)
aminothiocarbonyl]-4-(2-isopropenylphenyl)
piperazine Phenyl N-(4,5-dimethyl-2-methoxyphenyl)thiocarbamate and 1-(2-isopropenylphenyl)piperazine were reacted by the same way with the example 197 to obtain the titled compound.

yield: 75%
m.p.: 157–158° C.
$^1$H NMR(500 MHz, CDCl$_3$): δ 2.20(3H,s), 2.21(3H,s), 2.24(3H,s), 3.19(4H,t), 3.82(3H,s), 4.05(4H,t), 5.07(1H,s), 5.16(1H,s), 6.69(1H,s), 7.11(3H,m), 7.33(1H,s), 7.45(1H,s)

EXAMPLE 209

1-[(4,5-Dimethyl-2-methoxyphenyl)
aminothiocarbonyl]-4-(2-methoxy-5-methylphenyl)
piperazine Phenyl N-(4,5-dimethyl-2-methoxyphenyl)thiocarbamate and 1-(2-methoxy-5-methylphenyl)piperazine were reacted by the same way with the example 197 to obtain the titled compound.

yield: 87%
m.p.: oil phase
$^1$H NMR(500 MHz, CDCl$_3$): δ 2.20(3H,s), 2.23(3H,s), 2.29(3H,s), 3.13(4H,t), 3.83(3H,s), 3.85(3H,s), 4.05(4H,t), 6.69(1H,s), 6.83(2H,m), 7.30(1H,s), 7.40(1H,s)

EXAMPLE 210

1-[(4,5-Dimethyl-2-methoxyphenyl)
aminothiocarbonyl]-4-(1-nalphthyl)piperazine

Phenyl N-(4,5-dimethyl-2-methoxyphenyl)thiocarbamate and 1-(1-naphthyl)piperazine were reacted by the same way with the example 197 to obtain the titled compound.

yield: 87%
m.p.: 139–140° C.
$^1$H NMR(500 MHz, CDCl$_3$): δ 2.23(3H,s), 2.24(3H,s), 3.21(4H,t), 3.84(3H,s), 4.09(4H,t), 6.70(1H,s), 7.10(1H,d), 7.48(5H,m), 7.85(1H,m), 8.22(1H,d)

EXAMPLE 211

1-[(5-Acetyl-2-methoxy-4-methylphenyl)
aminocarbonyl]-4-(3,5-dimethoxyphenyl)piperazine Phenyl N-(5-acetyl-2-methoxy-4-methylphenyl) carbamate and 1-(3,5-dimethoxyphenyl)piperazine were reacted by the same way with the example 170 to obtain the titled compound.

yield: 91%
m.p.: 103–105° C.
$^1$H NMR(500 MHz, CDCl$_3$): δ 2.54(3H,s), 2.59(3H,s), 3.27(4H,t), 3.70(4H,t), 3.79(6H,s), 3.94(3H,s), 6.13(3H,m), 6.70(1H,s), 7.05(1H,s), 8.72(1H,s)

EXAMPLE 212

1-[(5-Acetyl-2-methoxy-4-methylphenyl)
aminocarbonyl]-4-(3,5-dimethylphenyl)piperazine Phenyl N-(5-acetyl-2-methoxy-4-methylphenyl) carbamate and 1-(3,5-dimethylphenyl)piperazine were reacted by the same way with the example 170 to obtain the titled compound.

yield: 88%
m.p.: 140–142° C.
$^1$H NMR(500 MHz, CDCl$_3$): δ 2.30(3H,s), 2.54(3H,s), 2.59(3H,s), 3.26(4H,t), 3.70(4H,t), 3.97(3H,s), 6.61(3H,m), 6.70(1H,s), 7.06(1H,s), 8.72(1H,s)

EXAMPLE 213

1-[(5-Acetyl-2-methoxy-4-methylphenyl)
aminocarbonyl]-4-(3,5-dichlorophenyl)piperazine Phenyl N-(5-acetyl-2-methoxy-4-methylphenyl) carbamate and 1-(3,5-dichlorophenyl)piperazine were reacted by the same way with the example 170 to obtain the titled compound.

yield: 78% m.p.: 170–172° C.

¹H NMR(500 MHz, CDCl₃): δ 2.54(3H,s), 2.59(3H,s), 3.32(4H,t), 3.74(4H,t), 3.94(3H,s), 6.69(1H,s), 6.86(3H,m), 7.04(1H,s), 8.69(1H,s)

EXAMPLE 214

1-{[5-(1-Hydroxyethyl)-2-methoxy-4-methylphenyl]aminocarbonyl}-4-(3,5-dimethoxyphenyl)piperazine 1-[(5-Acetyl-2-methoxy-4-methylphenyl)aminocarbonyl]-4-(3,5-dimethoxyphenyl)piperazine(0.2 g, 0.47 mmol) was dissolved in anhydrous ethanol(15 ml), and sodium borohydride(17 mg) was added thereto, and then the resulting mixture was stirred at room temperature for 2 hours, concentrated under the reduced pressure to remove ethanol, and purified by column chromatography (ethylacetate:hexane=1:2) to obtain the titled compound.

yield: 96% m.p.: 152–154° C.

¹H NMR(500 MHz, CDCl₃): δ 1.41(3H,d), 2.32(3H,s), 3.27(4H,t), 3.71(4H,t), 3.79(6H,s), 3.87(3H,s), 5.04(1H,q), 6.10(3H,m), 6.63(1H,s), 7.01(1H,s), 8.22(1H,s)

EXAMPLE 215

1-{[5-(1-Hydroxyethyl)-2-methoxy-4-methylphenyl]aminocarbonyl}-4-(3,5-dimethylphenyl)piperazine 1-[(5-Acetyl-2-methoxy-4-methylphenyl]aminocarbonyl}-4-(3,5-dimethylphenyl)piperazine was reacted by the same way with the example 214 to obtain the titled compound.

yield: 96% m.p.: 140–142° C.

¹H NMR(500 MHz, CDCl₃): δ 1.48(3H,d), 2.33(3H,s), 3.26(4H,t), 3.68(4H,t), 3.87(3H,s), 5.06(1H,q), 6.61(3H,m), 6.64(1H,s), 7.01(1H,s), 8.22(1H,s)

EXAMPLE 216

1-[(2-Methoxy-4-methyl-5-vinylphenyl)aminocarbonyl]-4-(3,5-dimethoxyphenyl)piperazine 1-{[5-(1-Hydroxyethyl)-2-methoxy-4-methylphenyl]aminocarbonyl}-4-(3,5-dimethoxyphenyl)piperazine(0.2 g, 0.47 mmol) was dissolved in chloroform(15 ml), pyridium p-toluenesulfonate(0.12 g, 0.47 mmol) was added thereto, and the resulting mixture was refluxed for 16 hours, and concentrated under the reduced pressure to remove chloroform and purified by column chromatography (ethylacetate:hexane=1:2) to obtain the titled compound.

yield: 84% m.p.: 163–165° C.

¹H NMR(500 MHz, CDCl₃): δ 2.31(3H,s), 3.23(4H,t), 3.58(4H,t), 3.77(6H,s), 3.87(3H,s), 5.20(1H,d), 5.62(1H,d), 6.59(3H,m), 6.63(1H,s), 6.88(1H,t), 6.99(1H,s), 8.32(1H,s)

EXAMPLE 217

1-[(2-Methoxy-4-methyl-5-vinylphenyl)aminocarbonyl]-4-(3,5-dimethylphenyl)piperazine 1-{[5-(1-Hydroxyethyl)-2-methoxy-4-methylphenyl]aminocarbonyl}-4-(3,5-dimethylphenyl)piperazine was reacted by the same way with the example 216 to obtain the titled compound.

yield: 82% m.p.: 201–203° C.

¹H NMR(500 MHz, CDCl₃): δ 2.29(6H,s), 2.34(3H,s), 3.24(4H,t), 3.68(4H,t), 3.87(3H,s), 5.22(1H,d), 5.66(1H,d), 6.59(3H,m), 6.63(1H,s), 6.86(1H,t), 7.02(1H,s), 8.32(1H,s)

EXAMPLE 218

1-[(5-Acetyl-2-methoxy-4-methylphenyl)aminothiocarbonyl]-4-(3,5-dimethoxyphenyl)piperazine Phenyl N-(5-acetyl-2-methoxy-4-methylphenyl)thiocarbamate and 1-(3,5-dimethoxyphenyl)piperazine were reacted by the same way with the example 197 to obtain the titled compound.

yield: 82% m.p.: 163–165° C.

¹H NMR(500 MHz, CDCl₃): δ 2.16(3H,s), 2.56(3H,s), 3.35(4H,t), 3.91(6H,s), 4.03(3H,s), 4.13(4H,t), 6.06(3H,m), 6.73(1H,s), 8.62(1H,s)

EXAMPLE 219

1-[(5-Acetyl-2-methoxy-4-methylphenyl)aminothiocarbonyl]-4-(3,5-dimethylphenyl)piperazine Phenyl N-(5-acetyl-2-methoxy-4-methylphenyl)thiocarbamate and 1-(3,5-dimethylphenyl)piperazine were reacted by the same way with the example 197 to obtain the titled compound.

yield: 79% m.p.: 180–182° C.

¹H NMR(500 MHz, CDCl₃): δ 2.29(6H,s), 2.57(6H,s), 3.32(4H,t), 3.92(3H,s), 4.12(4H,t), 6.56(3H,m), 6.72(1H,s), 7.39(1H,s), 8.63(1H,s)

EXAMPLE 220

1-[(5-Acetyl-2-methoxy-4-methylphenyl)aminothiocarbonyl]-4-(3,5-dichlorophenyl)piperazine Phenyl N-(5-acetyl-2-methoxy-4-methylphenyl)thiocarbamate and 1-(3,5-dichlorophenyl)piperazine were reacted by the same way with the example 197 to obtain the titled compound.

yield: 79% m.p.: 201–203° C.

¹H NMR(500 MHz, CDCl₃): δ 2.20(3H,s), 2.57(3H,s), 3.46(4H,t), 3.92(3H,s), 4.25(4H,t), 6.64(1H,s), 6.88(3H,m), 7.72(1H,s), 8.57(1H,s)

EXAMPLE 221

1-{[5-(1-Hydroxyethyl)-2-methoxy-4-methylphenyl]aminothiocarbonyl}-4-(3,5-dimethoxyphenyl)piperazine 1-[(5-Acetyl-2-methoxy-4-methylphenyl)aminothiocarbony]-4-(3,5-dimethoxyphenyl)piperazine was reacted by the same way with the example 214 to obtain the titled compound.

yield: 94% m.p.: 146–148° C.

¹H NMR(500 MHz, CDCl₃): δ 1.44(3H,d), 2.32(3H,s), 3.35(4H,t), 3.78(6H,s), 3.84(3H,s), 4.11(4H,t), 5.06(1H,q), 6.13(3H,m), 6.66(1H,s), 7.41(1H,s), 7.77(1H,s)

EXAMPLE 222

1-{[5-(1-Hydroxyethyl)-2-methoxy-4-methylphenyl]aminothiocarbonyl}-4-(3,5-dimethylphenyl)piperazine 1-[(5-Acetyl-2-methoxy-4-methylphenyl)aminothiocarbony]-4-(3,5-dimethylphenyl)piperazine was reacted by the same way with the example 214 to obtain the titled compound.

yield: 93% m.p.: 150–152° C.

¹H NMR(500 MHz, CDCl₃): δ 1.44(3H,d), 2.29(6H,s), 2.32(3H,s), 3.30(4H,t), 3.84(3H,s), 4.07(4H,t), 5.06(1H,q), 6.61(3H,m), 6.66(1H,s), 7.38(1H,s), 7.79(1H,s)

EXAMPLE 223

1-{[5-(1-Hydroxyethyl)-2-methoxy-4-methylphenyl]aminothiocarbonyl}-4-(3,5-dichlorophenyl)piperazine 1-[(5-Acetyl-2-methoxy-4-methylphenyl)aminothiocarbony]-4-(3,5-dichlorophenyl)piperazine was reacted by the same way with the example 214 to obtain the titled compound.

yield: 77% m.p.: 166–168° C.

¹H NMR(500 MHz, CDCl₃): δ 1.45(3H,d), 2.33(3H,s), 3.35(4H,t), 3.84(3H,s), 4.03(4H,t), 5.07(1H,q), 6.68(3H,m), 6.83(1H,s), 7.37(1H,s), 7.82(1H,s)

EXAMPLE 224

Ethyl 2-({[4-(3,5-dimethoxyphenyl)piperazino]carbonyl}-2-methoxy-4,5-dimethylanilino)acetate 1-[(4,5-Dimethyl-2-methoxyphenyl)aminocarbonyl]-4-(3,5-dimethoxyphenyl)piperazine(0.2 g, 0.5 mmol) was dissolved in dimethylformamide(15 ml), sodium hydride(18.5 mg, 0.5 mmol) was added thereto, and the resulting mixture was stirred at room temperature. Then, ethyl bromoacetate (83.5 mg, 0.5 mmol) was added thereto and the resulting mixture was stirred for 3 hours, concentrated under the reduced pressure to remove the used solvent and purified by column chromatography(ethylacetate:hexane=1:2) to obtain the titled compound.

yield: 79% m.p.: oil phase

¹H NMR(500 MHz, CDCl₃): δ 1.36(3H,t), 2.15(3H,s), 2.23(3H,s), 2.91(4H,t), 3.22(4H,t), 3.82(6H,s), 4.12(3H,s), 4. 18(2H,s), 5.98(3H,m), 6.69(1H,s), 7.03(1H,s)

EXAMPLE 225

Ethyl 2-({[4-(3,5-dimethylphenyl)piperazino]carbonyl}-2-methoxy-4,5-dimethylanilino)acetate 1-[(4,5-Dimethyl-2-methoxyphenyl)aminocarbonyl]-4-(3,5-dimethylphenyl)piperazine was reacted by the same way with the example 224 to obtain the titled compound.

yield: 78% m.p.: oil phase

¹H NMR(500 MHz, CDCl₃): δ 1.26(3H,t), 1.56(6H,s), 2.17(3H,s), 2.24(3H,s), 3.32(4H,t), 3.52(4H,t), 3.82(3H,s), 4.15(2H,q), 4.18(2H,s), 6.70(3H,m), 6.94(1H,s), 7.46(1H,s)

EXAMPLE 226

2-({[4-(3,5-Dimethoxyphenyl)piperazino]carbonyl}-2-methoxy-4,5-dimethylanilino)acetic acid Ethyl 2-({[4-(3,5-dimethoxyphenyl)piperazino]carbonyl}-2-methoxy-4,5-dimethylanilino)acetate(200 mg, 0.41 mmole) was dissolved in dioxane:distilled water(4:1, 15 ml), lithium hydroxide monohydrate(50.7 mg, 1.23 mmol) was added thereto, and then the resulting mixture was stirred at room temperature for 3 hours, acidified with 1N-hydrochloric acid, extracted with ethylacetate, filtered to dryness, concentrated under the reduced pressure to remove the used solvent, and purified by column chromatography (ethylacetate:hexane=1:2) to obtain the titled compound.

yield: 80% m.p.: 188–189° C.

¹H NMR(500 MHz, CDCl₃): δ 2.14(3H,s), 2.23(3H,s), 2.93(4H,t), 3.35(4H,t), 3.75(6H,s), 3.87(3H,s), 4.18(2H,s), 5.96(3H,m), 6.71(1H,s), 7.71(1H,s)

EXAMPLE 227

2-({[4-(3,5-Dimethylphenyl)piperazino]carbonyl}-2-methoxy-4,5-dimethylanilino)acetic acid Ethyl 2-({[4-(3,5-dimethylphenyl)piperazino]carbonyl}-2-methoxy-4,5-dimethylanilino)acetate was reacted by the same way with the example 226 to obtain the titled compound.

yield: 78% m.p.: 170–171° C.

¹H NMR(500 MHz CDCl₃): δ 2.13(3H,s), 2.24(9H,s), 2.91(4H,t), 3.35(4H,t), 3.83(3H,s), 4.18(2H,s), 6.45(3H,m), 6.70(2H,s), 6.80(1H,s)

EXAMPLE 228

1-[(2-Hydroxy-4,5-dimethylphenyl)aminocarbonyl]-4-(3,5-dimethoxyphenyl)piperazine (a) 4,5-Dimethyl-2-nitrophenol To 3,4-dimethylphenol(12.1 g, 0.1 mol), trifluoroacetic acid(250 ml) was added, and in water bath sodium nitrite (12.4 g, 0.18 mol) was added slowly. The resulting mixture was stirred at room temperature for 14 hours and concentrated under the reduced pressure to remove trifluoroacetic acid, followed by addition of water(150 ml), extracted with ether and purified by column chromatography to obtain the titled compound.

yield: 80%

¹H NMR(500 MHz, CDCl₃): δ 2.23(3H,s), 2.29(3H,s), 6.93(1H,s), 7.84(1H,s)

(b) 4,5-Dimethyl-2-hydroxyaniline

To 4,5-dimethyl-2-nitrophenol(11.7 g, 0.07 mol), tetrahydrofuran(100 ml) and ethanol(40 ml) were added, and 10% palladium/activated carbon(0.57 g) was added slowly, and then the mixture was hydrogenated for 5 hours. The reaction mixture was concentrated and chromatographed by the same way above to obtain the titled compound.

yield: 77%

¹H NMR(500 MHz, CDCl₃): δ 2.11(6H,s), 6.56(2H,s)

(c) Phenyl N-(4,5-dimethyl-2-hydroxyphenyl) carbamate

To 4,5-dimethyl-2-hydroxyaniline(6.80 g, 0.05 mole), methylene chloride(100 ml) was added and then phenyl chloroformate(8.0 g, 0.05 mole) was added slowly. After stirring for 2 hours, addition of water(150 ml), extraction with methylene chloride and column chromatography gave the titled compound.

yield: 92%

¹H NMR(500 MHz, CDCl₃): δ 2.17(6H,s), 6.74(1H,s), 7.15(5H,m), 7.31(1H,s)

(d) Phenyl N-[2-(t-butyldimethylsilyloxy)-4,5-dimethylphenyl]carbamate

To a mixture of phenyl N-(4,5-dimethyl-2-hydroxyphenyl)carbamate (7.72 g, 0.03 mol) and imidazole (2.2 g, 33 mmol), methylene chloride(100 ml) was added, and with stirring t-butyldlmethylsilylchloride(5.0 g, 33 mmole) was added. Then the mixture was stirred for 2 hours, and water(150 ml) was added thereto. The resulting mixture was extracted with methylene chloride, dried, concentrated under the reduced pressure and purified by column chromatography to obtain the titled compound.

yield: 83%

¹H NMR(500 MHz, CDCl₃): δ 0.27(6H,s), 0.98(9H,s), 2.17(6H,s), 7.12(5H,m), 7.30(2H,s)

(e) 1-[(2-Hydroxy-4,5-dimethylphenyl) aminocarbonyl]-4-(3,5-dimethoxyphenyl)piperazine Phenyl N-[2-(t-butyldimethylsilyloxy)-4,5-dimethylphenyl]carbamate (0.17 g, 0.5 mmole) and 1-(3,5-dimethoxyphenyl)piperazine(0.13 g, 0.6 mmole) were dissolved in tetrahydrofuran(10 ml), and thereto with stirring DBU(0.09 g, 0.6 mmole) was added, and the resulting mixture was stirred for 2 hours, concentrated and chromatographed to obtain the titled compound.

yield: 87% m.p.: 145–146° C.

¹H NMR(500 MHz, CDCl₃): δ 2.14(3H,s), 2.18(3H,s), 3.26(4H,t), 3.67(4H,t), 3.79(6H,s), 6.07(3H,m), 6.40(3H,m), 6.67(1H,s), 6.82(1H,s), 8.87(1H,s)

EXAMPLE 229

1-[(2-Hydroxy-4,5-dimethylphenyl)aminocarbonyl]-4-(3,5-dimethoxyphenyl)piperazine Phenyl N-[2-hydroxy-4,5-dimethylphenyl)carbamate and 1-(3,5-dimethylphenyl)piperazine were reacted by the same way with the example 228 to obtain the titled compound.

yield: 84% m.p.: 160–162° C.

¹H NMR(500 MHz, CDCl₃): δ 2.13(3H,s), 2.17(3H,s), 2.31(6H,s), 3.26(4H,t), 3.75(4H,t), 6.73(3H,m), 6.81(1H,s), 8.86(1H,s)

EXAMPLE 230

1-[(2-Hydroxy-4,5-dimethylphenyl)aminocarbonyl]-4-(3,5-difluorophenyl)piperazine Phenyl N-[2-hydroxy-4,5-dimethylphenyl)carbamate and 1-(3,5-difluorophenyl)piperazine were reacted by the same way with the example 228 to obtain the titled compound.

yield: 80% m.p.: 152–154° C.

¹H NMR(500 MHz, CDCl₃): δ 2.17(3H,s), 2.20(3H,s), 3.30(4H,t), 3.70(4H,t), 6.40(3H,m), 6.70(1H,s), 6.82(1H,s), 6.98(1H,s)

EXAMPLE 231

1-[(2-hydroxy-4,5-dimethylphenyl)aminocarbonyl]-4-(3,5-dichlorophenyl)piperazine Phenyl N-(2-hydroxy-4,5-dimethylphenyl)carbamate and 1-(3,5-dichlorophenyl)piperazine were reacted by the same way with the example 228 to obtain the titled compound.

yield: 77% m.p.: oil phase

¹H NMR(500 MHz, CDCl₃): δ 2.15(3H,s), 2.20(3H,s), 3.32(4H,t), 3.69(4H,t), 6.29(3H,m), 6.69(1H,s), 6.81(1H,s), 8.65(1H,s)

Antitumor activities of compounds of the present invention were tested in vitro against 5 kinds of human tumor cell lines and 2 kinds of leukemia tumor cell lines. The method and result of in vitro tests is as follows.

Experimental 1

In vitro antitumor effect against human tumor cell lines.

| A. Tumor cell line : | A549 | (human non-small lung cell) |
|---|---|---|
| | SKOV-3 | (human ovarian) |
| | HCT-15 | (human colon) |
| | XF 498 | (human CNS) |
| | SKMEL-2 | (human melanoma) |

B. SRB Assay Method a. Human solid tumor cell lines, A549(non-small lung cell), SKMEL-2(melanoma), HCT-15(colon), SKOV-3 (ovarian), XF-498(CNS) were cultured at 37° C., in 5% $CO_2$ incubators using the RPMI 1640 media containing 10% FBS, while they were transfer-cultured successively once or twice per week. Cell cultures were dissolved in a solution of 0.25% trypsin and 3 mM CDTA PBS(–) and then cells were separated from media which the cells were sticked on.

b. $5 \times 10^3 \sim 2 \times 10^4$ cells were added into each well of 96-well plate and cultured in 5% $CO_2$ incubator, at 37° C., for 24 hours.

c. Each sample drug was dissolved in a little DMSO and diluted with the used medium to a prescribed concentration for experiments, wherein the final concentration of DMSO was controlled below 0.5%.

d. Medium of each well cultured for 24 hours as above b. was removed by aspiration. Each 200 μl of drug samples prepared in c. was added into each well and the wells were cultured for 48 hours. Tz(time zero) plates were collected at the point of time drugs were added.

e. According to the SRB assay method, cell fixing with TCA, staining with 0.4% SRB solution, washing with 1% acetic acid and elution of dye with 10 mM Tris solution were carried out on Tz plates and culture-ended plates, and then, OD values were measured at 520 nm.

C. Calculation of Result a. Time zero(Tz) value was determined with measuring the SRB protein value at the point of time drugs were added.

b. Control value(C) was determined with the OD value of an well untreated with drug.

c. Drug-treated test value(T) was determined with the OD value of drug-treated well.

d. Effects of drugs were estimated with growth stimulation, net growth inhibition, net killing etc. calculated from Tz, C and T.

e. If T≧Tz, cellular response function was calculated by 100×(T−Tz)/(C−Tz), and if T<Tz, by 100×(T−Tz)/Tz. The results are shown in the next table 1.

REFERENCE

1) P. Skehan, R. Strong, D Scudiero, A. Monks, J. B. Mcmahan, D. T. Vistica, J. Warren, H. Bokesh, S. Kenny and M. R. Boyd: Proc. Am. Assoc. Cancer Res., 30, 612(1989)

2) L. V. Rubinstein, R. H. Shoemaker, K. D. Paull, R. M. simon, S. Tosini, P. Skehan, D. Scudiero, A. Monks and M. R. boyd.; J. Natl. Cancer Inst., 82, 1113(1990)

3) P. Skehan, R. Strong, D. Scudiero, A. monks, J. B. Mcmahan, D. T. Vistica, J. Warren, H. Bokesh, S. Kenny and M. R. Boyd.;J. Natl. Cancer Ins., 82, 1107(1990)

D. Results

It was found that compounds of the present invention have the superior antitumor activities than those of cisplatin, one control, and equal to or higher antitumor activities than those of adriamycin, another control, against human solid cancer cell lines.

TABLE 1

$ED_{50}= \mu g/ml$

| Ex. No. | A549 | SK-OV-3 | SK-MEL-2 | XF-498 | HCT 15 |
|---|---|---|---|---|---|
| 4 | 0.007 | 0.022 | 0.007 | 0.94 | 0.093 |
| 5 | 0.71 | 0.96 | 0.60 | >10.0 | 0.96 |
| 9 | 0.15 | 0.07 | 0.21 | 0.11 | 0.11 |
| 11 | 0.91 | 0.56 | 0.62 | 0.73 | 0.71 |
| 14 | 0.022 | 0.02 | 0.001 | 0.16 | 0.007 |
| 15 | 0.002 | 0.05 | 0.052 | 0.035 | 0.038 |
| 16 | 0.008 | 0.04 | 0.038 | 0.005 | 0.061 |
| 17 | 0.018 | 0.01 | 0.021 | 0.077 | 0.008 |
| 22 | 0.0009 | 0.006 | 0.027 | 0.0053 | 0.01 |
| 23 | 0.09 | 0.04 | 0.09 | 0.092 | 0.05 |
| 24 | 0.03 | 0.006 | 0.01 | 0.234 | 0.01 |
| 27 | 0.02 | 0.11 | 0.01 | 0.046 | 0.165 |
| 28 | 0.06 | 0.07 | 0.001 | 0.41 | 0.05 |
| 46 | 0.21 | 0.12 | 0.08 | 0.14 | 0.16 |
| 47 | 0.92 | 0.62 | 0.47 | 0.64 | 0.81 |
| 53 | 0.47 | 0.47 | 0.64 | 0.67 | 0.71 |
| 56 | 0.017 | 0.0027 | 0.01 | 0.013 | 0.045 |
| 57 | 0.27 | 0.15 | 0.18 | 0.22 | 0.25 |
| 63 | 0.04 | 0.1 | 0.11 | 0.03 | 0.07 |
| 64 | 0.42 | 0.56 | 0.52 | 0.23 | 0.37 |
| 73 | 0.01 | 0.0054 | 0.02 | 0.013 | 0.012 |
| 74 | 0.016 | 0.0138 | 0.02 | 0.026 | 0.021 |
| 75 | 0.19 | 0.09 | 0.09 | 0.13 | 0.12 |
| 81 | 0.0032 | 0.0007 | 0.0107 | 0.0097 | 0.0054 |
| 82 | 0.0676 | 0.0249 | 0.0754 | 0.0479 | 0.0346 |
| 85 | 0.048 | 0.117 | 0.039 | 0.104 | 0.10 |
| 88 | 0.014 | 0.043 | 0.02 | 0.009 | 0.011 |
| 99 | 0.43 | 0.41 | 0.40 | 0.52 | 0.36 |
| 100 | 4.54 | 3.02 | 3.47 | 0.66 | 4.21 |
| 103 | 0.52 | 0.46 | 0.49 | 0.36 | 0.33 |
| 109 | 0.47 | 0.91 | 0.86 | 0.53 | 0.49 |
| 110 | 0.52 | 1.06 | 0.97 | 0.81 | 0.69 |
| 112 | 0.56 | 6.43 | 0.22 | 2.07 | 0.61 |
| 128 | 0.40 | 0.37 | 0.42 | 0.44 | 0.51 |
| 132 | 0.03 | 0.01 | 0.03 | 0.04 | 0.04 |
| 133 | 0.57 | 0.94 | 0.53 | 0.61 | 0.57 |
| 134 | 0.0009 | 0.0091 | 0.0086 | 0.002 | 0.0065 |
| 135 | 0.056 | 0.092 | 0.102 | 0.06 | 0.066 |
| 140 | 0.33 | 0.47 | 0.56 | 0.54 | 0.49 |
| 142 | 0.015 | 0.011 | 0.021 | 0.026 | 0.017 |
| 143 | 0.0004 | 0.0095 | 0.0121 | 0.0009 | 0.0108 |
| 147 | 0.031 | 0.092 | 0.024 | 0.466 | 0.18 |
| 148 | 0.01 | 0.07 | 0.03 | 0.05 | 0.05 |
| 151 | 0.004 | 0.008 | 0.007 | 0.007 | 0.037 |
| 152 | 0.18 | 0.37 | 0.2 | 0.26 | 0.44 |
| 156 | 0.06 | 0.10 | 0.09 | 0.06 | 0.07 |
| 157 | 0.000002 | 0.000002 | 0.000043 | 0.000245 | 0.000211 |

TABLE 1-continued $ED_{50}= \mu g/ml$

| Ex. No. | A549 | SK-OV-3 | SK-MEL-2 | XF-498 | HCT 15 |
|---|---|---|---|---|---|
| 159 | 0.05 | 0.10 | 0.07 | 0.21 | 0.17 |
| 171 | 0.000645 | 0.00372 | 0.003233 | 0.000572 | 0.001809 |
| 172 | 0.0047 | 0.0097 | 0.0233 | 0.0086 | 0.0180 |
| 174 | 0.54 | 0.56 | 0.27 | 0.49 | 0.33 |
| 177 | 0.52 | 0.39 | 0.17 | 0.12 | 0.09 |
| 179 | 1.04 | 0.98 | 0.72 | 0.74 | 0.63 |
| 183 | 0.42 | 2.27 | 1.17 | 1.41 | 2.09 |
| 184 | 0.28 | 0.34 | 0.17 | 0.12 | 0.20 |
| 190 | 0.004 | 0.008 | 0.002 | 0.443 | 0.017 |
| 191 | 0.09 | 0.28 | 0.06 | 0.47 | 0.40 |
| 198 | 0.021 | 0.068 | 0.008 | 0.072 | 0.56 |
| 200 | 0.50 | 0.53 | 0.26 | 1.01 | 0.44 |
| 201 | 0.014 | 0.053 | 0.049 | 0.026 | 0.071 |
| 202 | 0.57 | 1.26 | 0.48 | 2.09 | 0.64 |
| 206 | 0.47 | 0.54 | 0.52 | 0.70 | 0.38 |
| Cisplatin | 0.8184 | 0.7134 | 0.7147 | 0.7771 | 3.0381 |
| Adriamycin | 0.0168 | 0.0176 | 0.0108 | 0.0250 | 1.6689 |

Experimental 2

In vitro antitumor effects against animal leukemia cells.

A. Materials

Tumor cell lines : L1210(mouse leukemia cell)
P388 (mouse lymphoid neoplasma cell)

B. Method: Dye Exclusion Assay

1) The concentrations of L1210 and P388 cells being cultured in RPMI 1640 media containing 10% FBS were regulated to $1 \times 10^6$ cells/ml.

2) Sample drugs of respective concentrations diluted in the ratio of log doses were added into cell media, and cultured at 37° C., for 48 hours, in 50% $CO_2$ incubator, and then viable cell number was measured by dye exclusion test using trypan blue.

3) The concentration of sample compounds showing 50% cell growth inhibition($IC_{50}$) compared with the control were determined and listed in the table 2 below.

REFERENCE

1) P. Skehan, R. Strong, D. Scudiero, A. Monks, J. B. Mcmahan, D. T. Vistica, J. Warren, H. Bokesh, S. Kenney and M. R. Boyd.: Proc. Am. Assoc. Cancer Res., 30, 612(1989).

2) L. V. Rubinstein, R. H. Shoemaker, K. D. Paull, R. M. Simon, S. Tosini, P. Skehan, D. Scudiero, A. Monks, J. Natl. Cancer Inst., 82, 1113(1990)

3) P. Skehan, R. Strong, D. Scudiero, J. B. Mcmahan, D. T. Vistica, J. Warren, H. Bokesch, S. Kenney and M. R. Boyd.: J. Natl. Cancer Inst., 82, 1107(1990)

C. Results

As the results of measurement of antitumor activities of compounds of the present invention against L1210 and P388 mouse cancer cells, it was found that the compounds tested have equal to or higher antitumor activities than those of the control drug, mitomycin C.

| Ex. No. | L1210 | P388 |
|---|---|---|
| 8 | 0.9 | 0.4 |
| 12 | 0.2 | — |
| 13 | 0.5 | — |
| 14 | 0.3 | — |
| 15 | 0.3 | 0.4 |
| 16 | 0.5 | 0.3 |
| 17 | 1.2 | 0.8 |
| 24 | 0.5 | 0.5 |
| 49 | 1.5 | — |
| 56 | 0.2 | 0.2 |
| 57 | 1.8 | 1.2 |
| 60 | 1.1 | — |
| 63 | 0.5 | 0.3 |
| 64 | 1.9 | 1.4 |
| 69 | — | 0.5 |
| 71 | — | 0.07 |
| 72 | — | 0.9 |
| 73 | 0.2 | 0.04 |
| 74 | 0.5 | 0.4 |
| 76 | — | 0.4 |
| 77 | — | 0.5 |
| 132 | 0.4 | 0.4 |
| 134 | 0.5 | 0.2 |
| 140 | 1.8 | 1.6 |
| 143 | 0.5 | 0.4 |
| 144 | 1.2 | 0.5 |
| 148 | 1.6 | — |
| 149 | 1.0 | 0.6 |
| 151 | — | 1.2 |
| 152 | 0.3 | 0.3 |
| 154 | — | 0.1 |
| 157 | 1.7 | 1.0 |
| 158 | 0.5 | 0.2 |
| 170 | 0.4 | 0.4 |
| 173 | 0.5 | 0.2 |
| 178 | 1.8 | 1.6 |
| 181 | 0.5 | 0.4 |
| 182 | 1.2 | 0.5 |
| 186 | 1.6 | — |
| 187 | 1.0 | 0.6 |
| 190 | 0.3 | 0.3 |
| 195 | 1.7 | 1.0 |
| 196 | 0.5 | 0.2 |
| Mitomycin | 1.6 | 1.1 |

Experimental 3

In vivo antitumor effects against mouse leukemia P388 cells.

A. Material of Experiment

BDF1 mice were used.

B. Method of Experiment

1) Leukemia P388 cells being transfer-cultured successively in DBA/2 mouse, were grafted into each mouse of a group comprising 8 mice of 6 week old BDF1 mouse with the dose of $1\times10^6$ cells/0.1 ml.

2) Sample drugs were dissolved in PBS or suspended in 0.5% tween 80, and then injected into abdominal cavity of mouse at each prescribed concentration on days 1, 5, 9, respectively.

3) With observation everyday, survival times of tested mice were measured. Antitumor activities was determined in such a manner that the increasing ratio(T/C%) of average survival days of drug-treated groups compared with the control group was calculated using the mean survival times of each tested groups.

The results are shown at the next table 3.

| Ex. No. | Dose(mg/kg) | T/C(%) | Interval of administration |
|---|---|---|---|
| 8 | 200 | 140.9 | on days 1, 5, 9 |
|  | 100 | 104.5 |  |
| 15 | 25 | 150 | nine everyday |
|  | 10 | 110 |  |
| 16 | 50 | 165 | nine everyday |
|  | 25 | 110 |  |
| 22 | 100 | 150 | nine everyday |
|  | 50 | 140 |  |
|  | 25 | 110 |  |
| 56 | 200 | 227.3 | on days 1, 5, 9 |
|  | 100 | 140.9 |  |
|  | 50 | 118.2 |  |
| 56 | 50 | 165.0 | nine everyday |
|  | 25 | 145.0 |  |
|  | 10 | 140.0 |  |
| 73 | 50 | 180.0 | nine everyday |
|  | 25 | 150.0 |  |
|  | 10 | 140.0 |  |
| 74 | 50 | 250.0 | nine everyday |
|  | 25 | 150.0 |  |
|  | 10 | 140.0 |  |
| 81 | 200 | 218.2 | on days 1, 5, 9 |
|  | 100 | 145.5 |  |
|  | 50 | 127.3 |  |
| 81 | 50 | 210.0 | nine everyday |
|  | 25 | 140.0 |  |
|  | 10 | 140.0 |  |
| 82 | 100 | 127.3 | on days 1, 5, 9 |
|  | 50 | 100.0 |  |
| 98 | 100 | 150.0 | nine everyday |
|  | 50 | 110.0 |  |
|  | 25 | 110.0 |  |
| 135 | 100 | 150.0 | nine everyday |
|  | 50 | 110.0 |  |
|  | 25 | 100.0 |  |
| 144 | 200 | 125.0 | nine everyday |
|  | 100 | 110.0 |  |
|  | 50 | 110.0 |  |
| 171 | 100 | 140.0 | on days 1, 4, 8 |
|  | 50 | 100.0 |  |
|  | 25 | 100.0 |  |
| 172 | 200 | 190.9 | on days 1, 4, 8 |
|  | 100 | 127.3 |  |
|  | 50 | 118.2 |  |

REFERENCE

A. Goldin et al.: Euro. J. Cancer, 17, 129 (1981).

C. Result

Through in vivo experiments using P388 mouse cancer cells, significant antitumor effect of the compounds of examples were observed.

Experimental 4

Acute toxicity test ($LD_{50}$): Litchfield-Wilcoxon method.

6 weeks old ICR mice(male 30±2.0 g) were fed freely with solid feed and water at room temperature, 23±1° C. and at humidity 60±5%. Sample drugs were injected into the abdominal cavities of mice, while each group comprises 6 mice. Observed during 14 days, external appearances and life or dead were recorded, and then, visible pathogenies were observed from dead animals by dissection. $LD_{50}$ value was calculated by Litchfiled-wilcoxon method.

The results are shown at the next table 4.

| Ex. No. | LD$_{50}$(mg/kg)(i.p) |
|---|---|
| 8 | 707 |
| 12 | 165 |
| 13 | 284.8 |
| 15 | 190 |
| 16 | 282.8 |
| 22 | >2,000 |
| 28 | >2,000 |
| 56 | 410 |
| 57 | 455 |
| 73 | 250 |
| 74 | 361.4 |
| 81 | 1,600 |
| 82 | 700 |
| 170 | 573 |
| 172 | 723 |
| 182 | 348 |
| 184 | 309 |
| 186 | >2,000 |
| 187 | 417.6 |
| Cisplatin | 9.7 |

As described above, it was found that the compounds of the present invention are more safer and have superior antitumor activities to cisplatin, and accordingly have solved the problems of drugs by the prior art such as restriction of dosage, toxicity, etc.

What is claimed:

1. A compound of the general formula (I)

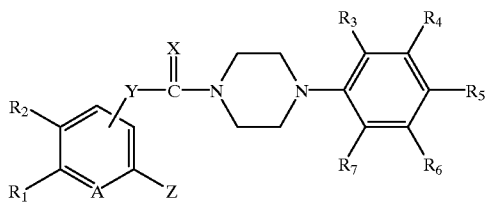

wherein, $R_1$ and $R_2$ are independently acetyl or vinyl, or $R_1$ and $R_2$ may fuse to form a saturated or unsaturated $C_3$–$C_4$ ring, $R_3$, $R_4$, $R_5$, $R_6$ and $R_7$ are independently hydrogen, halogen, hydroxy, $C_1$–$C_4$ alkyl or $C_1$–$C_4$ alkoxy, A is N or —CH, X is oxygen or sulfur, Y is —NH— or —NR$_8$— wherein R$_8$ is $C_1$–$C_4$ alkyl, which is bonded at the 3- or 4-position relative to A of the adjacent ring, Z is $C_1$–$C_4$ alkoxy, or a pharmaceutically acceptable acid addition salt thereof.

2. A process for the preparation of a compound of the general formula (I) according to claim 1 or a pharmaceutically acceptable acid addition salt thereof comprising reacting a compound of the general formula (a) with a —C(=X)— group-providing agent in the presence of an organic solvent to obtain a compound of the general formula (b) and reacting the compound of the general formula (b) with a compound of the general formula (c)

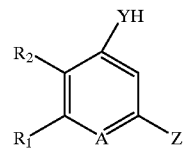

(a)

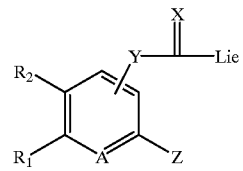

(b)

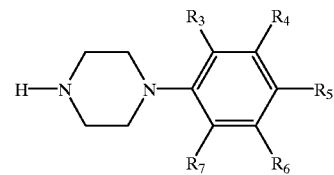

(c)

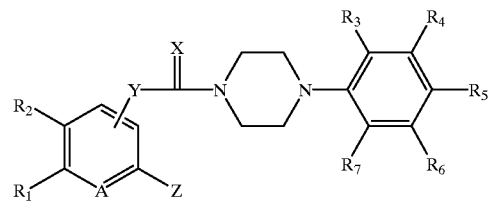

(I)

wherein, $R_1$, $R_2$, $R_3$, $R_4$, $R_5$, $R_6$, $R_7$, A, X, Y and Z are as defined in claim 5 and Lie is a leaving group.

3. A process for the preparation of a compound of the general formula (Ib) by introducing an $R_8$ providing agent into a compound of the general formula (Ia)

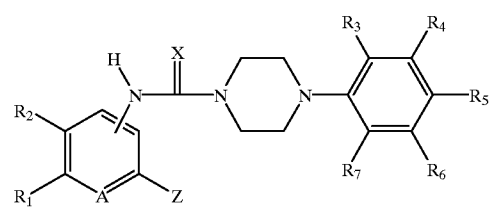

(Ia)

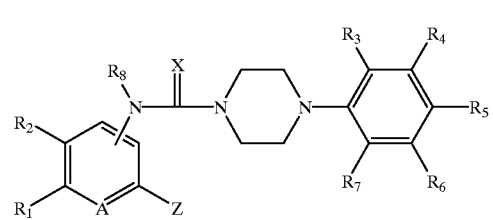

(Ib)

wherein $R_1$ and $R_2$ are independently acetyl or vinyl, or $R_1$ and $R_2$ may fuse to form a saturated or unsaturated $C_{3-4}$ ring, $R_3$, $R_4$, $R_5$, $R_6$ and $R_7$ are independently hydrogen, halogen, hydroxy, $C_1$–$C_4$ alkyl or $C_1$–$C_4$ alkoxy, A is N or —CH, X is oxygen or sulfur, $R_8$ is $C_1$–$C_4$ alkyl, and N—H or N—$R_8$ is bonded at the 3- or 4-position relative to A of the adjacent ring, Z is $C_1$–$C_4$ alkoxy.

* * * * *